(12) United States Patent
DiMauro

(10) Patent No.: US 9,814,589 B2
(45) Date of Patent: Nov. 14, 2017

(54) IN-SITU FORMED INTERVERTEBRAL FUSION DEVICE AND METHOD

(71) Applicant: DePuy Synthes Products, Inc., Raynham, MA (US)

(72) Inventor: Thomas M. DiMauro, Southboro, MA (US)

(73) Assignee: DePuy Synthes Products, Inc., Raynham, MA (US)

(*) Notice: Subject to any disclaimer, the term of this patent is extended or adjusted under 35 U.S.C. 154(b) by 0 days.

(21) Appl. No.: 14/856,716

(22) Filed: Sep. 17, 2015

(65) Prior Publication Data

US 2016/0000577 A1    Jan. 7, 2016

Related U.S. Application Data

(63) Continuation of application No. 14/684,959, filed on Apr. 13, 2015, now Pat. No. 9,333,091, which is a (Continued)

(51) Int. Cl.
*A61F 2/44* (2006.01)
*A61K 49/00* (2006.01)
(Continued)

(52) U.S. Cl.
CPC ........ *A61F 2/441* (2013.01); *A61B 17/00234* (2013.01); *A61F 2/28* (2013.01);
(Continued)

(58) Field of Classification Search
CPC ................... A61F 2/447; A61F 2/4455; A61F 2002/30579
(Continued)

(56) References Cited

U.S. PATENT DOCUMENTS 1,965,653 A    7/1934  Kennedy
2,115,250 A    4/1938  Bruson
(Continued)

FOREIGN PATENT DOCUMENTS

AU    2006279558 A1    2/2007
CA       2617872 A1    2/2007
(Continued)

OTHER PUBLICATIONS

[No Author Listed] FDA Approves Cambridge Scientific, Inc.'s Orthopedic WISORB (TM) Malleolar Screw [online], Jul. 30, 2002 [retrieved on Oct. 14, 2003]. Retrieved from the Internet <URL: http://www.cambridgescientificinc.com>.
(Continued)

*Primary Examiner* — Ellen C Hammond
*Assistant Examiner* — Christina Negrellirodrigue
(74) *Attorney, Agent, or Firm* — Nutter McClennen & Fish LLP

(57) ABSTRACT

An orthopedic device for implanting between adjacent vertebrae comprising: an arcuate balloon and a hardenable material within said balloon.
In some embodiments, the balloon has a footprint that substantially corresponds to a perimeter of a vertebral endplate. An inflatable device is inserted through a cannula into an intervertebral space and oriented so that, upon expansion, a natural angle between vertebrae will be at least partially restored. At least one component selected from the group consisting of a load-bearing component and an osteobiologic component is directed into the inflatable device through a fluid communication means.

18 Claims, 28 Drawing Sheets

Related U.S. Application Data continuation of application No. 14/674,070, filed on Mar. 31, 2015, now Pat. No. 9,439,777, which is a continuation of application No. 14/668,576, filed on Mar. 25, 2015, which is a continuation of application No. 14/640,741, filed on Mar. 6, 2015, now Pat. No. 9,439,776, which is a continuation of application No. 14/632,875, filed on Feb. 26, 2015, which is a continuation of application No. 13/490,743, filed on Jun. 7, 2012, which is a continuation of application No. 10/778,684, filed on Feb. 13, 2004, now abandoned.

(60) Provisional application No. 60/448,221, filed on Feb. 14, 2003.

(51) Int. Cl.
| | |
|---|---|
| *A61L 27/12* | (2006.01) |
| *A61L 27/18* | (2006.01) |
| *A61L 27/38* | (2006.01) |
| *A61L 27/50* | (2006.01) |
| *A61L 27/52* | (2006.01) |
| *A61L 27/54* | (2006.01) |
| *A61B 17/00* | (2006.01) |
| *A61F 2/46* | (2006.01) |
| *A61K 9/00* | (2006.01) |
| *A61F 2/30* | (2006.01) |
| *A61F 2/28* | (2006.01) |

(52) U.S. Cl.
CPC ............ *A61F 2/442* (2013.01); *A61F 2/446* (2013.01); *A61F 2/4425* (2013.01); *A61F 2/4455* (2013.01); *A61F 2/4465* (2013.01); *A61F 2/4601* (2013.01); *A61F 2/4611* (2013.01); *A61K 9/0024* (2013.01); *A61K 49/006* (2013.01); *A61L 27/12* (2013.01); *A61L 27/18* (2013.01); *A61L 27/3821* (2013.01); *A61L 27/3839* (2013.01); *A61L 27/50* (2013.01); *A61L 27/52* (2013.01); *A61L 27/54* (2013.01); *A61F 2/30965* (2013.01); *A61F 2002/2817* (2013.01); *A61F 2002/2835* (2013.01); *A61F 2002/302* (2013.01); *A61F 2002/3023* (2013.01); *A61F 2002/3055* (2013.01); *A61F 2002/30062* (2013.01); *A61F 2002/30065* (2013.01); *A61F 2002/30092* (2013.01); *A61F 2002/30131* (2013.01); *A61F 2002/30224* (2013.01); *A61F 2002/30308* (2013.01); *A61F 2002/30383* (2013.01); *A61F 2002/30451* (2013.01); *A61F 2002/30556* (2013.01); *A61F 2002/30579* (2013.01); *A61F 2002/30583* (2013.01); *A61F 2002/30586* (2013.01); *A61F 2002/30604* (2013.01); *A61F 2002/30622* (2013.01); *A61F 2002/30841* (2013.01); *A61F 2002/30971* (2013.01); *A61F 2002/448* (2013.01); *A61F 2002/4475* (2013.01); *A61F 2002/4627* (2013.01); *A61F 2002/4635* (2013.01); *A61F 2002/4677* (2013.01); *A61F 2210/0004* (2013.01); *A61F 2210/0014* (2013.01); *A61F 2210/0061* (2013.01); *A61F 2210/0071* (2013.01); *A61F 2210/0085* (2013.01); *A61F 2220/0016* (2013.01); *A61F 2220/0025* (2013.01); *A61F 2220/0058* (2013.01); *A61F 2230/0013* (2013.01); *A61F 2230/0063* (2013.01); *A61F 2230/0065* (2013.01); *A61F 2230/0069* (2013.01); *A61F 2250/001* (2013.01); *A61F 2250/0003* (2013.01); *A61F 2250/0009* (2013.01); *A61F 2250/0065* (2013.01); *A61F 2310/00011* (2013.01); *A61F 2310/00179* (2013.01); *A61F 2310/00365* (2013.01); *A61L 2300/252* (2013.01); *A61L 2300/256* (2013.01); *A61L 2300/404* (2013.01); *A61L 2300/414* (2013.01); *A61L 2300/43* (2013.01); *A61L 2300/64* (2013.01); *A61L 2430/38* (2013.01)

(58) Field of Classification Search
USPC .................... 623/17.11–17.16; 606/246–249
See application file for complete search history.

(56) References Cited

U.S. PATENT DOCUMENTS

| | | |
|---|---|---|
| 2,170,111 A | 8/1939 | Bruson |
| 2,229,024 A | 1/1941 | Bruson |
| 2,706,701 A | 4/1955 | Beller et al. |
| 2,710,277 A | 6/1955 | Shelanski et al. |
| 2,826,532 A | 3/1958 | Hosmer |
| 2,900,305 A | 8/1959 | Siggia |
| 2,977,315 A | 3/1961 | Scheib et al. |
| 3,091,237 A | 5/1963 | Skinner |
| 3,112,743 A | 12/1963 | Cochran et al. |
| 3,228,828 A | 1/1966 | Romano |
| 3,648,294 A | 3/1972 | Shahrestani |
| 3,717,655 A | 2/1973 | Godefroi et al. |
| 3,800,788 A | 4/1974 | White |
| 3,867,728 A | 2/1975 | Stubstad et al. |
| 3,875,595 A | 4/1975 | Froning |
| 3,889,665 A | 6/1975 | Ling et al. |
| 3,964,480 A | 6/1976 | Froning |
| 4,262,676 A | 4/1981 | Jamshidi |
| 4,274,163 A | 6/1981 | Malcom et al. |
| 4,312,337 A | 1/1982 | Donohue |
| 4,313,434 A | 2/1982 | Segal |
| 4,349,921 A | 9/1982 | Kuntz |
| 4,352,883 A | 10/1982 | Lim |
| 4,399,814 A | 8/1983 | Pratt, Jr. et al. |
| 4,440,921 A | 4/1984 | Allcock et al. |
| 4,462,394 A | 7/1984 | Jacobs |
| 4,466,435 A | 8/1984 | Murray |
| 4,467,479 A | 8/1984 | Brody |
| 4,488,549 A | 12/1984 | Lee et al. |
| 4,495,174 A | 1/1985 | Allcock et al. |
| 4,562,598 A | 1/1986 | Kranz |
| 4,595,006 A | 6/1986 | Burke et al. |
| 4,625,722 A | 12/1986 | Murray |
| 4,627,434 A | 12/1986 | Murray |
| 4,628,945 A | 12/1986 | Johnson, Jr. |
| 4,630,616 A | 12/1986 | Tretinyak |
| 4,645,503 A | 2/1987 | Lin et al. |
| 4,651,717 A | 3/1987 | Jakubczak |
| 4,665,906 A | 5/1987 | Jervis |
| 4,686,973 A | 8/1987 | Frisch |
| 4,697,584 A | 10/1987 | Haynes |
| 4,706,670 A | 11/1987 | Andersen et al. |
| 4,714,478 A | 12/1987 | Fischer |
| 4,743,256 A | 5/1988 | Brantigan |
| 4,759,766 A | 7/1988 | Buettner-Danz et al. |
| 4,772,287 A | 9/1988 | Ray et al. |
| 4,834,069 A | 5/1989 | Umeda |
| 4,838,282 A | 6/1989 | Strasser et al. |
| 4,863,476 A | 9/1989 | Shepperd |
| 4,871,366 A | 10/1989 | von Recum et al. |
| 4,878,915 A | 11/1989 | Brantigan |
| 4,880,622 A | 11/1989 | Allcock et al. |
| 4,888,022 A | 12/1989 | Huebsch |
| 4,888,024 A | 12/1989 | Powlan |
| 4,892,550 A | 1/1990 | Huebsch |
| 4,896,662 A | 1/1990 | Noble |
| 4,898,577 A | 2/1990 | Badger et al. |
| 4,904,261 A | 2/1990 | Dove et al. |
| 4,911,718 A | 3/1990 | Lee et al. |
| 4,932,969 A | 6/1990 | Frey et al. |
| 4,941,466 A | 7/1990 | Romano |

(56) References Cited

U.S. PATENT DOCUMENTS

| | | |
|---|---|---|
| 4,946,378 A | 8/1990 | Hirayama et al. |
| 4,961,740 A | 10/1990 | Ray et al. |
| 4,969,888 A | 11/1990 | Scholten et al. |
| 5,015,247 A | 5/1991 | Michelson |
| 5,015,255 A | 5/1991 | Kuslich |
| 5,030,233 A | 7/1991 | Ducheyne |
| 5,051,189 A | 9/1991 | Farrah |
| 5,053,035 A | 10/1991 | McLaren |
| 5,055,104 A | 10/1991 | Ray |
| 5,059,193 A | 10/1991 | Kuslich |
| 5,071,435 A | 12/1991 | Fuchs et al. |
| 5,071,437 A | 12/1991 | Steffee |
| 5,098,435 A | 3/1992 | Stednitz et al. |
| 5,102,413 A | 4/1992 | Poddar |
| 5,108,404 A | 4/1992 | Scholten et al. |
| 5,122,130 A | 6/1992 | Keller |
| 5,123,926 A | 6/1992 | Pisharodi |
| 5,133,755 A | 7/1992 | Brekke |
| 5,134,477 A | 7/1992 | Knauer et al. |
| 5,147,366 A | 9/1992 | Arroyo et al. |
| 5,163,989 A | 11/1992 | Campbell et al. |
| 5,171,280 A | 12/1992 | Baumgartner |
| 5,176,683 A | 1/1993 | Kimsey et al. |
| 5,176,692 A | 1/1993 | Wilk et al. |
| 5,183,052 A | 2/1993 | Terwilliger |
| 5,192,327 A | 3/1993 | Brantigan |
| 5,228,441 A | 7/1993 | Lundquist |
| 5,242,448 A | 9/1993 | Pettine et al. |
| 5,242,879 A | 9/1993 | Abe et al. |
| 5,257,632 A | 11/1993 | Turkel et al. |
| 5,263,953 A | 11/1993 | Bagby |
| 5,285,795 A | 2/1994 | Ryan et al. |
| 5,290,312 A | 3/1994 | Kojimoto et al. |
| 5,303,718 A | 4/1994 | Krajicek |
| 5,306,308 A | 4/1994 | Gross et al. |
| 5,306,310 A | 4/1994 | Siebels |
| 5,314,477 A | 5/1994 | Marnay |
| 5,322,505 A | 6/1994 | Krause et al. |
| 5,330,429 A | 7/1994 | Noguchi et al. |
| 5,331,975 A | 7/1994 | Bonutti |
| 5,344,252 A | 9/1994 | Kakimoto |
| 5,361,752 A | 11/1994 | Moll et al. |
| 5,370,697 A | 12/1994 | Baumgartner |
| 5,372,660 A | 12/1994 | Davidson et al. |
| 5,374,267 A | 12/1994 | Siegal |
| 5,383,932 A | 1/1995 | Wilson et al. |
| 5,385,151 A | 1/1995 | Scarfone et al. |
| 5,390,683 A | 2/1995 | Pisharodi |
| 5,397,364 A | 3/1995 | Kozak et al. |
| 5,401,269 A | 3/1995 | Buttner-Danz et al. |
| 5,410,016 A | 4/1995 | Hubbell et al. |
| 5,423,816 A | 6/1995 | Lin |
| 5,423,817 A | 6/1995 | Lin |
| 5,423,850 A | 6/1995 | Berger |
| 5,425,773 A | 6/1995 | Boyd et al. |
| 5,431,658 A | 7/1995 | Moskovich |
| 5,441,538 A | 8/1995 | Bonutti |
| 5,443,514 A | 8/1995 | Steffee |
| 5,454,365 A | 10/1995 | Bonutti |
| 5,454,827 A | 10/1995 | Aust et al. |
| 5,456,686 A | 10/1995 | Klapper et al. |
| 5,458,641 A | 10/1995 | Ramirez |
| 5,458,643 A | 10/1995 | Oka et al. |
| 5,462,563 A | 10/1995 | Shearer et al. |
| 5,468,245 A | 11/1995 | Vargas, III |
| 5,480,400 A | 1/1996 | Berger |
| 5,484,437 A | 1/1996 | Michelson |
| 5,507,816 A | 4/1996 | Bullivant |
| 5,509,923 A | 4/1996 | Middleman et al. |
| 5,514,143 A | 5/1996 | Bonutti et al. |
| 5,514,153 A | 5/1996 | Bonutti |
| 5,514,180 A | 5/1996 | Heggeness et al. |
| 5,522,398 A | 6/1996 | Goldenberg et al. |
| 5,522,790 A | 6/1996 | Moll et al. |
| 5,522,846 A | 6/1996 | Bonutti |
| 5,522,895 A | 6/1996 | Mikos |
| 5,522,899 A | 6/1996 | Michelson |
| 5,527,343 A | 6/1996 | Bonutti |
| 5,527,624 A | 6/1996 | Higgins et al. |
| 5,531,856 A | 7/1996 | Moll et al. |
| 5,534,023 A | 7/1996 | Henley |
| 5,534,029 A | 7/1996 | Shima |
| 5,534,030 A | 7/1996 | Navarro et al. |
| 5,538,009 A | 7/1996 | Byrne et al. |
| 5,540,711 A | 7/1996 | Kieturakis et al. |
| 5,545,222 A | 8/1996 | Bonutti |
| 5,549,679 A | 8/1996 | Kuslich |
| 5,554,191 A | 9/1996 | Lahille |
| 5,556,431 A | 9/1996 | Buttner-Danz |
| 5,562,736 A | 10/1996 | Ray et al. |
| 5,562,738 A | 10/1996 | Boyd et al. |
| 5,571,109 A | 11/1996 | Bertagnoli |
| 5,571,189 A | 11/1996 | Kuslich |
| 5,571,190 A | 11/1996 | Ulrich et al. |
| 5,575,790 A | 11/1996 | Chen et al. |
| 5,593,409 A | 1/1997 | Michelson |
| 5,601,556 A | 2/1997 | Pisharodi |
| 5,601,572 A | 2/1997 | Middleman et al. |
| 5,609,635 A | 3/1997 | Michelson |
| 5,632,746 A | 5/1997 | Middleman et al. |
| 5,645,596 A | 7/1997 | Kim et al. |
| 5,645,597 A | 7/1997 | Krapiva |
| 5,653,763 A | 8/1997 | Errico et al. |
| 5,658,335 A | 8/1997 | Allen |
| 5,665,122 A | 9/1997 | Kambin |
| 5,669,926 A | 9/1997 | Aust et al. |
| 5,674,294 A | 10/1997 | Bainville et al. |
| 5,674,295 A | 10/1997 | Ray et al. |
| 5,674,296 A | 10/1997 | Bryan et al. |
| 5,676,701 A | 10/1997 | Yuan et al. |
| 5,679,723 A | 10/1997 | Cooper et al. |
| 5,681,263 A | 10/1997 | Flesch |
| 5,683,465 A | 11/1997 | Shinn et al. |
| 5,693,100 A | 12/1997 | Pisharodi |
| 5,695,513 A | 12/1997 | Johnson et al. |
| 5,697,977 A | 12/1997 | Pisharodi |
| 5,700,239 A | 12/1997 | Yoon |
| 5,702,449 A | 12/1997 | McKay |
| 5,702,450 A | 12/1997 | Bisserie et al. |
| 5,702,453 A | 12/1997 | Rabbe et al. |
| 5,702,454 A | 12/1997 | Baumgartner |
| 5,716,415 A | 2/1998 | Steffee |
| 5,716,416 A | 2/1998 | Lin |
| 5,741,253 A | 4/1998 | Michelson |
| 5,749,879 A | 5/1998 | Middleman et al. |
| 5,755,797 A | 5/1998 | Baumgartner |
| 5,755,798 A | 5/1998 | Papavero et al. |
| 5,756,127 A | 5/1998 | Grisoni et al. |
| 5,766,252 A | 6/1998 | Henry et al. |
| 5,772,661 A | 6/1998 | Michelson |
| 5,782,832 A | 7/1998 | Larsen et al. |
| 5,788,703 A | 8/1998 | Mittelmeier et al. |
| 5,800,549 A | 9/1998 | Bao et al. |
| 5,807,275 A | 9/1998 | Jamshidi |
| 5,807,327 A | 9/1998 | Green et al. |
| 5,820,628 A | 10/1998 | Middleman et al. |
| 5,823,979 A | 10/1998 | Mezo |
| 5,824,084 A | 10/1998 | Muschler |
| 5,824,093 A | 10/1998 | Ray et al. |
| 5,824,094 A | 10/1998 | Serhan et al. |
| 5,827,289 A | 10/1998 | Reiley et al. |
| 5,833,657 A | 11/1998 | Reinhardt et al. |
| 5,836,948 A | 11/1998 | Zucherman et al. |
| 5,837,752 A | 11/1998 | Shastri et al. |
| 5,848,986 A | 12/1998 | Lundquist et al. |
| 5,851,212 A | 12/1998 | Lirps et al. |
| 5,860,973 A | 1/1999 | Michelson |
| 5,860,977 A | 1/1999 | Zucherman et al. |
| 5,865,846 A | 2/1999 | Bryan et al. |
| 5,865,848 A * | 2/1999 | Baker ............... A61F 2/4455 606/247 |
| 5,888,220 A | 3/1999 | Felt et al. |
| 5,888,224 A | 3/1999 | Beckers et al. |
| 5,888,226 A | 3/1999 | Rogozinski |

(56) References Cited

U.S. PATENT DOCUMENTS

| | | | |
|---|---|---|---|
| 5,888,227 A | 3/1999 | Cottle |
| 5,893,889 A | 4/1999 | Harrington |
| 5,893,890 A | 4/1999 | Pisharodi |
| 5,895,428 A | 4/1999 | Berry |
| 5,904,690 A | 5/1999 | Middleman et al. |
| 5,919,235 A | 7/1999 | Husson et al. |
| 5,925,074 A | 7/1999 | Gingras et al. |
| 5,961,554 A | 10/1999 | Janson et al. |
| 5,972,015 A | 10/1999 | Scribner et al. |
| 5,972,385 A | 10/1999 | Liu et al. |
| 5,976,186 A | 11/1999 | Bao et al. |
| 5,980,522 A | 11/1999 | Koros et al. |
| 5,985,307 A | 11/1999 | Hanson et al. |
| 5,989,291 A | 11/1999 | Ralph et al. |
| 6,012,494 A | 1/2000 | Balazs |
| 6,015,436 A | 1/2000 | Schonhoffer |
| 6,019,792 A | 2/2000 | Cauthen |
| 6,019,793 A | 2/2000 | Perren et al. |
| 6,022,350 A | 2/2000 | Ganem |
| 6,030,401 A | 2/2000 | Marino |
| 6,033,406 A | 3/2000 | Mathews |
| 6,033,412 A | 3/2000 | Losken et al. |
| 6,039,740 A | 3/2000 | Olerud |
| 6,039,761 A | 3/2000 | Li et al. |
| 6,039,763 A | 3/2000 | Shelokov |
| 6,045,552 A | 4/2000 | Zucherman et al. |
| 6,045,579 A | 4/2000 | Hochshuler et al. |
| 6,048,342 A | 4/2000 | Zucherman et al. |
| 6,048,346 A | 4/2000 | Reiley et al. |
| 6,048,360 A | 4/2000 | Khosravi et al. |
| 6,063,121 A | 5/2000 | Xavier et al. |
| 6,066,154 A | 5/2000 | Reiley et al. |
| 6,068,630 A | 5/2000 | Zucherman et al. |
| 6,071,982 A | 6/2000 | Wise et al. |
| 6,073,051 A | 6/2000 | Sharkey et al. |
| 6,083,225 A | 7/2000 | Winslow et al. |
| 6,090,143 A | 7/2000 | Meriwether et al. |
| 6,096,080 A | 8/2000 | Nicholson et al. |
| 6,099,531 A | 8/2000 | Bonutti |
| 6,102,950 A | 8/2000 | Vaccaro |
| 6,106,557 A | 8/2000 | Robioneck et al. |
| 6,110,210 A | 8/2000 | Norton et al. |
| 6,113,624 A | 9/2000 | Bezwada et al. |
| 6,113,637 A | 9/2000 | Gill et al. |
| 6,113,638 A | 9/2000 | Williams et al. |
| 6,113,640 A | 9/2000 | Tormala et al. |
| 6,117,174 A | 9/2000 | Nolan |
| 6,119,044 A | 9/2000 | Kuzma |
| 6,123,705 A | 9/2000 | Michelson |
| 6,126,660 A | 10/2000 | Dietz |
| 6,126,689 A | 10/2000 | Brett |
| 6,127,597 A | 10/2000 | Beyar et al. |
| 6,129,763 A | 10/2000 | Chauvin et al. |
| 6,136,031 A | 10/2000 | Middleton |
| 6,139,579 A | 10/2000 | Steffee et al. |
| 6,146,387 A | 11/2000 | Trott et al. |
| 6,146,421 A | 11/2000 | Gordon et al. |
| 6,147,135 A | 11/2000 | Yuan et al. |
| 6,159,211 A | 12/2000 | Boriani et al. |
| 6,159,244 A | 12/2000 | Suddaby |
| 6,162,252 A | 12/2000 | Kuras et al. |
| 6,165,218 A | 12/2000 | Husson et al. |
| 6,165,486 A | 12/2000 | Marra et al. |
| 6,171,610 B1 | 1/2001 | Vacanti et al. |
| 6,174,337 B1 | 1/2001 | Keenan |
| 6,176,882 B1 * | 1/2001 | Biedermann ............ A61F 2/447 623/17.11 |
| 6,179,794 B1 | 1/2001 | Burras |
| 6,179,873 B1 | 1/2001 | Lientek |
| 6,183,517 B1 | 2/2001 | Suddaby |
| 6,187,043 B1 | 2/2001 | Ledergerber |
| 6,187,048 B1 | 2/2001 | Milner et al. |
| 6,190,414 B1 | 2/2001 | Young et al. |
| 6,193,757 B1 | 2/2001 | Foley et al. |
| 6,197,033 B1 | 3/2001 | Haid, Jr. et al. |
| 6,197,065 B1 | 3/2001 | Martin et al. |
| 6,197,325 B1 | 3/2001 | MacPhee et al. |
| 6,203,565 B1 | 3/2001 | Bonutti et al. |
| D439,980 S | 4/2001 | Reiley et al. |
| 6,214,368 B1 | 4/2001 | Lee et al. |
| 6,217,579 B1 * | 4/2001 | Koros ............... A61F 2/30744 623/17.11 |
| 6,221,082 B1 | 4/2001 | Marino et al. |
| 6,224,603 B1 | 5/2001 | Marino |
| 6,224,631 B1 | 5/2001 | Kohrs |
| 6,224,894 B1 | 5/2001 | Jamiolkowski et al. |
| 6,235,030 B1 | 5/2001 | Zucherman et al. |
| 6,235,043 B1 | 5/2001 | Reiley et al. |
| 6,238,491 B1 | 5/2001 | Davidson et al. |
| 6,241,734 B1 | 6/2001 | Scribner et al. |
| 6,248,110 B1 | 6/2001 | Reiley et al. |
| 6,248,131 B1 | 6/2001 | Felt et al. |
| 6,251,140 B1 | 6/2001 | Marino et al. |
| 6,261,289 B1 | 7/2001 | Levy |
| 6,264,695 B1 | 7/2001 | Stoy |
| 6,267,763 B1 | 7/2001 | Castro |
| 6,277,149 B1 | 8/2001 | Boyle et al. |
| 6,280,456 B1 | 8/2001 | Scribner et al. |
| 6,280,474 B1 | 8/2001 | Cassidy et al. |
| 6,280,475 B1 | 8/2001 | Bao et al. |
| 6,290,724 B1 | 9/2001 | Marino |
| D449,691 S | 10/2001 | Reiley et al. |
| 6,296,647 B1 | 10/2001 | Robioneck et al. |
| 6,302,914 B1 | 10/2001 | Michelson |
| 6,306,177 B1 | 10/2001 | Felt et al. |
| 6,312,443 B1 | 11/2001 | Stone |
| 6,331,312 B1 | 12/2001 | Lee et al. |
| 6,332,894 B1 | 12/2001 | Stalcup et al. |
| 6,332,895 B1 | 12/2001 | Suddaby |
| 6,364,828 B1 | 4/2002 | Yeung et al. |
| 6,368,325 B1 | 4/2002 | McKinley et al. |
| 6,368,350 B1 | 4/2002 | Erickson et al. |
| 6,368,351 B1 | 4/2002 | Glenn et al. |
| 6,375,681 B1 | 4/2002 | Truscott |
| 6,375,682 B1 | 4/2002 | Fleischmann et al. |
| 6,387,130 B1 | 5/2002 | Stone et al. |
| 6,402,750 B1 | 6/2002 | Atkinson et al. |
| 6,409,766 B1 | 6/2002 | Brett |
| 6,413,278 B1 | 7/2002 | Marchosky |
| 6,416,551 B1 | 7/2002 | Keller |
| 6,419,641 B1 | 7/2002 | Mark et al. |
| 6,419,705 B1 * | 7/2002 | Erickson ............... A61F 2/446 623/17.11 |
| 6,419,706 B1 | 7/2002 | Graf |
| 6,423,071 B1 | 7/2002 | Lawson |
| 6,423,083 B2 | 7/2002 | Reiley et al. |
| 6,423,089 B1 | 7/2002 | Gingras et al. |
| 6,425,887 B1 | 7/2002 | McGuckin et al. |
| 6,425,919 B1 | 7/2002 | Lambrecht |
| 6,428,541 B1 | 8/2002 | Boyd et al. |
| 6,436,140 B1 | 8/2002 | Liu et al. |
| 6,440,138 B1 | 8/2002 | Reiley et al. |
| 6,443,989 B1 | 9/2002 | Jackson |
| 6,451,019 B1 | 9/2002 | Zucherman et al. |
| 6,454,806 B1 | 9/2002 | Cohen et al. |
| 6,454,807 B1 | 9/2002 | Jackson |
| 6,468,279 B1 | 10/2002 | Reo |
| 6,468,310 B1 | 10/2002 | Ralph et al. |
| 6,478,805 B1 | 11/2002 | Marino et al. |
| 6,482,235 B1 | 11/2002 | Lambrecht et al. |
| 6,485,518 B1 | 11/2002 | Cornwall et al. |
| D467,657 S | 12/2002 | Scribner |
| 6,488,710 B2 | 12/2002 | Besselink |
| 6,491,626 B1 | 12/2002 | Stone et al. |
| 6,491,695 B1 | 12/2002 | Roggenbuck |
| 6,491,724 B1 | 12/2002 | Ferree |
| 6,494,883 B1 | 12/2002 | Ferree |
| 6,498,421 B1 | 12/2002 | Oh et al. |
| 6,500,178 B2 | 12/2002 | Zucherman et al. |
| 6,500,205 B1 | 12/2002 | Michelson |
| 6,508,839 B1 | 1/2003 | Lambrecht et al. |
| 6,511,471 B2 | 1/2003 | Rosenman et al. |
| 6,512,958 B1 | 1/2003 | Swoyer et al. |
| D469,871 S | 2/2003 | Sand |

(56) References Cited

U.S. PATENT DOCUMENTS

| | | |
|---|---|---|
| 6,517,580 B1 | 2/2003 | Ramadan et al. |
| 6,520,991 B2 | 2/2003 | Huene |
| D472,323 S | 3/2003 | Sand |
| 6,527,804 B1 | 3/2003 | Gauchet et al. |
| 6,530,930 B1 | 3/2003 | Marino et al. |
| 6,533,791 B1 | 3/2003 | Betz et al. |
| 6,533,797 B1 | 3/2003 | Stone et al. |
| 6,533,818 B1 | 3/2003 | Weber et al. |
| 6,540,747 B1 | 4/2003 | Marino |
| 6,547,823 B2 | 4/2003 | Scarborough et al. |
| 6,554,833 B2 | 4/2003 | Levy et al. |
| 6,558,390 B2 | 5/2003 | Cragg |
| 6,558,424 B2 | 5/2003 | Thalgott |
| 6,562,072 B1 | 5/2003 | Fuss et al. |
| 6,562,074 B2 * | 5/2003 | Gerbec ............... A61F 2/4455 623/17.15 |
| 6,575,919 B1 | 6/2003 | Reiley et al. |
| 6,575,979 B1 | 6/2003 | Cragg |
| 6,576,016 B1 | 6/2003 | Hochshuler et al. |
| 6,579,291 B1 | 6/2003 | Keith et al. |
| 6,579,320 B1 | 6/2003 | Gauchet et al. |
| 6,582,431 B1 | 6/2003 | Ray |
| 6,582,433 B2 | 6/2003 | Yun |
| 6,582,466 B1 | 6/2003 | Gauchet |
| 6,582,468 B1 | 6/2003 | Gauchet |
| 6,592,624 B1 | 7/2003 | Fraser et al. |
| 6,592,625 B2 | 7/2003 | Cauthen |
| 6,595,998 B2 | 7/2003 | Johnson et al. |
| 6,599,294 B2 | 7/2003 | Fuss et al. |
| 6,602,293 B1 | 8/2003 | Biermann et al. |
| 6,607,530 B1 | 8/2003 | Carl et al. |
| 6,607,544 B1 | 8/2003 | Boucher et al. |
| 6,607,558 B2 | 8/2003 | Kuras |
| 6,610,094 B2 | 8/2003 | Husson |
| 6,613,054 B2 | 9/2003 | Scribner et al. |
| 6,620,196 B1 | 9/2003 | Trieu |
| 6,623,505 B2 | 9/2003 | Scribner et al. |
| 6,626,943 B2 | 9/2003 | Eberlein et al. |
| 6,632,235 B2 | 10/2003 | Weikel et al. |
| D482,787 S | 11/2003 | Reiss |
| 6,641,587 B2 | 11/2003 | Scribner et al. |
| 6,641,614 B1 | 11/2003 | Wagner et al. |
| 6,645,213 B2 | 11/2003 | Sand et al. |
| 6,645,248 B2 | 11/2003 | Casutt |
| 6,648,917 B2 | 11/2003 | Gerbec et al. |
| 6,652,592 B1 | 11/2003 | Grooms et al. |
| D483,495 S | 12/2003 | Sand |
| 6,656,178 B1 | 12/2003 | Veldhuizen et al. |
| 6,656,180 B2 | 12/2003 | Stahurski |
| 6,660,037 B1 | 12/2003 | Husson et al. |
| 6,663,647 B2 | 12/2003 | Reiley et al. |
| 6,666,890 B2 | 12/2003 | Michelson |
| 6,666,891 B2 | 12/2003 | Boehm, Jr. et al. |
| 6,669,732 B2 | 12/2003 | Serhan et al. |
| 6,676,663 B2 | 1/2004 | Higueras et al. |
| 6,676,665 B2 | 1/2004 | Foley et al. |
| 6,682,561 B2 | 1/2004 | Songer et al. |
| 6,682,562 B2 | 1/2004 | Viart et al. |
| 6,685,742 B1 | 2/2004 | Jackson |
| 6,689,125 B1 | 2/2004 | Keith et al. |
| 6,689,168 B2 | 2/2004 | Lieberman |
| 6,692,563 B2 | 2/2004 | Zimmermann |
| 6,706,070 B1 | 3/2004 | Wagner et al. |
| 6,716,216 B1 | 4/2004 | Boucher et al. |
| 6,716,247 B2 | 4/2004 | Michelson |
| 6,716,957 B2 | 4/2004 | Tunc |
| 6,719,761 B1 | 4/2004 | Reiley et al. |
| 6,719,773 B1 | 4/2004 | Boucher et al. |
| 6,719,796 B2 | 4/2004 | Cohen et al. |
| 6,723,126 B1 | 4/2004 | Berry |
| 6,723,127 B2 | 4/2004 | Ralph et al. |
| 6,723,128 B2 | 4/2004 | Uk |
| 6,726,691 B2 | 4/2004 | Osorio et al. |
| D490,159 S | 5/2004 | Sand |
| 6,733,532 B1 | 5/2004 | Gauchet et al. |
| 6,740,093 B2 | 5/2004 | Hochschuler et al. |
| 6,740,117 B2 | 5/2004 | Ralph et al. |
| D492,032 S | 6/2004 | Muller et al. |
| 6,743,255 B2 | 6/2004 | Ferree |
| 6,749,560 B1 | 6/2004 | Konstorum et al. |
| 6,755,841 B2 | 6/2004 | Fraser et al. |
| D492,775 S | 7/2004 | Doelling et al. |
| D493,533 S | 7/2004 | Blain |
| 6,758,673 B2 | 7/2004 | Fromovich et al. |
| 6,758,861 B2 | 7/2004 | Ralph et al. |
| 6,764,514 B1 | 7/2004 | Li et al. |
| D495,417 S | 8/2004 | Doelling et al. |
| 6,773,460 B2 | 8/2004 | Jackson |
| 6,780,151 B2 | 8/2004 | Grabover et al. |
| 6,783,530 B1 | 8/2004 | Levy |
| 6,793,678 B2 | 9/2004 | Hawkins |
| 6,793,679 B2 | 9/2004 | Michelson |
| 6,796,983 B1 | 9/2004 | Lucherman et al. |
| 6,805,695 B2 | 10/2004 | Keith et al. |
| 6,805,697 B1 | 10/2004 | Helm et al. |
| 6,805,714 B2 | 10/2004 | Sutcliffe |
| 6,808,537 B2 | 10/2004 | Michelson |
| 6,814,736 B2 | 11/2004 | Reiley et al. |
| 6,814,756 B1 | 11/2004 | Michelson |
| 6,821,298 B1 | 11/2004 | Jackson |
| 6,830,589 B2 | 12/2004 | Erickson |
| 6,835,205 B2 | 12/2004 | Atkinson et al. |
| 6,835,206 B2 | 12/2004 | Jackson |
| 6,835,208 B2 | 12/2004 | Marchosky |
| 6,840,944 B2 | 1/2005 | Suddaby |
| 6,852,126 B2 | 2/2005 | Ahlgren |
| 6,852,129 B2 | 2/2005 | Gerbec et al. |
| 6,855,167 B2 | 2/2005 | Shimp et al. |
| 6,863,668 B2 | 3/2005 | Gillespie et al. |
| 6,863,672 B2 | 3/2005 | Reiley et al. |
| 6,863,673 B2 | 3/2005 | Gerbec et al. |
| 6,866,682 B1 | 3/2005 | An et al. |
| 6,881,228 B2 | 4/2005 | Zdeblick et al. |
| 6,881,229 B2 | 4/2005 | Khandkar et al. |
| 6,883,520 B2 | 4/2005 | Lambrecht et al. |
| 6,887,248 B2 | 5/2005 | McKinley et al. |
| 6,893,464 B2 | 5/2005 | Kiester |
| 6,893,466 B2 | 5/2005 | Trieu |
| 6,899,716 B2 | 5/2005 | Cragg |
| 6,899,719 B2 | 5/2005 | Reiley et al. |
| 6,899,735 B2 | 5/2005 | Coates et al. |
| D506,828 S | 6/2005 | Layne et al. |
| 6,905,512 B2 | 6/2005 | Paes et al. |
| 6,908,506 B2 | 6/2005 | Zimmermann |
| 6,921,403 B2 | 7/2005 | Cragg et al. |
| 6,923,810 B1 | 8/2005 | Michelson |
| 6,923,813 B2 | 8/2005 | Phillips et al. |
| 6,923,814 B1 | 8/2005 | Hildebrand et al. |
| 6,929,647 B2 | 8/2005 | Cohen |
| 6,936,071 B1 | 8/2005 | Marnay et al. |
| 6,945,973 B2 | 9/2005 | Bray |
| 6,952,129 B2 | 10/2005 | Lin et al. |
| 6,953,477 B2 | 10/2005 | Berry |
| 6,955,691 B2 | 10/2005 | Chae et al. |
| 6,962,606 B2 | 11/2005 | Michelson |
| 6,964,674 B1 | 11/2005 | Matsuura et al. |
| 6,964,686 B2 | 11/2005 | Gordon |
| 6,969,404 B2 | 11/2005 | Ferree |
| 6,969,405 B2 | 11/2005 | Suddaby |
| D512,506 S | 12/2005 | Layne et al. |
| 6,972,035 B2 | 12/2005 | Michelson |
| 6,974,479 B2 | 12/2005 | Trieu |
| 6,979,341 B2 | 12/2005 | Scribner et al. |
| 6,979,352 B2 | 12/2005 | Reynolds |
| 6,979,353 B2 | 12/2005 | Bresina |
| 6,981,981 B2 | 1/2006 | Reiley et al. |
| 6,997,929 B2 | 2/2006 | Manzi et al. |
| 7,004,945 B2 | 2/2006 | Boyd et al. |
| 7,008,453 B1 | 3/2006 | Michelson |
| 7,014,633 B2 | 3/2006 | Cragg |
| 7,018,089 B2 | 3/2006 | Wenz et al. |
| 7,018,412 B2 | 3/2006 | Ferreira et al. |
| 7,018,415 B1 | 3/2006 | McKay |
| 7,018,416 B2 | 3/2006 | Hanson et al. |

(56) References Cited

U.S. PATENT DOCUMENTS

| | | |
|---|---|---|
| 7,018,453 B2 | 3/2006 | Klein et al. |
| 7,022,138 B2 | 4/2006 | Mashburn |
| 7,025,787 B2 | 4/2006 | Bryan et al. |
| 7,029,498 B2 | 4/2006 | Boehm et al. |
| 7,037,339 B2 | 5/2006 | Houfburg |
| 7,044,954 B2 | 5/2006 | Reiley et al. |
| 7,048,694 B2 | 5/2006 | Mark et al. |
| 7,063,703 B2 | 6/2006 | Reo |
| 7,066,961 B2 | 6/2006 | Michelson |
| 7,069,087 B2 | 6/2006 | Sharkey et al. |
| 7,070,598 B2 | 7/2006 | Lim et al. |
| 7,074,226 B2 | 7/2006 | Roehm, III et al. |
| 7,081,120 B2 | 7/2006 | Li et al. |
| 7,081,122 B1 | 7/2006 | Reiley et al. |
| 7,083,650 B2 | 8/2006 | Moskowitz et al. |
| 7,087,055 B2 | 8/2006 | Lim et al. |
| 7,094,257 B2 | 8/2006 | Mujwid et al. |
| 7,115,128 B2 | 10/2006 | Michelson |
| 7,115,163 B2 | 10/2006 | Zimmermann |
| 7,118,579 B2 | 10/2006 | Michelson |
| 7,118,580 B1 | 10/2006 | Beyersdorff et al. |
| 7,118,598 B2 | 10/2006 | Michelson |
| 7,124,761 B2 | 10/2006 | Lambrecht et al. |
| 7,128,760 B2 | 10/2006 | Michelson |
| 7,135,424 B2 | 11/2006 | Worley et al. |
| 7,153,304 B2 | 12/2006 | Robie et al. |
| 7,153,305 B2 | 12/2006 | Johnson et al. |
| 7,153,306 B2 | 12/2006 | Ralph et al. |
| 7,153,307 B2 | 12/2006 | Scribner et al. |
| 7,156,874 B2 | 1/2007 | Paponneau et al. |
| 7,156,875 B2 | 1/2007 | Michelson |
| 7,156,876 B2 | 1/2007 | Moumene et al. |
| 7,166,107 B2 | 1/2007 | Anderson |
| 7,179,293 B2 | 2/2007 | McKay |
| 7,189,242 B2 | 3/2007 | Boyd et al. |
| 7,204,851 B2 | 4/2007 | Trieu et al. |
| 7,207,991 B2 | 4/2007 | Michelson |
| 7,211,112 B2 | 5/2007 | Baynham et al. |
| 7,214,227 B2 | 5/2007 | Colleran et al. |
| 7,217,293 B2 | 5/2007 | Branch, Jr. |
| 7,220,280 B2 | 5/2007 | Kast et al. |
| 7,220,281 B2 | 5/2007 | Lambrecht et al. |
| 7,223,227 B2 | 5/2007 | Pflueger |
| 7,223,292 B2 | 5/2007 | Messerli et al. |
| 7,226,481 B2 | 6/2007 | Kuslich |
| 7,226,483 B2 | 6/2007 | Gerber et al. |
| 7,235,101 B2 | 6/2007 | Berry et al. |
| 7,241,297 B2 | 7/2007 | Shaolian et al. |
| 7,244,273 B2 | 7/2007 | Pedersen et al. |
| 7,250,060 B2 | 7/2007 | Trieu |
| 7,252,671 B2 | 8/2007 | Scribner et al. |
| 7,267,687 B2 | 9/2007 | McGuckin, Jr. |
| 7,270,679 B2 | 9/2007 | Istephanous et al. |
| 7,276,062 B2 | 10/2007 | McDaniel et al. |
| 7,291,173 B2 | 11/2007 | Richelsoph et al. |
| 7,311,713 B2 | 12/2007 | Johnson et al. |
| 7,316,714 B2 | 1/2008 | Gordon et al. |
| 7,318,840 B2 | 1/2008 | McKay |
| 7,320,689 B2 | 1/2008 | Keller |
| 7,322,962 B2 | 1/2008 | Forrest |
| 7,326,248 B2 | 2/2008 | Michelson |
| 7,383,639 B2 | 6/2008 | Malandain |
| 7,442,211 B2 | 10/2008 | de Villiers et al. |
| 7,485,134 B2 | 2/2009 | Simonson |
| 7,500,991 B2 | 3/2009 | Bartish, Jr. et al. |
| 7,503,920 B2 | 3/2009 | Siegal |
| 7,503,933 B2 | 3/2009 | Michelson |
| 7,507,241 B2 | 3/2009 | Levy et al. |
| 7,517,363 B2 | 4/2009 | Rogers et al. |
| 7,569,074 B2 | 8/2009 | Eisermann et al. |
| 7,575,599 B2 | 8/2009 | Villiers et al. |
| 7,608,083 B2 | 10/2009 | Lee et al. |
| 7,618,458 B2 | 11/2009 | Biedermann et al. |
| 7,621,950 B1 | 11/2009 | Globerman et al. |
| 7,621,960 B2 | 11/2009 | Boyd et al. |
| 7,637,905 B2 | 12/2009 | Saadat et al. |
| 7,655,010 B2 | 2/2010 | Serhan et al. |
| 7,666,266 B2 | 2/2010 | Izawa et al. |
| 7,670,374 B2 | 3/2010 | Schaller |
| 7,785,368 B2 | 8/2010 | Schaller |
| 7,824,445 B2 | 11/2010 | Biro et al. |
| 7,828,807 B2 | 11/2010 | LeHuec et al. |
| 7,846,206 B2 | 12/2010 | Oglaza et al. |
| 7,854,766 B2 | 12/2010 | Moskowitz et al. |
| 7,874,980 B2 | 1/2011 | Sonnenschein et al. |
| 7,879,098 B1 | 2/2011 | Simmons, Jr. |
| 7,887,589 B2 | 2/2011 | Glenn et al. |
| 7,909,870 B2 | 3/2011 | Kraus |
| 7,918,874 B2 | 4/2011 | Siegal |
| 7,922,729 B2 | 4/2011 | Michelson |
| 7,935,051 B2 | 5/2011 | Miles et al. |
| 7,942,903 B2 | 5/2011 | Moskowitz et al. |
| 7,947,078 B2 | 5/2011 | Siegal |
| 7,951,199 B2 | 5/2011 | Miller |
| 7,955,391 B2 | 6/2011 | Schaller |
| 7,959,675 B2 | 6/2011 | Gately |
| 7,963,993 B2 | 6/2011 | Schaller |
| 7,967,864 B2 | 6/2011 | Schaller |
| 7,967,865 B2 | 6/2011 | Schaller |
| 7,985,231 B2 | 7/2011 | Sankaran |
| 7,993,403 B2 | 8/2011 | Foley et al. |
| 8,007,535 B2 | 8/2011 | Hudgins et al. |
| 8,021,424 B2 | 9/2011 | Beger et al. |
| 8,021,426 B2 | 9/2011 | Segal et al. |
| 8,025,697 B2 | 9/2011 | McClellan et al. |
| 8,034,109 B2 | 10/2011 | Zwirkoski |
| 8,043,381 B2 | 10/2011 | Hestad et al. |
| 8,052,754 B2 | 11/2011 | Froehlich |
| 8,057,544 B2 | 11/2011 | Schaller |
| 8,057,545 B2 | 11/2011 | Hughes et al. |
| 8,062,375 B2 | 11/2011 | Glerum et al. |
| 8,075,621 B2 | 12/2011 | Michelson |
| 8,097,036 B2 | 1/2012 | Cordaro et al. |
| 8,177,812 B2 | 5/2012 | Sankaran |
| 8,187,327 B2 | 5/2012 | Edidin et al. |
| 8,192,495 B2 | 6/2012 | Simpson et al. |
| 8,202,322 B2 | 6/2012 | Doty |
| 8,206,423 B2 | 6/2012 | Siegal |
| 8,216,312 B2 | 7/2012 | Gray |
| 8,216,314 B2 | 7/2012 | Richelsoph |
| 8,221,501 B2 | 7/2012 | Eisermann et al. |
| 8,221,502 B2 | 7/2012 | Branch, Jr. |
| 8,221,503 B2 | 7/2012 | Garcia et al. |
| 8,231,681 B2 | 7/2012 | Castleman et al. |
| 8,236,029 B2 | 8/2012 | Siegal |
| 8,236,058 B2 | 8/2012 | Fabian et al. |
| 8,241,328 B2 | 8/2012 | Siegal |
| 8,241,358 B2 | 8/2012 | Butler et al. |
| 8,241,361 B2 | 8/2012 | Link |
| 8,246,622 B2 | 8/2012 | Siegal et al. |
| 8,257,442 B2 | 9/2012 | Edie et al. |
| 8,262,666 B2 | 9/2012 | Baynham et al. |
| 8,267,939 B2 | 9/2012 | Cipoletti et al. |
| 8,267,965 B2 | 9/2012 | Gimbel et al. |
| 8,273,128 B2 | 9/2012 | Oh et al. |
| 8,287,599 B2 | 10/2012 | McGuckin, Jr. |
| 8,292,959 B2 | 10/2012 | Webb et al. |
| 8,303,663 B2 | 11/2012 | Jimenez et al. |
| 8,323,345 B2 | 12/2012 | Sledge |
| 8,328,812 B2 | 12/2012 | Siegal et al. |
| 8,328,852 B2 | 12/2012 | Lehavi et al. |
| 8,337,559 B2 | 12/2012 | Hansell et al. |
| 8,343,193 B2 | 1/2013 | Johnson et al. |
| 8,353,961 B2 | 1/2013 | McClintock et al. |
| 8,361,154 B2 | 1/2013 | Reo |
| 8,377,098 B2 | 2/2013 | Landry et al. |
| 8,382,842 B2 | 2/2013 | Greenhalgh et al. |
| 8,398,712 B2 | 3/2013 | de Villiers et al. |
| 8,398,713 B2 | 3/2013 | Weiman |
| 8,403,990 B2 | 3/2013 | Dryer et al. |
| 8,409,290 B2 | 4/2013 | Zamani et al. |
| 8,409,291 B2 | 4/2013 | Blackwell et al. |
| 8,414,650 B2 | 4/2013 | Bertele et al. |
| 8,435,298 B2 | 5/2013 | Weiman |

(56) References Cited

U.S. PATENT DOCUMENTS

| | | |
|---|---|---|
| 8,454,617 B2 | 6/2013 | Schaller et al. |
| 8,454,698 B2 | 6/2013 | de Villiers et al. |
| 8,465,524 B2 | 6/2013 | Siegal |
| 8,480,715 B2 | 7/2013 | Gray |
| 8,480,742 B2 | 7/2013 | Pisharodi |
| 8,486,109 B2 | 7/2013 | Siegal |
| 8,486,148 B2 | 7/2013 | Butler et al. |
| 8,491,591 B2 | 7/2013 | Fuerderer |
| 8,491,659 B2 | 7/2013 | Weiman |
| 8,506,635 B2 | 8/2013 | Palmatier et al. |
| 8,518,087 B2 | 8/2013 | Lopez et al. |
| 8,518,120 B2 | 8/2013 | Glerum et al. |
| 8,545,567 B1 | 10/2013 | Krueger |
| 8,551,173 B2 | 10/2013 | Lechmann et al. |
| 8,556,978 B2 | 10/2013 | Schaller |
| 8,556,979 B2 | 10/2013 | Glerum et al. |
| 8,568,481 B2 | 10/2013 | Olmos et al. |
| 8,579,977 B2 | 11/2013 | Fabian |
| 8,579,981 B2 | 11/2013 | Lim et al. |
| 8,591,583 B2 | 11/2013 | Schaller et al. |
| 8,591,585 B2 | 11/2013 | McLaughlin et al. |
| 8,597,330 B2 | 12/2013 | Siegal |
| 8,603,168 B2 | 12/2013 | Gordon et al. |
| 8,603,177 B2 | 12/2013 | Gray |
| 8,628,576 B2 | 1/2014 | Triplett et al. |
| 8,628,578 B2 | 1/2014 | Miller et al. |
| 8,632,595 B2 | 1/2014 | Weiman |
| 8,641,764 B2 | 2/2014 | Gately |
| 8,663,329 B2 | 3/2014 | Ernst |
| 8,668,740 B2 | 3/2014 | Rhoda et al. |
| 8,672,977 B2 | 3/2014 | Siegal et al. |
| 8,679,183 B2 | 3/2014 | Glerum et al. |
| 8,685,095 B2 | 4/2014 | Miller et al. |
| 8,685,098 B2 | 4/2014 | Glerum et al. |
| 8,696,751 B2 | 4/2014 | Ashley et al. |
| 8,709,086 B2 | 4/2014 | Glerum |
| 8,715,351 B1 | 5/2014 | Pinto |
| 8,721,723 B2 | 5/2014 | Hansell et al. |
| 8,728,166 B2 | 5/2014 | Schwab |
| 8,753,398 B2 | 6/2014 | Gordon et al. |
| 8,758,441 B2 | 6/2014 | Hovda et al. |
| 8,764,806 B2 | 7/2014 | Abdou |
| 8,771,360 B2 | 7/2014 | Jimenez et al. |
| 8,777,993 B2 | 7/2014 | Siegal et al. |
| 8,778,025 B2 | 7/2014 | Ragab et al. |
| 8,795,366 B2 | 8/2014 | Varela |
| 8,795,374 B2 | 8/2014 | Chee |
| 8,801,787 B2 | 8/2014 | Schaller |
| 8,801,792 B2 | 8/2014 | de Villiers et al. |
| 8,808,376 B2 | 8/2014 | Schaller |
| 8,828,085 B1 | 9/2014 | Jensen |
| 8,845,638 B2 | 9/2014 | Siegal et al. |
| 8,845,728 B1 | 9/2014 | Abdou |
| 8,845,731 B2 | 9/2014 | Weiman |
| 8,845,732 B2 | 9/2014 | Weiman |
| 8,845,734 B2 | 9/2014 | Weiman |
| 8,852,279 B2 | 10/2014 | Weiman |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,900,235 B2 | 12/2014 | Siegal |
| 8,900,307 B2 | 12/2014 | Hawkins et al. |
| 8,906,098 B2 | 12/2014 | Siegal |
| 8,926,704 B2 | 1/2015 | Glerum et al. |
| 8,936,641 B2 | 1/2015 | Cain |
| 8,940,052 B2 | 1/2015 | Lechmann et al. |
| 8,961,609 B2 | 2/2015 | Schaller |
| 8,979,929 B2 | 3/2015 | Schaller |
| 8,986,388 B2 | 3/2015 | Siegal et al. |
| 9,017,408 B2 | 4/2015 | Siegal et al. |
| 9,017,413 B2 | 4/2015 | Siegal et al. |
| 9,044,334 B2 | 6/2015 | Siegal et al. |
| 9,044,338 B2 | 6/2015 | Schaller |
| 9,066,808 B2 | 6/2015 | Schaller |
| 9,089,428 B2 | 7/2015 | Bertele et al. |
| 9,095,446 B2 | 8/2015 | Landry et al. |
| 9,095,447 B2 | 8/2015 | Barreiro et al. |
| 9,254,138 B2 | 2/2016 | Siegal et al. |
| 9,259,326 B2 | 2/2016 | Schaller |
| 9,283,092 B2 | 3/2016 | Siegal et al. |
| 9,326,866 B2 | 5/2016 | Schaller et al. |
| 9,333,091 B2 | 5/2016 | DiMauro |
| 9,387,087 B2 | 7/2016 | Tyber |
| 9,408,712 B2 | 8/2016 | Siegal et al. |
| 9,414,923 B2 | 8/2016 | Studer et al. |
| 9,439,776 B2 | 9/2016 | DiMauro et al. |
| 9,439,777 B2 | 9/2016 | DiMauro |
| 9,724,207 B2 | 8/2017 | DiMauro et al. |
| 9,730,803 B2 | 8/2017 | DiMauro et al. |
| 2001/0011174 A1 | 8/2001 | Reiley et al. |
| 2001/0016741 A1 | 8/2001 | Burkus et al. |
| 2001/0039452 A1 | 11/2001 | Zucherman et al. |
| 2001/0039453 A1 | 11/2001 | Gresser et al. |
| 2001/0049531 A1 | 12/2001 | Reiley et al. |
| 2001/0056302 A1 | 12/2001 | Boyer et al. |
| 2002/0010070 A1 | 1/2002 | Cales et al. |
| 2002/0016583 A1 | 2/2002 | Cragg |
| 2002/0026195 A1 | 2/2002 | Layne et al. |
| 2002/0026244 A1 | 2/2002 | Trieu |
| 2002/0029084 A1 | 3/2002 | Paul et al. |
| 2002/0035400 A1 | 3/2002 | Bryan et al. |
| 2002/0037799 A1 | 3/2002 | Li et al. |
| 2002/0045904 A1 | 4/2002 | Fuss et al. |
| 2002/0045942 A1 | 4/2002 | Ham |
| 2002/0055781 A1 | 5/2002 | Sazy |
| 2002/0058947 A1 | 5/2002 | Hochschuler et al. |
| 2002/0068974 A1 | 6/2002 | Kuslich et al. |
| 2002/0068976 A1 | 6/2002 | Jackson |
| 2002/0068977 A1 | 6/2002 | Jackson |
| 2002/0077700 A1 | 6/2002 | Varga et al. |
| 2002/0077701 A1 | 6/2002 | Kuslich |
| 2002/0082584 A1 | 6/2002 | Rosenman et al. |
| 2002/0082608 A1 | 6/2002 | Reiley et al. |
| 2002/0087163 A1 | 7/2002 | Dixon et al. |
| 2002/0091390 A1 | 7/2002 | Michelson |
| 2002/0099385 A1 | 7/2002 | Ralph et al. |
| 2002/0107519 A1 | 8/2002 | Dixon et al. |
| 2002/0107573 A1 | 8/2002 | Steinberg |
| 2002/0128715 A1 | 9/2002 | Bryan et al. |
| 2002/0128716 A1 | 9/2002 | Cohen et al. |
| 2002/0151976 A1 | 10/2002 | Foley et al. |
| 2002/0156482 A1 | 10/2002 | Scribner et al. |
| 2002/0165612 A1 | 11/2002 | Gerber et al. |
| 2002/0169471 A1 | 11/2002 | Ferdinand |
| 2002/0172851 A1 | 11/2002 | Corey et al. |
| 2002/0173796 A1 | 11/2002 | Cragg |
| 2002/0173841 A1 | 11/2002 | Ortiz et al. |
| 2002/0173851 A1 | 11/2002 | McKay |
| 2002/0183761 A1 | 12/2002 | Johnson et al. |
| 2002/0183778 A1 | 12/2002 | Reiley et al. |
| 2002/0191487 A1 | 12/2002 | Sand |
| 2002/0193883 A1 | 12/2002 | Wironen |
| 2002/0198526 A1 | 12/2002 | Shaolian et al. |
| 2003/0004575 A1 | 1/2003 | Erickson |
| 2003/0004576 A1 | 1/2003 | Thalgott |
| 2003/0006942 A1 | 1/2003 | Searls et al. |
| 2003/0014112 A1 | 1/2003 | Ralph et al. |
| 2003/0014116 A1 | 1/2003 | Ralph et al. |
| 2003/0018390 A1 | 1/2003 | Husson |
| 2003/0023305 A1 | 1/2003 | McKay |
| 2003/0028251 A1 | 2/2003 | Mathews |
| 2003/0032963 A1 | 2/2003 | Reiss et al. |
| 2003/0040796 A1 | 2/2003 | Ferree |
| 2003/0040799 A1 | 2/2003 | Boyd et al. |
| 2003/0045937 A1 | 3/2003 | Ginn |
| 2003/0045939 A1 | 3/2003 | Casutt |
| 2003/0050644 A1 | 3/2003 | Boucher et al. |
| 2003/0065396 A1 | 4/2003 | Michelson |
| 2003/0069593 A1 | 4/2003 | Tremulis et al. |
| 2003/0069642 A1 | 4/2003 | Ralph et al. |
| 2003/0073998 A1 | 4/2003 | Pagliuca et al. |
| 2003/0074075 A1 | 4/2003 | Thomas et al. |
| 2003/0078667 A1 | 4/2003 | Manasas et al. |
| 2003/0083642 A1 | 5/2003 | Boyd et al. |

(56) References Cited

U.S. PATENT DOCUMENTS

| | | |
|---|---|---|
| 2003/0108588 A1 | 6/2003 | Chen et al. |
| 2003/0130664 A1 | 7/2003 | Boucher et al. |
| 2003/0130739 A1 | 7/2003 | Gerbec et al. |
| 2003/0135275 A1 | 7/2003 | Garcia et al. |
| 2003/0139812 A1 | 7/2003 | Garcia et al. |
| 2003/0139813 A1 | 7/2003 | Messerli et al. |
| 2003/0171812 A1 | 9/2003 | Grunberg et al. |
| 2003/0187445 A1 | 10/2003 | Keith et al. |
| 2003/0187506 A1 | 10/2003 | Ross et al. |
| 2003/0191414 A1 | 10/2003 | Reiley et al. |
| 2003/0191489 A1 | 10/2003 | Reiley et al. |
| 2003/0195518 A1 | 10/2003 | Cragg |
| 2003/0195547 A1 | 10/2003 | Scribner et al. |
| 2003/0195630 A1 | 10/2003 | Ferree |
| 2003/0199979 A1 | 10/2003 | McGuckin |
| 2003/0204261 A1 | 10/2003 | Eisermann et al. |
| 2003/0208136 A1 | 11/2003 | Mark et al. |
| 2003/0220648 A1 | 11/2003 | Osorio et al. |
| 2003/0220695 A1 | 11/2003 | Sevrain |
| 2003/0229372 A1 | 12/2003 | Reiley et al. |
| 2003/0233096 A1 | 12/2003 | Osorio et al. |
| 2003/0233145 A1 | 12/2003 | Landry et al. |
| 2003/0233146 A1 | 12/2003 | Grinberg et al. |
| 2004/0002761 A1 | 1/2004 | Rogers et al. |
| 2004/0010251 A1 | 1/2004 | Pitaru et al. |
| 2004/0010260 A1 | 1/2004 | Scribner et al. |
| 2004/0010263 A1 | 1/2004 | Boucher et al. |
| 2004/0010318 A1 | 1/2004 | Ferree |
| 2004/0019354 A1 | 1/2004 | Johnson et al. |
| 2004/0024408 A1 | 2/2004 | Burkus et al. |
| 2004/0024409 A1 | 2/2004 | Sand et al. |
| 2004/0024463 A1 | 2/2004 | Thomas et al. |
| 2004/0024465 A1 | 2/2004 | Lambrecht et al. |
| 2004/0030387 A1 | 2/2004 | Landry et al. |
| 2004/0034343 A1 | 2/2004 | Gillespie et al. |
| 2004/0034429 A1 | 2/2004 | Lambrecht et al. |
| 2004/0049203 A1 | 3/2004 | Scribner et al. |
| 2004/0049270 A1 | 3/2004 | Gewirtz |
| 2004/0059333 A1 | 3/2004 | Carl et al. |
| 2004/0059339 A1 | 3/2004 | Roehm et al. |
| 2004/0059418 A1 | 3/2004 | McKay et al. |
| 2004/0064144 A1 | 4/2004 | Johnson et al. |
| 2004/0073308 A1 | 4/2004 | Kuslich et al. |
| 2004/0073310 A1 | 4/2004 | Moumene et al. |
| 2004/0082953 A1 | 4/2004 | Petit |
| 2004/0087947 A1 | 5/2004 | Lim et al. |
| 2004/0088055 A1 | 5/2004 | Hanson et al. |
| 2004/0092933 A1 | 5/2004 | Shaolian et al. |
| 2004/0092948 A1 | 5/2004 | Stevens et al. |
| 2004/0092988 A1 | 5/2004 | Shaolian et al. |
| 2004/0097924 A1 | 5/2004 | Lambrecht et al. |
| 2004/0097930 A1 | 5/2004 | Justis et al. |
| 2004/0097932 A1 | 5/2004 | Ray et al. |
| 2004/0098131 A1 | 5/2004 | Bryan et al. |
| 2004/0102774 A1 | 5/2004 | Trieu |
| 2004/0106940 A1 | 6/2004 | Shaolian et al. |
| 2004/0111161 A1 | 6/2004 | Trieu |
| 2004/0116997 A1 | 6/2004 | Taylor et al. |
| 2004/0117019 A1 | 6/2004 | Trieu et al. |
| 2004/0117022 A1 | 6/2004 | Marnay et al. |
| 2004/0127990 A1 | 7/2004 | Bartish et al. |
| 2004/0127991 A1 | 7/2004 | Ferree |
| 2004/0133124 A1 | 7/2004 | Bates et al. |
| 2004/0133229 A1 | 7/2004 | Lambrecht et al. |
| 2004/0133280 A1 | 7/2004 | Trieu |
| 2004/0138748 A1 | 7/2004 | Boyer et al. |
| 2004/0143332 A1 | 7/2004 | Krueger et al. |
| 2004/0153064 A1 | 8/2004 | Foley et al. |
| 2004/0153065 A1 | 8/2004 | Lim |
| 2004/0153115 A1 | 8/2004 | Reiley et al. |
| 2004/0153156 A1 | 8/2004 | Cohen et al. |
| 2004/0158206 A1 | 8/2004 | Aboul-Hosn et al. |
| 2004/0162618 A1 | 8/2004 | Mujwid et al. |
| 2004/0167561 A1 | 8/2004 | Boucher et al. |
| 2004/0167562 A1 | 8/2004 | Osorio et al. |
| 2004/0167625 A1 | 8/2004 | Beyar et al. |
| 2004/0172133 A1 | 9/2004 | Gerber et al. |
| 2004/0176775 A1 | 9/2004 | Burkus et al. |
| 2004/0186052 A1 | 9/2004 | Iyer et al. |
| 2004/0186471 A1 | 9/2004 | Trieu |
| 2004/0186528 A1 | 9/2004 | Ries et al. |
| 2004/0186570 A1 | 9/2004 | Rapp |
| 2004/0186573 A1 | 9/2004 | Ferree |
| 2004/0186577 A1 | 9/2004 | Ferree |
| 2004/0193277 A1 | 9/2004 | Long et al. |
| 2004/0210231 A1 | 10/2004 | Boucher et al. |
| 2004/0210310 A1 | 10/2004 | Trieu |
| 2004/0215344 A1 | 10/2004 | Hochschuler et al. |
| 2004/0220580 A1 | 11/2004 | Johnson et al. |
| 2004/0220669 A1 | 11/2004 | Studer |
| 2004/0220672 A1 | 11/2004 | Shadduck |
| 2004/0225296 A1 | 11/2004 | Reiss et al. |
| 2004/0225361 A1 | 11/2004 | Glenn et al. |
| 2004/0230191 A1 | 11/2004 | Frey et al. |
| 2004/0230309 A1 | 11/2004 | DiMauro et al. |
| 2004/0243229 A1 | 12/2004 | Vidlund et al. |
| 2004/0243241 A1 | 12/2004 | Istephanous et al. |
| 2004/0249377 A1 | 12/2004 | Kaes et al. |
| 2004/0254520 A1 | 12/2004 | Porteous et al. |
| 2004/0254644 A1 | 12/2004 | Taylor |
| 2004/0260300 A1 | 12/2004 | Gorensek et al. |
| 2004/0260397 A1 | 12/2004 | Lambrecht et al. |
| 2004/0267271 A9 | 12/2004 | Scribner et al. |
| 2004/0267367 A1 | 12/2004 | O'Oneil |
| 2005/0004578 A1 | 1/2005 | Lambrecht et al. |
| 2005/0010293 A1 | 1/2005 | Zucherman et al. |
| 2005/0010298 A1 | 1/2005 | Zucherman et al. |
| 2005/0015148 A1 | 1/2005 | Jansen et al. |
| 2005/0015152 A1 | 1/2005 | Sweeney |
| 2005/0019365 A1 | 1/2005 | Frauchiger et al. |
| 2005/0021041 A1 | 1/2005 | Michelson |
| 2005/0033295 A1 | 2/2005 | Wisnewski |
| 2005/0033440 A1 | 2/2005 | Lambrecht et al. |
| 2005/0038515 A1 | 2/2005 | Kunzler |
| 2005/0038517 A1 | 2/2005 | Garrison et al. |
| 2005/0043737 A1 | 2/2005 | Reiley et al. |
| 2005/0043796 A1 | 2/2005 | Grant et al. |
| 2005/0054948 A1 | 3/2005 | Goldenberg |
| 2005/0055097 A1 | 3/2005 | Grunberg et al. |
| 2005/0060036 A1 | 3/2005 | Schultz et al. |
| 2005/0060038 A1 | 3/2005 | Lambrecht et al. |
| 2005/0065519 A1 | 3/2005 | Michelson |
| 2005/0065609 A1 | 3/2005 | Wardlaw |
| 2005/0069571 A1 | 3/2005 | Slivka et al. |
| 2005/0070908 A1 | 3/2005 | Cragg |
| 2005/0070911 A1 | 3/2005 | Garrison et al. |
| 2005/0070913 A1 | 3/2005 | Milbocker et al. |
| 2005/0071011 A1 | 3/2005 | Ralph et al. |
| 2005/0080488 A1 | 4/2005 | Schultz |
| 2005/0085912 A1 | 4/2005 | Amin et al. |
| 2005/0090833 A1 | 4/2005 | DiPoto |
| 2005/0090852 A1 | 4/2005 | Layne et al. |
| 2005/0090899 A1 | 4/2005 | DiPoto |
| 2005/0107880 A1 | 5/2005 | Shimp et al. |
| 2005/0113916 A1 | 5/2005 | Branch |
| 2005/0113917 A1 | 5/2005 | Chae et al. |
| 2005/0113918 A1 | 5/2005 | Messerli et al. |
| 2005/0113919 A1 | 5/2005 | Cragg et al. |
| 2005/0113928 A1 | 5/2005 | Cragg et al. |
| 2005/0118228 A1 | 6/2005 | Trieu |
| 2005/0119662 A1 | 6/2005 | Reiley et al. |
| 2005/0119750 A1 | 6/2005 | Studer |
| 2005/0119751 A1 | 6/2005 | Lawson |
| 2005/0119752 A1 | 6/2005 | Williams et al. |
| 2005/0119754 A1 | 6/2005 | Trieu et al. |
| 2005/0124989 A1 | 6/2005 | Suddaby |
| 2005/0124992 A1 | 6/2005 | Ferree |
| 2005/0124999 A1 | 6/2005 | Teitelbaum et al. |
| 2005/0125062 A1 | 6/2005 | Biedermann et al. |
| 2005/0125066 A1 | 6/2005 | McAfee |
| 2005/0131267 A1 | 6/2005 | Talmadge |
| 2005/0131268 A1 | 6/2005 | Talmadge |
| 2005/0131269 A1 | 6/2005 | Talmadge |
| 2005/0131536 A1 | 6/2005 | Eisermann et al. |

(56) References Cited

U.S. PATENT DOCUMENTS

| | | |
|---|---|---|
| 2005/0131540 A1 | 6/2005 | Trieu |
| 2005/0131541 A1 | 6/2005 | Trieu |
| 2005/0137602 A1 | 6/2005 | Assell et al. |
| 2005/0142211 A1 | 6/2005 | Wenz |
| 2005/0143763 A1 | 6/2005 | Ortiz et al. |
| 2005/0143827 A1 | 6/2005 | Globerman et al. |
| 2005/0149022 A1 | 7/2005 | Shaolian et al. |
| 2005/0149191 A1 | 7/2005 | Cragg et al. |
| 2005/0149194 A1 | 7/2005 | Ahlgren |
| 2005/0149197 A1 | 7/2005 | Cauthen |
| 2005/0154396 A1 | 7/2005 | Foley et al. |
| 2005/0154463 A1 | 7/2005 | Trieu |
| 2005/0165406 A1 | 7/2005 | Assell et al. |
| 2005/0165485 A1 | 7/2005 | Trieu |
| 2005/0171539 A1 | 8/2005 | Braun et al. |
| 2005/0171552 A1 | 8/2005 | Johnson et al. |
| 2005/0182412 A1 | 8/2005 | Johnson et al. |
| 2005/0182413 A1 | 8/2005 | Johnson et al. |
| 2005/0182414 A1 | 8/2005 | Manzi et al. |
| 2005/0187556 A1 | 8/2005 | Stack et al. |
| 2005/0187558 A1 | 8/2005 | Johnson et al. |
| 2005/0187559 A1 | 8/2005 | Raymond et al. |
| 2005/0187564 A1 | 8/2005 | Jayaraman |
| 2005/0197702 A1 | 9/2005 | Coppes et al. |
| 2005/0197707 A1 | 9/2005 | Trieu et al. |
| 2005/0216018 A1 | 9/2005 | Sennett |
| 2005/0216087 A1 | 9/2005 | Zucherman et al. |
| 2005/0222681 A1 | 10/2005 | Richley et al. |
| 2005/0222684 A1 | 10/2005 | Ferree |
| 2005/0228383 A1 | 10/2005 | Zucherman et al. |
| 2005/0228391 A1 | 10/2005 | Levy et al. |
| 2005/0228397 A1 | 10/2005 | Malandain et al. |
| 2005/0234425 A1 | 10/2005 | Miller et al. |
| 2005/0234451 A1 | 10/2005 | Markworth |
| 2005/0234452 A1 | 10/2005 | Malandain |
| 2005/0234456 A1 | 10/2005 | Malandain |
| 2005/0240182 A1 | 10/2005 | Zucherman et al. |
| 2005/0240189 A1 | 10/2005 | Rousseau et al. |
| 2005/0240193 A1 | 10/2005 | Layne et al. |
| 2005/0240269 A1 | 10/2005 | Lambrecht et al. |
| 2005/0251149 A1 | 11/2005 | Wenz |
| 2005/0251260 A1 | 11/2005 | Gerber et al. |
| 2005/0256576 A1 | 11/2005 | Moskowitz et al. |
| 2005/0261682 A1 | 11/2005 | Ferree |
| 2005/0261684 A1 | 11/2005 | Shaolian et al. |
| 2005/0261695 A1 | 11/2005 | Cragg et al. |
| 2005/0261769 A1 | 11/2005 | Moskowitz et al. |
| 2005/0261781 A1 | 11/2005 | Sennett et al. |
| 2005/0267471 A1 | 12/2005 | Biedermann et al. |
| 2005/0273166 A1 | 12/2005 | Sweeney |
| 2005/0273173 A1 | 12/2005 | Gordon et al. |
| 2005/0278023 A1 | 12/2005 | Zwirkoski |
| 2005/0278026 A1 | 12/2005 | Gordon et al. |
| 2005/0278027 A1 | 12/2005 | Hyde |
| 2005/0278029 A1 | 12/2005 | Trieu |
| 2005/0283244 A1 | 12/2005 | Gordon et al. |
| 2005/0287071 A1 | 12/2005 | Wenz |
| 2006/0004456 A1 | 1/2006 | McKay |
| 2006/0009779 A1 | 1/2006 | Collins et al. |
| 2006/0015119 A1 | 1/2006 | Plassky et al. |
| 2006/0030850 A1 | 2/2006 | Keegan et al. |
| 2006/0030933 A1 | 2/2006 | DeLegge et al. |
| 2006/0030943 A1 | 2/2006 | Peterman |
| 2006/0036241 A1 | 2/2006 | Siegal |
| 2006/0036259 A1 | 2/2006 | Carl et al. |
| 2006/0036261 A1 | 2/2006 | McDonnell |
| 2006/0036273 A1 | 2/2006 | Siegal |
| 2006/0041258 A1 | 2/2006 | Galea |
| 2006/0045904 A1 | 3/2006 | Aronson |
| 2006/0058807 A1 | 3/2006 | Landry et al. |
| 2006/0058876 A1 | 3/2006 | McKinley |
| 2006/0058880 A1 | 3/2006 | Wysocki et al. |
| 2006/0064171 A1 | 3/2006 | Trieu |
| 2006/0064172 A1 | 3/2006 | Trieu |
| 2006/0069439 A1 | 3/2006 | Zucherman et al. |
| 2006/0069440 A1 | 3/2006 | Zucherman et al. |
| 2006/0084867 A1 | 4/2006 | Tremblay et al. |
| 2006/0085002 A1 | 4/2006 | Trieu et al. |
| 2006/0085009 A1 | 4/2006 | Truckai et al. |
| 2006/0089642 A1 | 4/2006 | Diaz et al. |
| 2006/0089646 A1 | 4/2006 | Bonutti |
| 2006/0089654 A1 | 4/2006 | Lins et al. |
| 2006/0089715 A1 | 4/2006 | Truckai et al. |
| 2006/0089718 A1 | 4/2006 | Zucherman et al. |
| 2006/0089719 A1 | 4/2006 | Trieu |
| 2006/0095045 A1 | 5/2006 | Trieu |
| 2006/0095046 A1 | 5/2006 | Trieu et al. |
| 2006/0095134 A1 | 5/2006 | Trieu et al. |
| 2006/0095138 A1 | 5/2006 | Truckai et al. |
| 2006/0100706 A1 | 5/2006 | Shadduck et al. |
| 2006/0106397 A1 | 5/2006 | Lins |
| 2006/0106459 A1 | 5/2006 | Truckai et al. |
| 2006/0111785 A1 | 5/2006 | O'neil |
| 2006/0122701 A1 | 6/2006 | Kiester |
| 2006/0122703 A1 | 6/2006 | Aebi et al. |
| 2006/0122704 A1 | 6/2006 | Vresilovic et al. |
| 2006/0129244 A1 | 6/2006 | Ensign |
| 2006/0136062 A1 | 6/2006 | DiNello et al. |
| 2006/0136064 A1 | 6/2006 | Sherman |
| 2006/0142858 A1 | 6/2006 | Colleran et al. |
| 2006/0142864 A1 | 6/2006 | Cauthen |
| 2006/0149136 A1 | 7/2006 | Seto et al. |
| 2006/0149237 A1 | 7/2006 | Markworth et al. |
| 2006/0149252 A1 | 7/2006 | Markworth et al. |
| 2006/0149379 A1 | 7/2006 | Kuslich et al. |
| 2006/0149380 A1 | 7/2006 | Lotz et al. |
| 2006/0155379 A1 | 7/2006 | Heneveld et al. |
| 2006/0161162 A1 | 7/2006 | Lambrecht et al. |
| 2006/0161166 A1 | 7/2006 | Johnson et al. |
| 2006/0167553 A1 | 7/2006 | Cauthen et al. |
| 2006/0173545 A1 | 8/2006 | Cauthen et al. |
| 2006/0178746 A1 | 8/2006 | Bartish et al. |
| 2006/0184192 A1 | 8/2006 | Markworth et al. |
| 2006/0184247 A1 | 8/2006 | Edidin et al. |
| 2006/0184248 A1 | 8/2006 | Edidin et al. |
| 2006/0189999 A1 | 8/2006 | Zwirkoski |
| 2006/0190083 A1 | 8/2006 | Amin et al. |
| 2006/0190085 A1 | 8/2006 | Cauthen |
| 2006/0195102 A1 | 8/2006 | Malandain |
| 2006/0195191 A1 | 8/2006 | Sweeney et al. |
| 2006/0200139 A1 | 9/2006 | Michelson |
| 2006/0200164 A1 | 9/2006 | Michelson |
| 2006/0200239 A1 | 9/2006 | Rothman et al. |
| 2006/0200240 A1 | 9/2006 | Rothman et al. |
| 2006/0200241 A1 | 9/2006 | Rothman et al. |
| 2006/0200242 A1 | 9/2006 | Rothman et al. |
| 2006/0200243 A1 | 9/2006 | Rothman et al. |
| 2006/0206116 A1 | 9/2006 | Yeung |
| 2006/0206207 A1 | 9/2006 | Dryer et al. |
| 2006/0235423 A1 | 10/2006 | Cantu |
| 2006/0235521 A1 | 10/2006 | Zucherman et al. |
| 2006/0235531 A1 | 10/2006 | Buettner-Janz |
| 2006/0241663 A1 | 10/2006 | Rice et al. |
| 2006/0241770 A1 | 10/2006 | Rhoda et al. |
| 2006/0247770 A1 | 11/2006 | Peterman |
| 2006/0247771 A1 | 11/2006 | Peterman et al. |
| 2006/0247781 A1 | 11/2006 | Francis |
| 2006/0253201 A1 | 11/2006 | McLuen |
| 2006/0264896 A1 | 11/2006 | Palmer |
| 2006/0264939 A1 | 11/2006 | Zucherman et al. |
| 2006/0264945 A1 | 11/2006 | Edidin et al. |
| 2006/0265067 A1 | 11/2006 | Zucherman et al. |
| 2006/0265075 A1 | 11/2006 | Baumgartner et al. |
| 2006/0265077 A1 | 11/2006 | Zwirkoski |
| 2006/0271049 A1 | 11/2006 | Zucherman et al. |
| 2006/0271061 A1 | 11/2006 | Beyar et al. |
| 2006/0276897 A1 | 12/2006 | Winslow et al. |
| 2006/0276899 A1 | 12/2006 | Zipnick et al. |
| 2006/0282167 A1 | 12/2006 | Lambrecht et al. |
| 2006/0287726 A1 | 12/2006 | Segal et al. |
| 2006/0287727 A1 | 12/2006 | Segal et al. |
| 2006/0293662 A1 | 12/2006 | Boyer et al. |
| 2006/0293753 A1 | 12/2006 | Thramann |
| 2007/0006692 A1 | 1/2007 | Phan |

(56) References Cited

U.S. PATENT DOCUMENTS

| | | |
|---|---|---|
| 2007/0010716 A1 | 1/2007 | Malandain et al. |
| 2007/0010717 A1 | 1/2007 | Cragg |
| 2007/0010824 A1 | 1/2007 | Malandain et al. |
| 2007/0010844 A1 | 1/2007 | Gong et al. |
| 2007/0010845 A1 | 1/2007 | Gong et al. |
| 2007/0010846 A1 | 1/2007 | Leung et al. |
| 2007/0010848 A1 | 1/2007 | Leung et al. |
| 2007/0010886 A1 | 1/2007 | Banick et al. |
| 2007/0010889 A1 | 1/2007 | Francis |
| 2007/0032703 A1 | 2/2007 | Sankaran et al. |
| 2007/0032791 A1 | 2/2007 | Greenhalgh |
| 2007/0043361 A1 | 2/2007 | Malandain et al. |
| 2007/0043362 A1 | 2/2007 | Malandain et al. |
| 2007/0043363 A1 | 2/2007 | Malandain et al. |
| 2007/0043440 A1 | 2/2007 | William et al. |
| 2007/0048382 A1 | 3/2007 | Meyer et al. |
| 2007/0049849 A1 | 3/2007 | Schwardt et al. |
| 2007/0049934 A1 | 3/2007 | Edidin et al. |
| 2007/0049935 A1 | 3/2007 | Edidin et al. |
| 2007/0050034 A1 | 3/2007 | Schwardt et al. |
| 2007/0050035 A1 | 3/2007 | Schwardt et al. |
| 2007/0055201 A1 | 3/2007 | Seto et al. |
| 2007/0055237 A1 | 3/2007 | Edidin et al. |
| 2007/0055246 A1 | 3/2007 | Zucherman et al. |
| 2007/0055265 A1 | 3/2007 | Schaller |
| 2007/0055266 A1 | 3/2007 | Osorio et al. |
| 2007/0055267 A1 | 3/2007 | Osorio et al. |
| 2007/0055271 A1 | 3/2007 | Schaller |
| 2007/0055272 A1 | 3/2007 | Schaller |
| 2007/0055273 A1 | 3/2007 | Schaller |
| 2007/0055274 A1 | 3/2007 | Appenzeller et al. |
| 2007/0055275 A1 | 3/2007 | Schaller |
| 2007/0055276 A1 | 3/2007 | Edidin |
| 2007/0055277 A1 | 3/2007 | Osorio et al. |
| 2007/0055278 A1 | 3/2007 | Osorio et al. |
| 2007/0055281 A1 | 3/2007 | Osorio et al. |
| 2007/0055284 A1 | 3/2007 | Osorio et al. |
| 2007/0055300 A1 | 3/2007 | Osorio et al. |
| 2007/0055377 A1 | 3/2007 | Hanson et al. |
| 2007/0060933 A1 | 3/2007 | Sankaran et al. |
| 2007/0060935 A1 | 3/2007 | Schwardt et al. |
| 2007/0067034 A1 | 3/2007 | Chirico et al. |
| 2007/0068329 A1 | 3/2007 | Phan et al. |
| 2007/0073292 A1 | 3/2007 | Kohm et al. |
| 2007/0078436 A1 | 4/2007 | Leung et al. |
| 2007/0078463 A1 | 4/2007 | Malandain |
| 2007/0093689 A1 | 4/2007 | Steinberg |
| 2007/0093899 A1 | 4/2007 | Dutoit et al. |
| 2007/0093906 A1 | 4/2007 | Hudgins et al. |
| 2007/0118222 A1 | 5/2007 | Lang |
| 2007/0123986 A1 | 5/2007 | Schaller |
| 2007/0135922 A1 | 6/2007 | Trieu |
| 2007/0149978 A1 | 6/2007 | Sheziti et al. |
| 2007/0150059 A1 | 6/2007 | Ruberte et al. |
| 2007/0150060 A1 | 6/2007 | Trieu |
| 2007/0150061 A1 | 6/2007 | Trieu |
| 2007/0150063 A1 | 6/2007 | Ruberte et al. |
| 2007/0150064 A1 | 6/2007 | Ruberte et al. |
| 2007/0162127 A1 | 7/2007 | Peterman et al. |
| 2007/0167945 A1 | 7/2007 | Lange et al. |
| 2007/0168038 A1 | 7/2007 | Trieu |
| 2007/0173939 A1 | 7/2007 | Kim et al. |
| 2007/0173940 A1 | 7/2007 | Hestad et al. |
| 2007/0178222 A1 | 8/2007 | Storey et al. |
| 2007/0179612 A1 | 8/2007 | Johnson et al. |
| 2007/0179615 A1 | 8/2007 | Heinz et al. |
| 2007/0179616 A1 | 8/2007 | Braddock et al. |
| 2007/0179618 A1 | 8/2007 | Trieu et al. |
| 2007/0185578 A1 | 8/2007 | O'Neil et al. |
| 2007/0191953 A1 | 8/2007 | Trieu |
| 2007/0191959 A1 | 8/2007 | Hartmann et al. |
| 2007/0197935 A1 | 8/2007 | Reiley et al. |
| 2007/0198023 A1 | 8/2007 | Sand et al. |
| 2007/0198025 A1 | 8/2007 | Trieu et al. |
| 2007/0198089 A1 | 8/2007 | Moskowitz et al. |
| 2007/0208423 A1 | 9/2007 | Messerli et al. |
| 2007/0208426 A1 | 9/2007 | Trieu |
| 2007/0213717 A1 | 9/2007 | Trieu et al. |
| 2007/0219634 A1 | 9/2007 | Greenhalgh et al. |
| 2007/0233074 A1 | 10/2007 | Anderson et al. |
| 2007/0233244 A1 | 10/2007 | Lopez et al. |
| 2007/0260255 A1 | 11/2007 | Haddock et al. |
| 2007/0270957 A1 | 11/2007 | Heinz |
| 2007/0270968 A1 | 11/2007 | Baynham et al. |
| 2007/0276375 A1 | 11/2007 | Rapp |
| 2007/0282443 A1 | 12/2007 | Globerman et al. |
| 2007/0299521 A1 | 12/2007 | Glenn et al. |
| 2008/0009877 A1 | 1/2008 | Sankaran et al. |
| 2008/0015701 A1 | 1/2008 | Garcia et al. |
| 2008/0021556 A1 | 1/2008 | Edie |
| 2008/0021557 A1 | 1/2008 | Trieu |
| 2008/0021558 A1 | 1/2008 | Thramann |
| 2008/0027437 A1 | 1/2008 | Johnson et al. |
| 2008/0027453 A1 | 1/2008 | Johnson et al. |
| 2008/0027454 A1 | 1/2008 | Johnson et al. |
| 2008/0027550 A1 | 1/2008 | Link et al. |
| 2008/0033440 A1 | 2/2008 | Moskowitz et al. |
| 2008/0051897 A1 | 2/2008 | Lopez et al. |
| 2008/0051902 A1 | 2/2008 | Dwyer |
| 2008/0058944 A1 | 3/2008 | Duplessis et al. |
| 2008/0065219 A1 | 3/2008 | Dye |
| 2008/0071356 A1 | 3/2008 | Greenhalgh et al. |
| 2008/0082173 A1 | 4/2008 | Delurio et al. |
| 2008/0097611 A1 | 4/2008 | Mastrorio et al. |
| 2008/0125865 A1 | 5/2008 | Abdelgany |
| 2008/0132934 A1 | 6/2008 | Reiley et al. |
| 2008/0133017 A1 | 6/2008 | Beyar et al. |
| 2008/0140085 A1 | 6/2008 | Gately et al. |
| 2008/0140207 A1 | 6/2008 | Olmos et al. |
| 2008/0147193 A1 | 6/2008 | Matthis et al. |
| 2008/0161927 A1 | 7/2008 | Savage et al. |
| 2008/0167657 A1 | 7/2008 | Greenhalgh |
| 2008/0177306 A1 | 7/2008 | Lamborne et al. |
| 2008/0177388 A1 | 7/2008 | Patterson et al. |
| 2008/0183204 A1 | 7/2008 | Greenhalgh et al. |
| 2008/0188945 A1 | 8/2008 | Boyce et al. |
| 2008/0195096 A1 | 8/2008 | Frei |
| 2008/0195209 A1 | 8/2008 | Garcia et al. |
| 2008/0195210 A1 | 8/2008 | Milijasevic et al. |
| 2008/0208255 A1 | 8/2008 | Siegal |
| 2008/0221687 A1 | 9/2008 | Viker |
| 2008/0229597 A1 | 9/2008 | Malandain |
| 2008/0243251 A1 | 10/2008 | Stad et al. |
| 2008/0243254 A1 | 10/2008 | Butler |
| 2008/0249622 A1 | 10/2008 | Gray |
| 2008/0281346 A1 | 11/2008 | Greenhalgh et al. |
| 2008/0281364 A1 | 11/2008 | Chirico et al. |
| 2008/0281425 A1 | 11/2008 | Thalgott et al. |
| 2009/0005873 A1 | 1/2009 | Slivka et al. |
| 2009/0018524 A1 | 1/2009 | Greenhalgh et al. |
| 2009/0030423 A1 | 1/2009 | Puno |
| 2009/0048678 A1 | 2/2009 | Saal et al. |
| 2009/0054991 A1 | 2/2009 | Biyani et al. |
| 2009/0069895 A1 | 3/2009 | Gittings et al. |
| 2009/0076610 A1 | 3/2009 | Afzal |
| 2009/0099568 A1 | 4/2009 | Lowry et al. |
| 2009/0112320 A1 | 4/2009 | Kraus |
| 2009/0112324 A1 | 4/2009 | Refai et al. |
| 2009/0164020 A1 | 6/2009 | Janowski et al. |
| 2009/0177281 A1 | 7/2009 | Swanson et al. |
| 2009/0177284 A1 | 7/2009 | Rogers et al. |
| 2009/0222096 A1 | 9/2009 | Trieu |
| 2009/0222099 A1 | 9/2009 | Liu et al. |
| 2009/0234398 A1 | 9/2009 | Chirico et al. |
| 2009/0240334 A1 | 9/2009 | Richelsoph |
| 2009/0240335 A1 | 9/2009 | Arcenio et al. |
| 2009/0248159 A1 | 10/2009 | Aflatoon |
| 2009/0248163 A1 | 10/2009 | King et al. |
| 2009/0276051 A1 | 11/2009 | Arramon et al. |
| 2009/0292361 A1 | 11/2009 | Lopez |
| 2010/0016905 A1 | 1/2010 | Greenhalgh et al. |
| 2010/0042218 A1 | 2/2010 | Nebosky et al. |
| 2010/0076559 A1 | 3/2010 | Bagga et al. |
| 2010/0094426 A1 | 4/2010 | Grohowski, Jr. et al. |

(56) References Cited

U.S. PATENT DOCUMENTS

| | | |
|---|---|---|
| 2010/0179594 A1 | 7/2010 | Theofilos et al. |
| 2010/0211182 A1 | 8/2010 | Zimmermann |
| 2010/0234956 A1 | 9/2010 | Attia et al. |
| 2010/0262240 A1 | 10/2010 | Chavatte et al. |
| 2010/0286783 A1 | 11/2010 | Lechmann et al. |
| 2010/0324607 A1 | 12/2010 | Davis |
| 2011/0004308 A1 | 1/2011 | Marino et al. |
| 2011/0004310 A1 | 1/2011 | Michelson |
| 2011/0015747 A1 | 1/2011 | McManus et al. |
| 2011/0029082 A1 | 2/2011 | Hall |
| 2011/0035011 A1 | 2/2011 | Cain |
| 2011/0082552 A1 | 4/2011 | Wistrom et al. |
| 2011/0093074 A1 | 4/2011 | Glerum et al. |
| 2011/0093076 A1 | 4/2011 | Reo et al. |
| 2011/0098818 A1 | 4/2011 | Brodke et al. |
| 2011/0130835 A1 | 6/2011 | Ashley et al. |
| 2011/0130838 A1 | 6/2011 | Morgenstern |
| 2011/0144753 A1 | 6/2011 | Marchek et al. |
| 2011/0159070 A1 | 6/2011 | Jin et al. |
| 2011/0172716 A1 | 7/2011 | Glerum |
| 2011/0270261 A1 | 11/2011 | Mast et al. |
| 2011/0282453 A1 | 11/2011 | Greenhalgh et al. |
| 2011/0301711 A1 | 12/2011 | Palmatier et al. |
| 2011/0301712 A1 | 12/2011 | Palmatier et al. |
| 2012/0004726 A1 | 1/2012 | Green Halgh et al. |
| 2012/0004732 A1 | 1/2012 | Goel et al. |
| 2012/0022654 A1 | 1/2012 | Farris et al. |
| 2012/0029636 A1 | 2/2012 | Ragab et al. |
| 2012/0071977 A1 | 3/2012 | Oglaza et al. |
| 2012/0071980 A1 | 3/2012 | Purcell et al. |
| 2012/0083889 A1 | 4/2012 | Purcell et al. |
| 2012/0123546 A1 | 5/2012 | Medina |
| 2012/0136443 A1 | 5/2012 | Wenzel |
| 2012/0197403 A1 | 8/2012 | Merves |
| 2012/0226357 A1 | 9/2012 | Varela |
| 2012/0277869 A1 | 11/2012 | Siccardi et al. |
| 2012/0290097 A1 | 11/2012 | Cipoletti et al. |
| 2012/0310350 A1 | 12/2012 | Farris et al. |
| 2012/0310352 A1 | 12/2012 | DiMauro et al. |
| 2013/0030536 A1 | 1/2013 | Rhoda et al. |
| 2013/0030544 A1 | 1/2013 | Studer |
| 2013/0060337 A1 | 3/2013 | Petersheim et al. |
| 2013/0073044 A1 | 3/2013 | Gamache |
| 2013/0085572 A1 | 4/2013 | Glerum et al. |
| 2013/0085574 A1 | 4/2013 | Sledge |
| 2013/0110240 A1 | 5/2013 | Hansell et al. |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0158663 A1 | 6/2013 | Miller et al. |
| 2013/0158664 A1 | 6/2013 | Palmatier et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0190875 A1 | 7/2013 | Shulock et al. |
| 2013/0190876 A1 | 7/2013 | Drochner et al. |
| 2013/0190877 A1 | 7/2013 | Medina |
| 2013/0204371 A1 | 8/2013 | McLuen et al. |
| 2013/0211525 A1 | 8/2013 | McLuen et al. |
| 2013/0211526 A1 | 8/2013 | Alheidt et al. |
| 2013/0218276 A1 | 8/2013 | Fiechter et al. |
| 2013/0253585 A1 | 9/2013 | Garcia et al. |
| 2013/0261746 A1 | 10/2013 | Linares et al. |
| 2013/0310939 A1 | 11/2013 | Fabian et al. |
| 2014/0039622 A1 | 2/2014 | Glerum et al. |
| 2014/0046333 A1 | 2/2014 | Johnson et al. |
| 2014/0046446 A1 | 2/2014 | Robinson |
| 2014/0058513 A1 | 2/2014 | Gahman et al. |
| 2014/0067073 A1 | 3/2014 | Hauck |
| 2014/0086962 A1 | 3/2014 | Jin et al. |
| 2014/0114414 A1 | 4/2014 | Abdou et al. |
| 2014/0114423 A1 | 4/2014 | Suedkamp et al. |
| 2014/0128977 A1 | 5/2014 | Glerum et al. |
| 2014/0128980 A1 | 5/2014 | Kirschman |
| 2014/0135934 A1 | 5/2014 | Hansell et al. |
| 2014/0142706 A1 | 5/2014 | Hansell et al. |
| 2014/0163683 A1 | 6/2014 | Seifert et al. |
| 2014/0172106 A1 | 6/2014 | To et al. |
| 2014/0180421 A1 | 6/2014 | Glerum et al. |
| 2014/0188225 A1 | 7/2014 | Dmuschewsky |
| 2014/0249629 A1 | 9/2014 | Moskowitz et al. |
| 2014/0249630 A1 | 9/2014 | Weiman |
| 2014/0257484 A1 | 9/2014 | Flower et al. |
| 2014/0257486 A1 | 9/2014 | Alheidt |
| 2014/0257494 A1 | 9/2014 | Thorwarth et al. |
| 2014/0277464 A1 | 9/2014 | Richter et al. |
| 2014/0277476 A1 | 9/2014 | McLean et al. |
| 2014/0277481 A1 | 9/2014 | Lee et al. |
| 2014/0303731 A1 | 10/2014 | Glerum |
| 2014/0303732 A1 | 10/2014 | Rhoda et al. |
| 2014/0324171 A1 | 10/2014 | Glerum et al. |
| 2015/0088256 A1 | 3/2015 | Ballard |
| 2015/0094812 A1 | 4/2015 | Cain |
| 2015/0112437 A1 | 4/2015 | Davis et al. |
| 2015/0164655 A1 | 6/2015 | DiMauro |
| 2015/0173914 A1 | 6/2015 | DiMauro et al. |
| 2015/0196401 A1 | 7/2015 | DiMauro et al. |
| 2015/0202052 A1 | 7/2015 | DiMauro |
| 2015/0216673 A1 | 8/2015 | DiMauro |
| 2015/0230932 A1 | 8/2015 | Schaller |
| 2015/0238324 A1 | 8/2015 | Nebosky et al. |
| 2016/0022437 A1 | 1/2016 | Kelly et al. |
| 2016/0038301 A1 | 2/2016 | Wickham |
| 2016/0038304 A1 | 2/2016 | Aquino Shluzas et al. |
| 2016/0051376 A1 | 2/2016 | Serhan et al. |
| 2016/0058573 A1 | 3/2016 | DiMauro et al. |
| 2016/0067055 A1 | 3/2016 | Hawkins et al. |
| 2016/0074170 A1 | 3/2016 | Rogers et al. |
| 2016/0074175 A1 | 3/2016 | O'Neil |
| 2016/0100954 A1 | 4/2016 | Rumi et al. |
| 2016/0120662 A1 | 5/2016 | Schaller |
| 2016/0128843 A1 | 5/2016 | Tsau et al. |
| 2016/0199196 A1 | 7/2016 | Serhan et al. |
| 2016/0228258 A1 | 8/2016 | Schaller et al. |
| 2016/0310296 A1 | 10/2016 | DiMauro et al. |
| 2016/0317313 A1 | 11/2016 | DiMauro |
| 2016/0317714 A1 | 11/2016 | DiMauro et al. |
| 2016/0331541 A1 | 11/2016 | DiMauro et al. |
| 2016/0331548 A1 | 11/2016 | DiMauro et al. |
| 2016/0338854 A1 | 11/2016 | Serhan et al. |
| 2016/0367380 A1 | 12/2016 | DiMauro |
| 2016/0374821 A1 | 12/2016 | DiMauro et al. |
| 2017/0035578 A1 | 2/2017 | DiMauro et al. |

FOREIGN PATENT DOCUMENTS

| | | |
|---|---|---|
| CN | 101909548 A | 12/2010 |
| DE | 28 04 936 A1 | 8/1979 |
| DE | 39 11 610 A1 | 10/1990 |
| DE | 40 12 622 C1 | 7/1991 |
| DE | 197 10 392 C1 | 7/1999 |
| DE | 20 2006 005 868 U1 | 6/2006 |
| DE | 20 2008 001 079 U1 | 3/2008 |
| EP | 0 282 161 A1 | 9/1988 |
| EP | 0 529 275 A2 | 3/1993 |
| EP | 0 621 020 A1 | 10/1994 |
| EP | 0 678 489 A1 | 10/1995 |
| EP | 0 743 045 A2 | 11/1996 |
| EP | 1 157 676 A1 | 11/2001 |
| EP | 1 290 985 A2 | 3/2003 |
| EP | 1 385 449 A2 | 2/2004 |
| EP | 1 532 949 A1 | 5/2005 |
| EP | 1 541 096 A1 | 6/2005 |
| EP | 1 385 449 B1 | 7/2006 |
| EP | 1 683 593 A2 | 7/2006 |
| EP | 1 698 305 B1 | 8/2007 |
| EP | 1 843 723 B1 | 3/2010 |
| EP | 2 368 529 A1 | 9/2011 |
| EP | 2 237 748 B1 | 9/2012 |
| EP | 2 641 571 A1 | 9/2013 |

(56) References Cited

FOREIGN PATENT DOCUMENTS

| | | |
|---|---|---|
| EP | 2 705 809 A1 | 3/2014 |
| EP | 2 764 851 A1 | 8/2014 |
| EP | 1 924 227 B1 | 12/2014 |
| FR | 2 712 486 A1 | 5/1995 |
| FR | 2 718 635 A1 | 10/1995 |
| FR | 2 730 159 A1 | 8/1996 |
| FR | 2874814 A1 | 3/2006 |
| FR | 2 913 331 A1 | 9/2008 |
| JP | 2003-526457 A | 9/2003 |
| JP | 2006-516456 A | 7/2006 |
| JP | 2011-509766 A | 3/2011 |
| JP | 2012-020153 A | 2/2012 |
| WO | 93/04634 A1 | 3/1993 |
| WO | 93/17669 A1 | 9/1993 |
| WO | 94/04100 A1 | 3/1994 |
| WO | 95/31158 A1 | 11/1995 |
| WO | 97/00054 A1 | 1/1997 |
| WO | 97/26847 A1 | 7/1997 |
| WO | 98/34552 A1 | 8/1998 |
| WO | 99/02214 A1 | 1/1999 |
| WO | 99/53871 A1 | 10/1999 |
| WO | 00/12033 A1 | 3/2000 |
| WO | 00/13620 A1 | 3/2000 |
| WO | 00/44288 A1 | 8/2000 |
| WO | 00/53127 A1 | 9/2000 |
| WO | 00/67650 A1 | 11/2000 |
| WO | 00/67651 A1 | 11/2000 |
| WO | 00/74605 A1 | 12/2000 |
| WO | 01/01893 A1 | 1/2001 |
| WO | 01/01895 A1 | 1/2001 |
| WO | 01/10316 A2 | 2/2001 |
| WO | 01/17464 A1 | 3/2001 |
| WO | 02/17824 A2 | 3/2002 |
| WO | 02/17825 A2 | 3/2002 |
| WO | 02/30338 A1 | 4/2002 |
| WO | 02/43628 A1 | 6/2002 |
| WO | 02/47563 A1 | 6/2002 |
| WO | 02/071921 A2 | 9/2002 |
| WO | 03/002021 A2 | 1/2003 |
| WO | 03/005937 A1 | 1/2003 |
| WO | 03/007854 A1 | 1/2003 |
| WO | 03/020169 A2 | 3/2003 |
| WO | 03/022165 A1 | 3/2003 |
| WO | 03/028587 A2 | 4/2003 |
| WO | 03/059180 A2 | 7/2003 |
| WO | 03/101308 A1 | 12/2003 |
| WO | 2004/034924 A2 | 4/2004 |
| WO | 2004/062505 A1 | 7/2004 |
| WO | 2004/082526 A2 | 9/2004 |
| WO | 2004/098420 A2 | 11/2004 |
| WO | 2004/108022 A1 | 12/2004 |
| WO | 2005/027734 A2 | 3/2005 |
| WO | 2005/032433 A2 | 4/2005 |
| WO | 2005/039455 A1 | 5/2005 |
| WO | 2005/051246 A2 | 6/2005 |
| WO | 2005/081877 A2 | 9/2005 |
| WO | 2005/112834 A2 | 12/2005 |
| WO | 2006/047587 A2 | 5/2006 |
| WO | 2006/047645 A2 | 5/2006 |
| WO | 2006/058281 A2 | 6/2006 |
| WO | 2006/060420 A1 | 6/2006 |
| WO | 2006/065419 A2 | 6/2006 |
| WO | 2006/066228 A2 | 6/2006 |
| WO | 2006/072941 A2 | 7/2006 |
| WO | 2006/081843 A1 | 8/2006 |
| WO | 2007/009107 A2 | 1/2007 |
| WO | 2007/022194 A2 | 2/2007 |
| WO | 2007/028098 A2 | 3/2007 |
| WO | 2007/048012 A2 | 4/2007 |
| WO | 2007/067726 A2 | 6/2007 |
| WO | 2007/084427 A2 | 7/2007 |
| WO | 2008/044057 A1 | 4/2008 |
| WO | 2008/103781 A2 | 8/2008 |
| WO | 2008/103832 A2 | 8/2008 |
| WO | 2009/064787 A2 | 5/2009 |
| WO | 2009/092102 A1 | 7/2009 |
| WO | 2009/124269 A1 | 10/2009 |
| WO | 2009/143496 A1 | 11/2009 |
| WO | 2010/068725 A2 | 6/2010 |
| WO | 2010/088766 A1 | 8/2010 |
| WO | 2010/148112 A1 | 12/2010 |
| WO | 2011/046459 A1 | 4/2011 |
| WO | 2011/046460 A1 | 4/2011 |
| WO | 2011/119617 A1 | 9/2011 |
| WO | 2011/142761 A1 | 11/2011 |
| WO | 2012/009152 A1 | 1/2012 |
| WO | 2012/028182 A1 | 3/2012 |
| WO | 2012/030331 A1 | 3/2012 |
| WO | 2012/089317 A1 | 7/2012 |
| WO | 2012/135764 A1 | 10/2012 |
| WO | 2013/006669 A2 | 1/2013 |
| WO | 2013/023096 A1 | 2/2013 |
| WO | 2013/025876 A1 | 2/2013 |
| WO | 2013/043850 A2 | 3/2013 |
| WO | 2013/082184 A1 | 6/2013 |
| WO | 2013/158294 A1 | 10/2013 |
| WO | 2013/173767 A1 | 11/2013 |
| WO | 2013/184946 A1 | 12/2013 |
| WO | 2014/014610 A1 | 1/2014 |
| WO | 2014/018098 A1 | 1/2014 |
| WO | 2014/026007 A1 | 2/2014 |
| WO | 2014/035962 A1 | 3/2014 |
| WO | 2014/088521 A2 | 6/2014 |
| WO | 2014/116891 A1 | 7/2014 |
| WO | 2015/048997 A1 | 4/2015 |

OTHER PUBLICATIONS

[No Author Listed] Longer BAK/L Sterile Interbody Fusion Devices. Date believed to be 1997. Product Data Sheet Zimmer. Retrieved Jul. 23, 2012 from <http://catalog.zimmer.com/content/zpc/products/600/600/620/S20/S045.html>. 2 pages.

[No Author Listed] OSTEOSET® DBM Pellets (Important Medical Information) [online], Nov. 2002 [retrieved on Oct. 14, 2003]. Retrieved from the Internet <URL: http://www.wmt.com/Literature>.

[No Author Listed] Sonic Accelerated Fracture Healing System/ Exogen 3000. Premarket Approval, U.S. Food & Drug Administration. Date believed to be May 10, 2000. Retrieved Jul. 23, 2012 from <http://www.accessdata.fda.gov/scripts/cdrh/cfdocs/cfPMA/pma.cfm?id=14736#>. 4 pages, 2012.

Barakat et al., 1996.

Bruder et al., Identification and characterization of a cell surface differentiation antigen on human osteoprogenitor cells. 42nd Annual Meeting of the Orthopaedic Research Society. p. 574, Feb. 19-22, 1996, Atlanta, Georgia.

Bruder et al., Monoclonal antibodies reactive with human osteogenic cell surface antigens. Bone. Sep. 1997;21 (3):225-235.

Burkoth et al., A review of photocrosslinked polyanhydrides: in situ forming degradable networks. Biomaterials. Dec. 2000;21(23):2395-2404.

Domb, 1996.

Flemming et al., Monoclonal anitbody against adult marrow-derived mesenchymal stem cells recognizes developing vasculature in embryonic human skin. Developmental Dynamics. 1998;212:119-132.

Gennaro, A.R., ed., Remington: The Science and Practice of Pharmacy. Williams & Wilkins, 19th edition, Jun. 1995.

Haas, Norbert P., New Products from AO Development [online], May 2002 [retrieved on Oct. 14, 2003]. Retrieved from the Internet <URL: http://www.ao.asif.ch/development/pdf_tk_news_02.pdf>.

Hao et al., Investigation of nanocomposites based on semi-interpenetrating network of [L-poly (epsilon-caprolactone)]/[net-poly (epsilon-caprolactone)] and hydroxyapatite nanocrystals. Biomaterials. Apr. 2003;24(9):1531-9.

Haynesworth et al., Cell surface antigens on human marrow-derived mesenchymal cells are detected by monoclonal antibodies. Bone. 1992;13(1):69-80.

(56) References Cited

OTHER PUBLICATIONS

Hitchon et al., Comparison of the biomechanics of hydroxyapatite and polymethylmethacrylate vertebroplasty in a cadaveric spinal compression fracture model. J Neurosurg. Oct. 2001;95(2 Suppl):215-20.
Invitation to Pay Additional Fees mailed Aug. 10, 2004 for Application No. PCT/US2004/004284 (8 Pages).
International Search Report and Written Opinion mailed Dec. 29, 2004 for Application No. PCT/US2004/004284 (17 Pages).
International Preliminary Report on Patentability mailed Feb. 15, 2005 for Application No. PCT/US2004/004284 (8 Pages).
Kandziora, Frank, et al., "Biomechanical Analysis of Biodegradable Interbody Fusion Cages Augmented with Poly (propylene Glycol-co-Fumaric Acid)," Spine, 27(15): 1644-1651 (2002).
Kricheldorf and Kreiser-Saunders, 1996.
Kroschwitz et al., eds., Hydrogels. Concise Encyclopedia of Polymer Science and Engineering. Wiley and Sons, pp. 458-459, 1990.
Lange, A.L., Lange's Handbook of Chemistry. McGraw-Hill Inc., 13th edition, Mar. 1985.
Lendlein et al., AB-polymer networks based on oligo(epsilon-caprolactone) segments showing shape-memory properties. Proc Natl Acad Sci U S A. Jan. 30, 2001;98(3):842-7. Epub Jan. 23, 2001.
Malberg, M.I., MD; Pimenta, L., MD; Millan, M.M., MD, 9th International Meeting on Advanced Spine Techniques, May 23-25, 2002, Montreux, Switzerland. Paper #54, Paper #60, and E-Poster #54, 5 pages.
Massia and Hubbell, 1991.
McAfee et al., Minimally invasive anterior retroperitoneal approach to the lumbar spine: Emphasis on the lateral BAK. SPINE. 1998;23(13):1476-84.
Mendez et al., Self-curing acrylic formulations containing PMMA/PCL composites: properties and antibiotic release behavior. J Biomed Mater Res. Jul. 2002;61(1):66-74.
New Zealander Office Action issued Jul. 9, 2007 for Application No. 541626 (3 Pages).
Regan et al., Endoscopic thoracic fusion cage. Atlas of Endoscopic Spine Surgery. Quality Medical Publishing, Inc. 1995;350-354.
Slivka et al., In vitro compression testing of fiber-reinforced, bioabsorbable, porous implants. Synthetic Bioabsorbable Polymers for Implants. STP1396, pp. 124-135, ATSM International, Jul. 2000.
Stewart et al., Co-expression of the stro-1 anitgen and alkaline phosphatase in cultures of human bone and marrow cells. ASBMR 18th Annual Meeting. Bath Institute for Rheumatic Diseases, Bath, Avon, UK. Abstract No. P208, p. S142, 1996.
Timmer et al., In vitro degradation of polymeric networks of poly(propylene fumarate) and the crosslinking macromer poly(propylene fumarate)-diacrylate. Biomaterials. Feb. 2003;24(4):571-7.
United States Disctrict Court, Central District of California, Case No. 1:10-CV-00849-LPS, *Nuvasive, Inc.*, vs., *Globus Medical, Inc.*, Videotaped Deposition of: Luiz Pimenta, M.D., May 9, 2012, 20 pages.
Walsh et al., Preparation of porous composite implant materials by in situ polymerization of porous apatite containing epsilon-caprolactone or methyl methacrylate. Biomaterials. Jun. 2001;22(11):1205-12.
U.S. Appl. No. 14/875,983, filed Oct. 6, 2015, In-Situ Formed Intervertebral Fusion Device and Method.
U.S. Appl. No. 14/886,302, filed Oct. 19, 2015, In-Situ Formed Intervertebral Fusion Device and Method.
U.S. Appl. No. 14/886,362, filed Oct. 19, 2015, In-Situ Formed Intervertebral Fusion Device and Method.
U.S. Appl. No. 14/934,289, filed Nov. 6, 2015, In-Situ Formed Intervertebral Fusion Device and Method.

[No Author Listed] Link SB Charite—Intervertebral Prosthesis, Brochure, Waldemar Link GmbH & Co., 1988, 29 pages.
[No Author Listed] Porocoat® Porous Coating, Depuy Synthes Companies, 2015, 2 pages, webpage, accessed Jul. 5, 2016, <https://emea.depuysynthes.com/hcp/hip/products/qs/porocoat-porous-coating-emea>.
[No Author Listed] Spine Solutions—The non-fusion technology company, Brochure, Prodisc, Spine Solutions, Inc., 2001, 16 pages.
Carrino, John A., Roxanne Chan and Alexander R. Vaccaro, "Vertebral Augmentation: Vertebroplasty and Kyphoplasty", Seminars in Roentgenology, vol. 39, No. 1 (Jan.), 2004:; pp. 68—84.
Cheng B.C. Ph.D., Biomechanical pullout strength and histology of Plasmapore® XP coated implants: Ovine multi time point survival study. Aesculap Implant Systems, LLC, 2013, 12 pages.
Chiang, et al., Biomechanical Comparison of Instrumented Posterior Lumbar Interbody Fusion with One or Two Cages by Finite Element Analysis, Spine, 2006, pp. E682-E689, vol. 31 (19), Lippincott Williams & Wilkins, Inc.
Edeland, H.G., "Some Additional Suggestions for an Intervertebral Disc Prosthesis", J of Bio Medical Engr., vol. 7(1) pp. 57-62, Jan 1985.
European Search Report EP03253921.5, dated Nov. 13, 2003, 4 pages.
Folman, et al., Posterior Lumbar Interbody Fusion for Degenerative Disc Disease Using a Minimally Invasive B-Twin Expandable Spinal Spacer, Journal of Spinal Disorders & Techniques, 2003, pp. 455-460, vol. 16(5).
Gore, Technique of Cervical Interbody Fusion, Clinical Orthopaedics and Related Research, 1984, pp. 191-195, No. 188.
Hoagland, T., et al., Total Lumbar Intervertebral Disc Replacement: Testing of a New Articulating Space in Human Cadaver Spines—24th Annual ORS, Dallas, TX, Feb. 21-23, 1978, 8 pages.
Hunt, et al., Expandable cage placement via a posterolateral approach in lumbar spine reconstructions, Journal of Neurosurgery: Spine, 2006, pp. 271-274, vol. 5.
International Patent Application No. PCT /US2013/029014, International Search Report dated Jul. 1, 2013, 2 pages.
Josh!, Ajeya P., M.D. and Paul A. Glazer, M.D., "Vertebroplasty: Current Concepts and Outlook for the Future", 2003, (5 pages), From: http://www.orthojournalhms.org/html/pdfs/manuscript-15.pdf.
Kotsias, A., Clinical trial of titanium-coated PEEL cages anterior cervical discectomy and fusion. [Klinishe Untersuching zum Einsatz von titanbeschichteten Polyetheretherketon-Implantaten bei der cervikalen interkorporalen fusion]. Doctoral thesis. Department of Medicine, Charite, University of Medicine Berlin, 2014, 73 pages. German language document.
Krbec, et al., [Replacement of the vertebral body with an expansion implant (Synex)], Acta Chir Orthop Traumatol Cech, 2002, pp. 158-162, vol. 69(3). Article in Czech. English Abstract Only.
Polikeit, et al., The importance of the end plate for interbody cages in the lumbar spine, Eur Spine J, 2003, pp. 556-561, vol. 12.
Shin, et al., Posterior Lumbar Interbody Fusion via a Unilateral Approach, Yonsei Medical Journal, 2006, pp. 319-325, vol. 47(3).
U.S. Appl. No. 60/557,246 filed Mar. 29, 2004 entitled: Device and Methods to Reduce and Stabilize Broken Bones.
U.S. Appl. No. 60/689,570 filed Jun. 13, 2005; Inventor: Tzony Siegal, Title: Directional Drilling System.
[No. Author Listed] Porocoat® Porous Coating, Depuy Synthes Companies, 2017, 1 page, webpage, accessed Jul. 31, 2017, <https://emea.depuysynthes.com/hcp/hip/products/qs/porocoat-porous-coating-emea>.

\* cited by examiner

IN-SITU FORMED INTERVERTEBRAL FUSION DEVICE AND METHOD

RELATED APPLICATIONS

This application is a continuation of U.S. application Ser. No. 14/684,959, filed on Apr. 13, 2015, which is a continuation of U.S. application Ser. No. 14/674,070, filed on Mar. 31, 2015, which is a continuation of U.S. application Ser. No. 14/668,576, filed on Mar. 25, 2015, which is a continuation of U.S. application Ser. No. 14/640,741, filed on Mar. 6, 2015, which is a continuation of U.S. application Ser. No. 14/632,875, filed on Feb. 26, 2015, which is a continuation of U.S. application Ser. No. 13/490,743, filed on Jun. 7, 2012, which is a continuation of U.S. application Ser. No. 10/778,684, filed on Feb. 13, 2004, which claims the benefit of U.S. Provisional Application No. 60/448,221, filed on Feb. 14, 2003. The entire teachings of the above applications are incorporated herein by reference.

BACKGROUND OF THE INVENTION

A leading cause of lower back pain arises from lumbar intervertebral disc pathology, including rupture or degeneration of the disc. Radicular pain in the lower extremities may be caused by the compression of spinal nerve roots by a bulging disc. Additionally, lower back pain may be caused by collapse of the disc and the dysarthrosis of an unstable or degenerative vertebral facet joint. One proposed method of managing these problems is to remove the problematic disc and replace it with a porous device that restores disc height and allows for bone growth therethrough for the fusion of the adjacent vertebrae. These devices are commonly called "fusion devices."

Intervertebral body fusion devices typically must carry extremely high loads (on the order of 1-4 kN) for a period of several months, or until fusion occurs. Accordingly, a fusion device or bone graft substitute designed for promoting bony fusion at another location in the body (such as long bone fusion) may not be suitable for use as an intervertebral body fusion device. For example, many bony fusion devices disclose the use of a gel such as a hydrogel as the structural carrier for an osteoinductive or an osteogeneic component. However, such gels typically do not posses the stiffness or mechanical strength found to be required for lumbar intervertebral fusion devices.

In general, delivery of conventional intervertebral fusion devices has required significantly invasive implantation procedures. Open surgical implantation of posterior implants requires excision of stabilizing muscles, ligaments, tendons, and bony structures such as the facet joints. The implants must not only overcome the destabilization caused by the surgical procedure, but must add the extra stability needed to promote bony fusion. Open anterior surgery in the lumbar spine is very risky due to the close proximity of sensitive vascular structures, such as the aorta and bifurcation of the aorta. Furthermore, the anterior open procedure can cause significant scar formation on the spine, making anterior revision surgery, if necessary, even more risky.

Minimally invasive procedures have been developed to help mitigate these problems. However, current techniques require appreciable surgical expertise and can significantly increase surgery time. Furthermore, insertion of interbody fusion cages through minimally invasive means often requires high insertion forces.

A number of such prosthetic implants have been described for serving as an intervertebral disc, or nucleus pulposus, replacement, involving the delivery of prosthetic materials through a small diameter cannula no larger than is needed to perform an adequate discectomy. Therefore, the injectable prosthetic devices are typically delivered in a first fluid form and then harden to a second form once inside the disc space to span the disc space height and preferably fill the disc space following discectomy. However, the requirements for a bone fusion system are very different from those of injectable prosthetic devices.

In summary, there is a need for an intervertebral strut injectable into the disc space that can create or maintain a preferred spatial relationship between adjacent vertebral body endplates (curvature and distraction) and comprises an osteogenic component to promote bony fusion between the two adjacent vertebra.

SUMMARY OF THE INVENTION

The present invention relates to a device for intervertebral spinal fusion and method of making thereof.

In one embodiment, the present invention is an orthopedic device for implanting between adjacent vertebrae comprising a generally arcuate balloon and a hardenable material within said balloon.

In another embodiment, the present invention is an intervertebral spinal fusion device comprising at least one arcuate inflatable balloon whereby at least partially filling the balloon between two adjacent vertebrae at least partially restores a natural angle between the adjacent vertebrae, and wherein said arcuate balloon contains a load-bearing component within a lumen defined by the balloon.

In another embodiment, the present invention is an intervertebral spinal fusion device comprising a anterior frame having an upper inflatable rim and a lower inflatable rim, and a rigid inflatable posterior frame attached to the upper and lower inflatable rims of the anterior frame. The anterior frame is detachably connected to the first fluid communication means. The posterior frame is detachably connected to the second fluid communication means. Upon at least partially filling the upper and lower inflatable rims and the posterior frame between two adjacent vertebrae, a natural angle between said vertebrae is at least partially restored.

In another embodiment, the present invention is a method of implanting an intervertebral spinal fusion device, comprising the steps of (a) performing a discectomy while preserving an outer annular shell; (b) inserting an inflatable device that includes a deflated arcuate balloon into an intervertebral space; (c) directing an osteobiologic component into the deflated arcuate balloon in an amount sufficient to inflate the balloon and distract the disc space.

In another embodiment, the present invention is a method of implanting an intervertebral spinal fusion device, comprising the steps of (a) inserting an inflatable device through a cannula into an intervertebral space, said inflatable device including an arcuate balloon connected to at least one fluid communication means, wherein said inflatable device upon expansion between two adjacent vertebrae at least partially restores a natural angle between the adjacent vertebrae; (b) orienting said inflatable device so that upon expansion a natural angle between vertebrae will be at least partially restored; (c) directing a load-bearing component into the inflatable device through the fluid communication means.

In another embodiment, the present invention is a method of at least partially restoring a natural angle between two adjacent vertebrae, comprising the steps of (a) inserting an inflatable device through a cannula into an intervertebral space; (b) orienting said inflatable device so that upon expansion of the device a natural angle between vertebrae will be at least partially restored; and (c) expanding said inflatable device by directing a load-bearing component into said inflatable device.

In another embodiment, the present invention is a method of delivering an osteobiologic material comprising (a) inserting an inflatable device into an intervertebral space wherein at least a portion of the device upon expansion has a substantially toroidal shape thereby forming an open cavity defined by an outer surface of the toroidal shape and having an axial dimension and a radial dimension; (b) orienting at least a portion of the device so that so that the axial dimension of the open cavity is substantially parallel to a major axis of a spinal column of a patient in which the device has been implanted; (b) inflating said inflatable device by directing a load-bearing component into said inflatable device; (c) directing an osteobiologic material into the open cavity, said material including at least one water-soluble material; (d) directing an aqueous fluid into the open cavity defined, by the inflated device thereby dissolving at least one said water-soluble material, and forming a porous matrix; and (e) delivering additional osteobiologic component into the porous matrix in the amount sufficient to fill at least 90% of the porous matrix by volume.

In another embodiment, the present invention is a pharmaceutical composition comprising a pharmaceutically acceptable carrier or diluent and (a) at least one polymer flowable between 38° C. and 45° C. selected from the group consisting of homopolymers of poly(ε-caprolactone), poly (p-dioxanone), or poly(trimethylene carbonate) or copolymers or mixtures thereof, or copolyesters of p-dioxanone or trimethylene carbonate and glycolide or lactide or mixtures thereof, and in particular, copolymers of p-dioxanone/glycolide, p-dioxanone/lactide, trimethylene carbonate/glycolide and trimethylene carbonate/lactide, or copolyesters of .epsilon.-caprolactone and glycolide or mixtures thereof, or mixtures of homopolymers of ε-caprolactone and lactide; and (b) at least one growth factor resistant to denaturing at least about 45° C. selected from the group consisting of bone morphogenetic proteins.

In another embodiment, the present invention is an intervertebral fusion device comprising an in-situ formed osteobiologic component comprising (a) a matrix having an internal surface defining an open porosity suitable for bone growth therethrough, and (b) an osteogenic component located within the open porosity.

In another embodiment, the present invention is an intervertebral fusion device for providing bony fusion across a disc space, comprising (a) a strut having a upper surface for bearing against the upper endplate and a lower surface for bearing against the lower endplate, and (b) an in-situ formed osteobiologic component.

In another embodiment the present invention is an intervertebral fusion device for providing bony fusion across a disc space, comprising a strut comprising (a) an upper surface for bearing against the upper endplate, (b) a lower surface for bearing against the lower endplate, and (c) an injectable load bearing composition disposed between the upper and lower surfaces.

In another embodiment, the present invention is an intervertebral fusion device comprising a matrix having an internal surface defining an open porosity suitable for bone growth therethrough, wherein the matrix is formed by a plurality of in-situ bonded beads.

In another embodiment, the present invention is an intervertebral fusion device comprising a strut comprising (a) a first component comprising (i) a lower bearing surface adapted for bearing against a lower vertebral endplate, and (ii) an upper surface comprising a leading end, an angled middle portion and a trailing end; and (b) a second component comprising (i) an upper bearing surface adapted for bearing against an upper vertebral endplate and (ii) an upper surface comprising a leading end, an angled middle portion and a trailing end. The angled portion of the first component mates with the angled portion of the second component.

In another embodiment, the present invention is a kit for providing interbody fusion across an intervertebral disc space, comprising (a) a cannula defining an inner diameter; (b) a hardenable material capable of supporting intervertebral load; and (c) a flowable osteobiologic composition.

In another embodiment, the present invention is an intervertebral fusion device for providing bony fusion across a disc space, comprising (a) a strut having a upper surface for bearing against an upper endplate and a lower surface for bearing against a lower endplate, the upper surface and lower surface defining a height therebetween, and (b) an in-situ formed osteobiologic component. The height of the strut is no greater than the height of the disc space.

In another embodiment, the present invention is a method of providing interbody fusion across an intervertebral disc space, comprising the steps of (a) providing a cannula defining an inner diameter; (b) moving a load bearing composition through the cannula and into the disc space to form a in-situ formed load bearing strut; and (c) moving an osteobiologic composition through the cannula and into the disc space to form an in-situ formed osteobiologic composition.

In another embodiment, the present invention is an intervertebral fusion device for providing bony fusion across a disc space, comprising a strut comprising (a) an upper surface for bearing against the upper endplate and (b) a lower surface for bearing against the lower endplate. The strut comprises an in-situ formed load bearing composition.

In another embodiment, the present invention is an intervertebral fusion device for providing bony fusion across a disc space, comprising a strut comprising (a) an upper surface for bearing against the upper endplate, (b) a lower surface for bearing against the lower endplate, and (c) an in-situ formed load bearing composition disposed between the upper and lower surfaces.

In another embodiment the present invention is an intervertebral fusion device comprising (a) a strut have a shape memory and comprising (i) an upper surface for bearing against the upper endplate, (ii) a lower surface for bearing against the lower endplate, and (b) an in-situ formed osteobiologic component.

In another embodiment, the present invention is an intervertebral fusion device comprising (a) a strut comprising an upper surface for bearing against the upper endplate and a lower surface for bearing against the lower endplate, and (b) an in-situ formed osteobiologic component comprising a matrix component having an internal surface defining a scaffold having open porosity suitable for bone growth therethrough, and an osteogenic component located within the open porosity.

In another embodiment, the present invention is an intervertebral fusion device comprising a strut comprising an upper surface for bearing against the upper endplate and a lower surface for bearing against the lower endplate, and an in-situ formed osteobiologic component comprising an injectable matrix component, an osteoinductve component embedded within the matrix.

In another embodiment, the present invention is an intervertebral fusion device comprising a strut comprising an upper surface for bearing against the upper endplate a lower surface for bearing against the lower endplate, and an in-situ formed osteobiologic component comprising an injectable matrix component, and a porogen embedded within the matrix.

In another embodiment, the present invention is an intervertebral fusion device comprising a strut comprising an upper surface for bearing against the upper endplate, a lower surface for bearing against the lower endplate, and an in-situ formed osteobiologic component comprising an expandable device defining a cavity, and an injectable osteobiologic composition located within the cavity.

In another embodiment, the present invention is an intervertebral fusion device comprising a strut comprising an expandable device having a cavity, an upper surface for bearing against the upper endplate, a lower surface for bearing against the lower endplate, and an inner wall defining a through hole and an injectable load bearing composition located within the cavity, and an osteobiologic component located in the throughhole.

In another embodiment, the present invention is an intervertebral fusion device comprising a strut comprising an upper surface for bearing against the upper endplate, and a lower surface for bearing against the lower endplate; and an in-situ formed osteobiologic component comprising an injectable, matrix component essentially free of monomer.

In another embodiment, the present invention is an intervertebral fusion device for providing bony fusion across a disc space, comprising a strut comprising (a) an upper surface for bearing against the upper endplate, (b) a lower surface for bearing against the lower endplate, and (c) an in-situ formed load bearing composition disposed between the upper and lower surfaces and made of a material comprising a cross-linked resorbable polymer.

The advantages of the present invention are numerous. One advantage is that the present invention makes possible minimally invasive surgical procedures to restore a natural angle and increase disc height between two adjacent vertebrae. Furthermore, the same device used to create distraction/lordosis can function as the intervertebral implant needed to maintain height and natural angle. Another advantage is that the present invention makes possible a minimally invasive procedure to create in situ a structural scaffold filled with osteoinductive materials.

BRIEF DESCRIPTION OF THE DRAWINGS

FIGS. 2 (f) and 2 (g) show a perspective and a top view, respectively, of a preferred embodiment of a device of the present invention.

FIG. 13 (a) and FIG. 13 (b) show inserting a cannula into an intervertebral space, followed by inserting an inflatable balloon of a generally toroidal shape into an intervertebral space through the cannula. The balloon is expanded by directing a load-bearing component into said balloon. FIG. 13 (c) shows injecting an osteobiologic component comprising a water-soluble component into an open cavity, defined by the outer surface of the balloon, and FIG. 13 (d) shows dissolving the water-soluble component.

FIG. 14 (c) is a cross section of the device of FIGS. 14 (a) and (b).

FIG. 14 (d) is a perspective view of the device of FIGS. 14 (a)-(c).

DETAILED DESCRIPTION OF THE INVENTION

Figure 1:
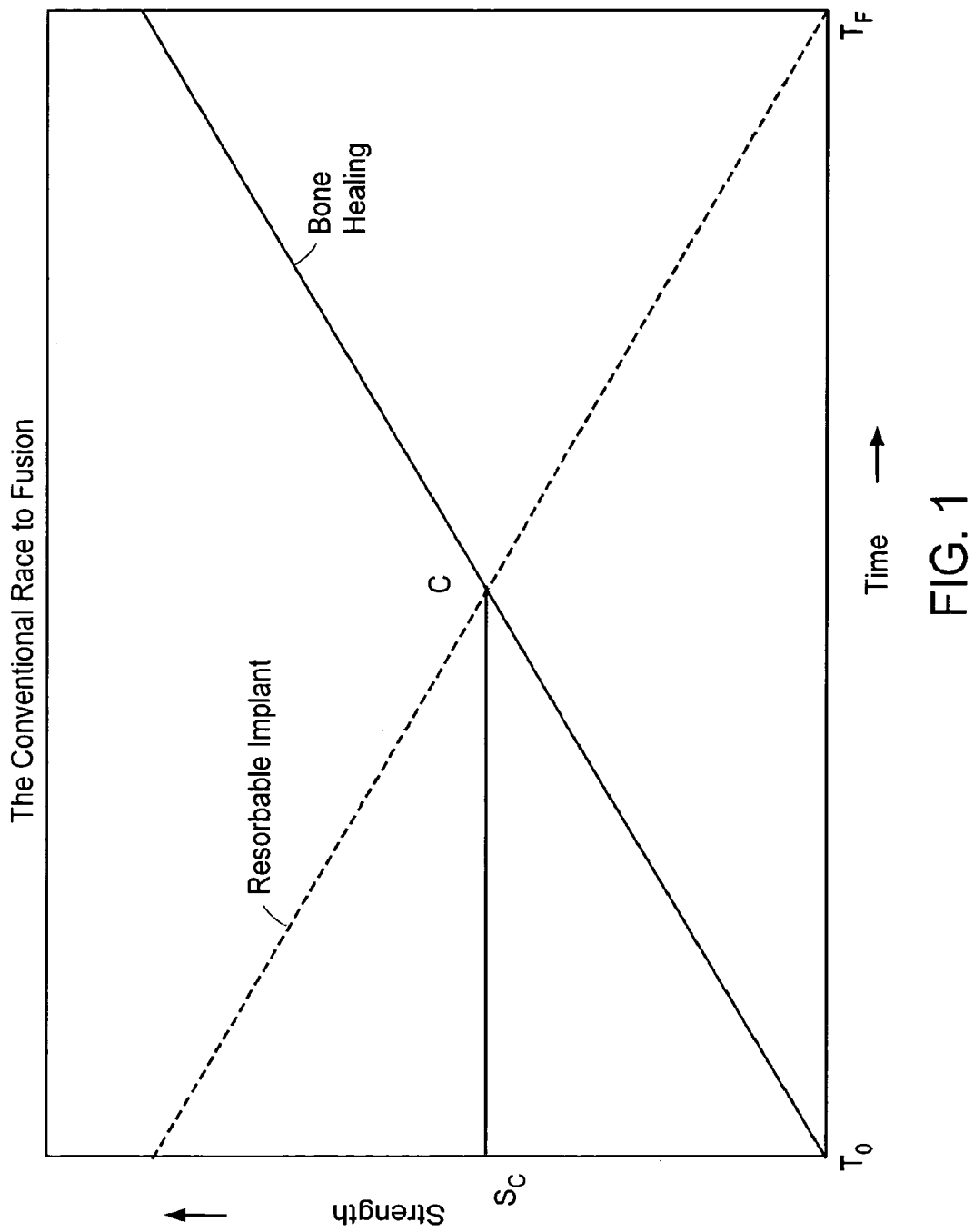
FIG. 1 is a plot of strength over time of a resorbable polymer and bone growth.
Figure 2A:
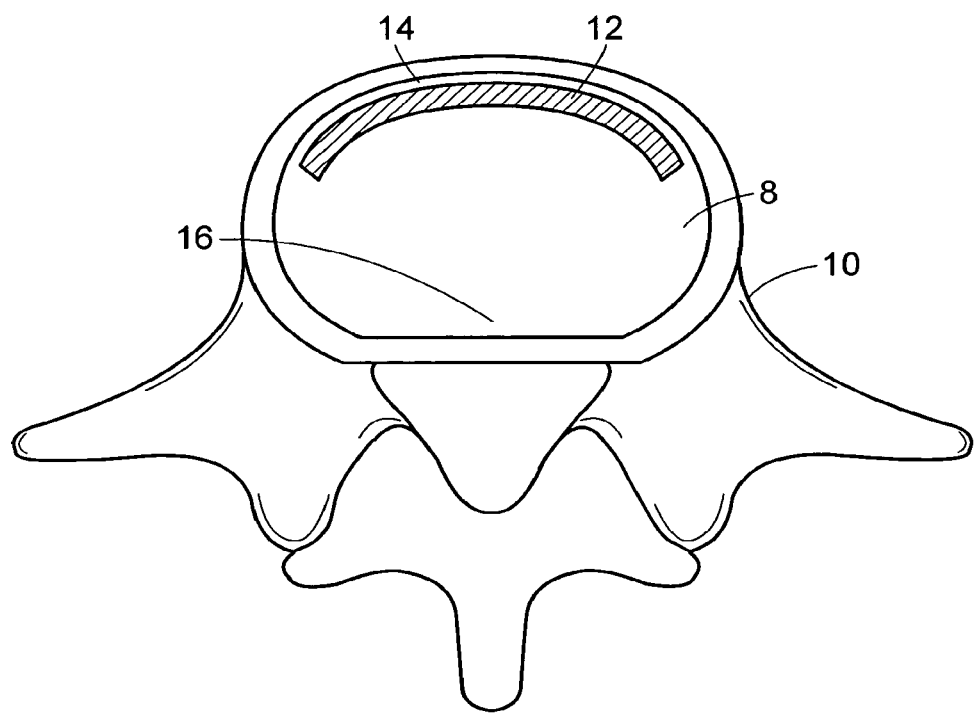
FIGS. 2 (a) through 2 (e) are schematic representations of preferred embodiments of a semicircular, circular, bilateral and generally crescent, arcuate, or toroidal shapes of the device of the present invention.
Figure 2B:
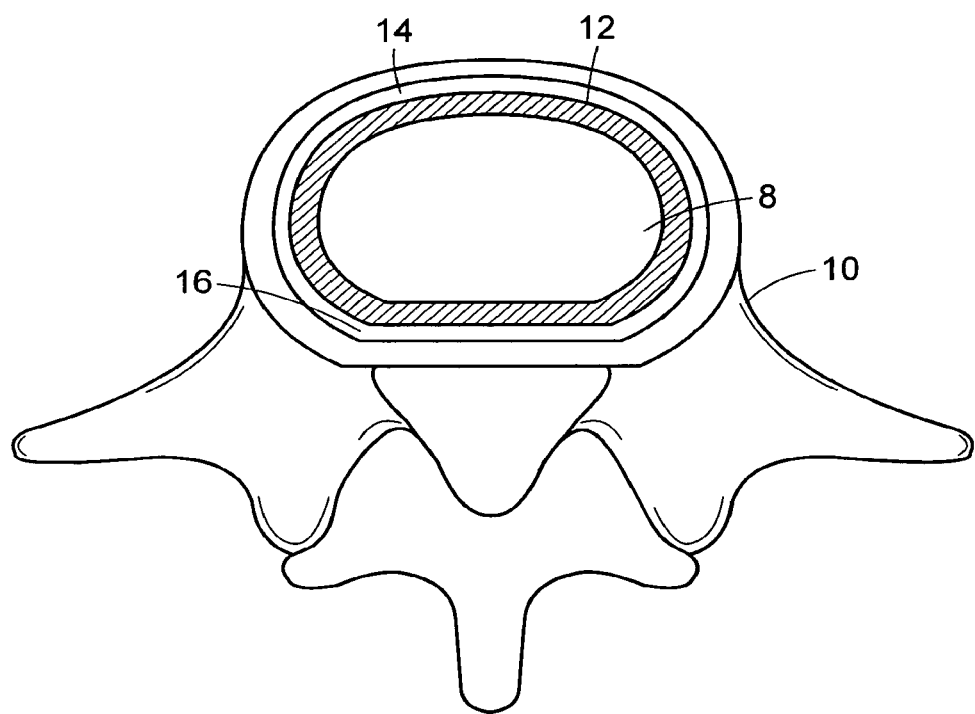
Figure 2C:
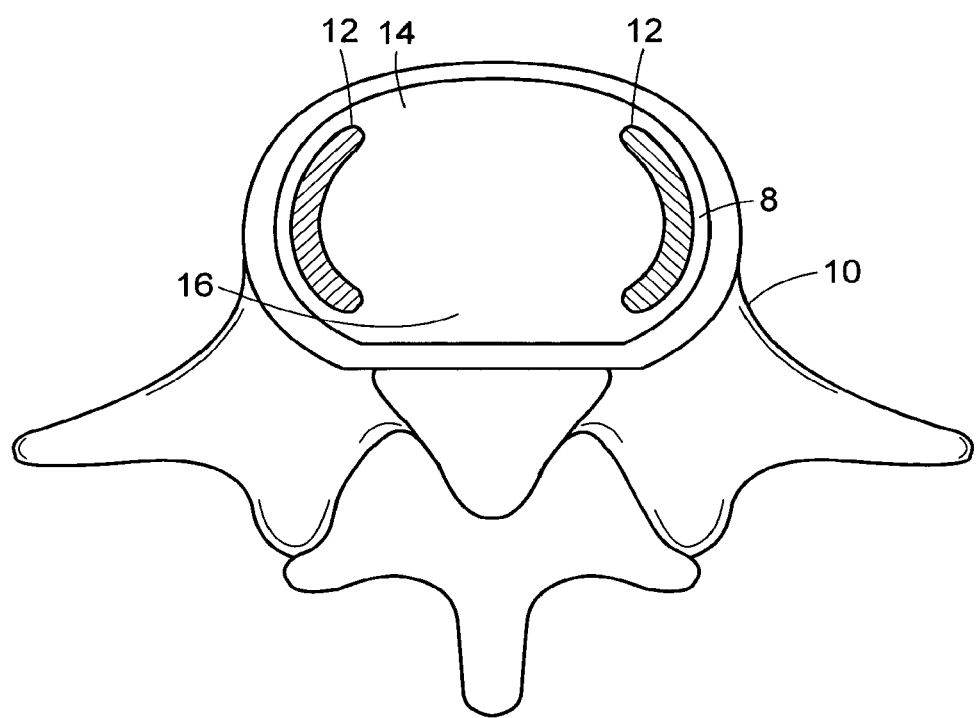
Figure 2D:
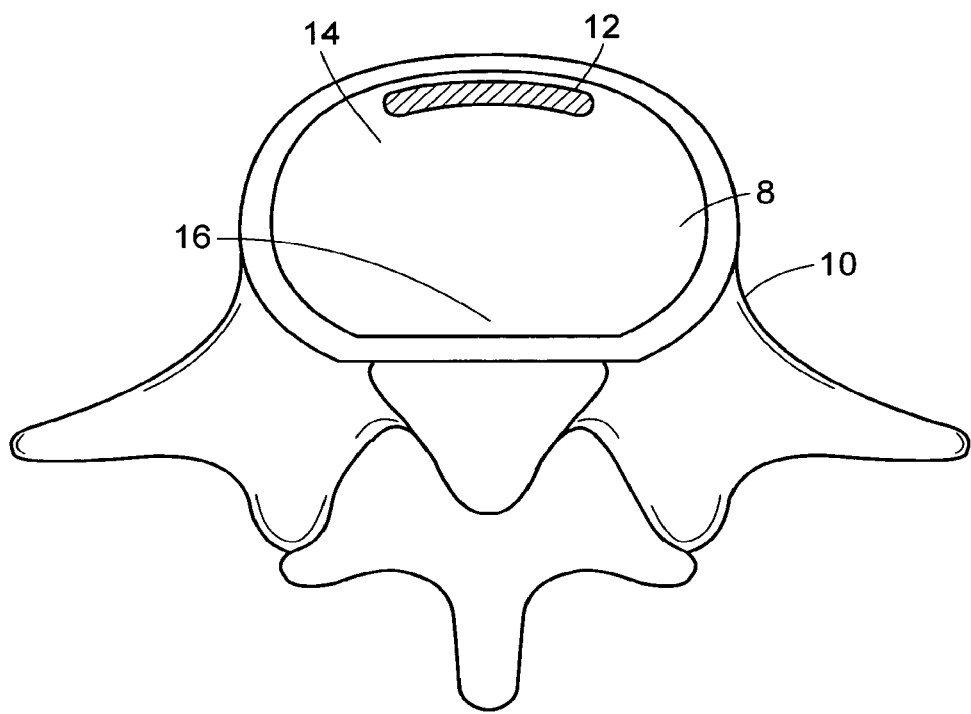
Figure 2E:
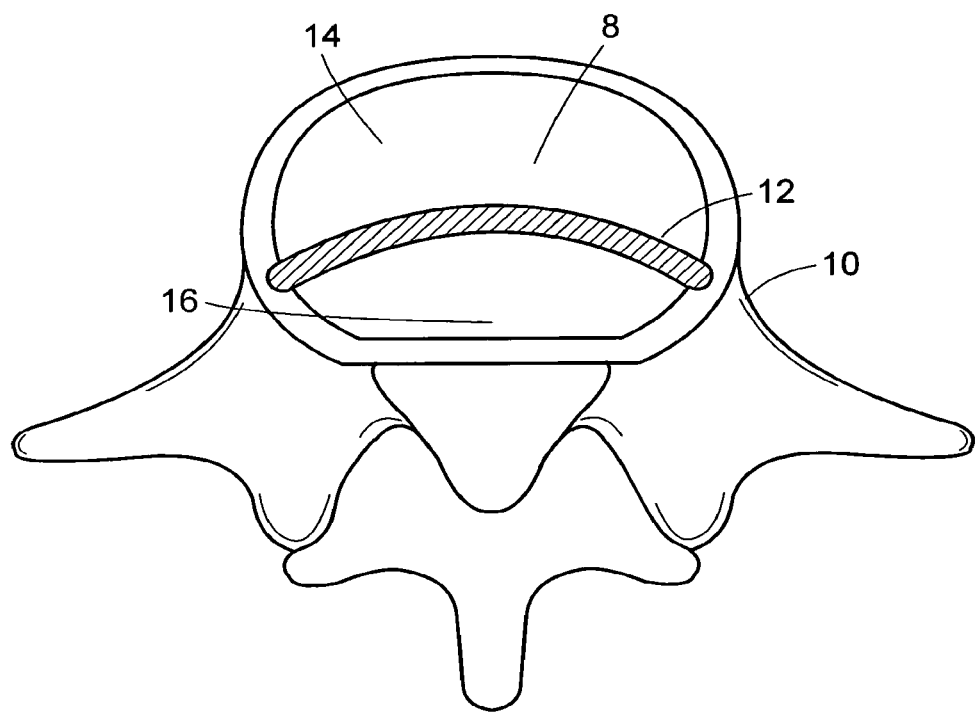
Figure 2F:
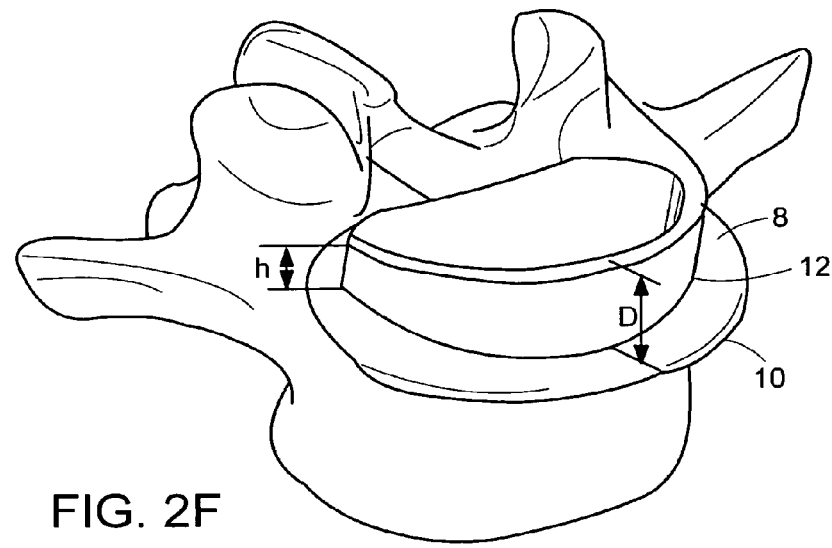
Figure 2G:
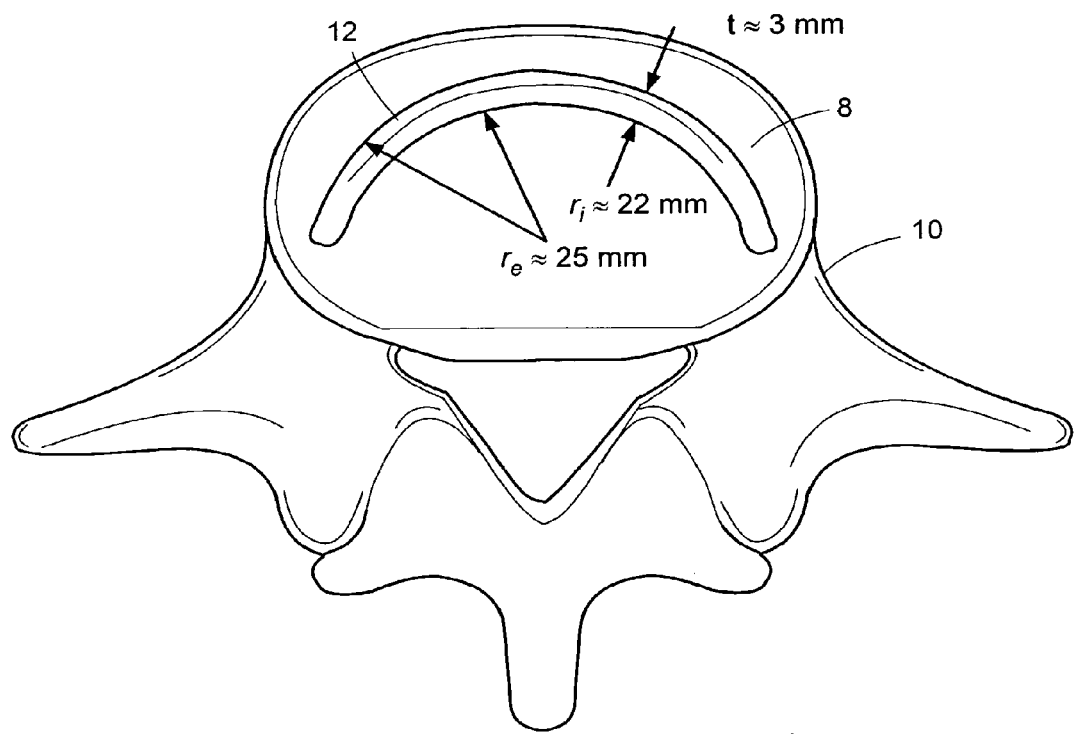

The present invention relates to a vertebral fusion device for simultaneously distracting two adjacent vertebral bodies and delivering a flowable material into a disk space. As used herein, the term "vertebral fusion" refers to a medical procedure that results in maintaining separation between vertebrae. In one embodiment, vertebral fusion provides for bony ingrowth that fixes two adjacent vertebrae in a desired, for example, distracted and/or angulated, position.

In a preferred embodiment, a natural angle between two adjacent vertebral plates is replicated by fusing the two adjacent vertebrae. As used herein, the "natural angle" refers either to natural lordosis or to natural kyphosis. The angle can be positive, negative or zero (i.e., when the opposing surfaces of the adjacent vertebrae are essntially coplanar). In one embodiment, a natural lordosis is replicated or restored. As used herein, the term "natural lordosis" refers to a natural angle between two adjacent vertebral plates within the lumbar or cervical spine segments wherein the distance between the anterior portions of the two adjacent vertebral plates is not smaller than the distance between the posterior portions of the two adjacent vertebral plates. In another embodiment, a natural kyphosis is replicated or restored. As used herein, the term "natural kyphosis" refers to a natural angle between two adjacent vertebral plates within the thoracic spine segment wherein the distance between the anterior portions of the two adjacent vertebral plates is not greater than the distance between the posterior portions of the two adjacent vertebral plates.

In another embodiment of vertebral fusion, a fusion means maintains the separation between the vertebrae. Preferably, the fusion means at least partially restore the natural function of nucleus pulposus by permitting relative freedom of movement while substantially maintaining the separation between the vertebrae.

The components of the device comprise at least one member selected from the group consisting of a load-bearing component and an osteobiologic component. Preferably, both components are used. In some embodiments, load-bearing component includes osteobiologic component. As used herein the term "load-bearing" component or material refers to any material capable of supporting vertebrae in distracted position. The load-bearing component can include a hardenable material or a noncompressible fluid contained within an inflatable balloon. The terms "strut" refers to any part, portion or component of the device, including a flowable material, that either alone or in combination with other parts, portions or components of the device is capable of supporting vertebrae in distracted position. Examples of a strut include a hardened flowable material, a balloon with rigid walls and an inflatable balloon or bag filled with a hardenable material or a noncompressible fluid. The purpose of the strut is to bear the high spinal loads. In addition, the strut can be used to increase the disc space height and/or at least partially restore or create natural curvature of the spinal region being fused. Increasing disc height is often critical for decompressing nerve roots and restoring or creating healthy spine curvature is important for preventing accelerated degeneration of adjacent intervertebral discs. The term "arcuate" refers to a shape having curvature roughly corresponding to the perimeter of a vertebral endplate, but does not include enclosed rings or generally annular structures.

As used herein, the "osteobiologic" component or material refers to any material that can induce and/or support existing or new bone growth. In some embodiments, the load-bearing material includes osteobiologic material. For example, a material comprising bone growth factors or mesynchemal stem cells is an osteobiologic component. Osteobiologic component can further include either one or both an osteoinductive component and an osteoconductive component. As used herein, the "osteoinductive" component or material refers to any material that can induce bone growth. Preferably, osteoinductive components includes signal molecules required to induce the osteoprogenitor cells to form new bone. Examples of osteoinductive components are bone morphogenetic proteins (BMP's), growth differentiation factors (GDF's) and transforming growth factors (TGF). As used herein, the "osteoconductive" component or material refers to any material that can provide support for bone growth subsequent to induction. Examples of osteoconductive components include natural collagen-based materials including bone, and synthetic porous resorbable polymers and ceramics.

Generally, the present invention relates to in situ formed intervertebral fusion devices. Preferably, the components of the in situ formed device can be delivered percutaneously (e.g., through a cannula having a diameter of no more than 5 mm, preferably no more than 2 mm). However, the precursor components of the in-situ formed device can also be delivered in cannulae of much larger dimension (such as up to 18 mm, or through a Craig needle). More preferably, the components of the in-situ formed device are delivered into the disc space in the form of injectable compositions.

For the purposes of the present invention, the term "in situ formed" refers to any material that is delivered into the disc space in a first form and takes on a different form after placed in the disc space. In some embodiments, "in situ formation" includes delivering a viscous fluid into the disc space and hardening that fluid. In some embodiments, "in situ formation" includes delivering discrete components into the disc space and bonding (preferably, heat bonding or by reaction) together those components. In some embodiments, "in situ formation" includes delivering discrete components into an opening in an inflatable device located in the disc space and preventing their escape from the inflatable device by closing off the opening of the inflatable device. In some embodiments, "in situ formation" includes delivering discrete components into the disc space and assembling together those components within the disc space.

In situ formation" excludes simply packing particles such as autograft or allograft particles into the disc space, as well as simply delivering a gel into the disc space.

Without being limited to any particular theory, it is believed that in conventional fusion systems, there is often a race between implant degradation and bone growth. Now referring to FIG. 1, the hypothetical strength profiles of a conventional resorbable implant (dotted line) and of the bone that replaces the implant (solid line) are provided. For the purpose of explaining FIG. 1, the strength of the system is defined as the lesser of the strength of the resorbable implant and the strength of the healing bone. It then follows that between the time of the surgical procedure ($T_0$) and the time for complete bone healing to take place ($T_F$), the load applied to the system must never be above the strength of the system at point C (shown as $S_C$). It is known in the art that the maximum in vivo average daily living load on the human lumbar spine is approximately 4,000 N. Assuming that this is the maximum load to be experienced by the system, then the system strength should not fall below 4,000 N.

Because the strut can be made relatively strong (e.g., capable of supporting about 15 kN in axial compression), even when the load applied to the system is relatively high, the strength of the system will still be sufficient to support the disc space and fusion will occur. Once sufficient bone growth through the osteobiologic component occurs, the strut may degrade without endangering support of the disc space.

To summarize, the strut supports the disc space while the osteobiologic composition grows bone.

In preferred embodiments, the strut of the present invention acts in a manner similar to the cortical rim of a vertebral body. Desirable features for the load bearing composition of the strut are as follows:

a) sufficient strength to bear the typical loads borne by vertebral bodies;
b) stiffness similar to that of cortical bone (or, in relatively thick embodiments, cortico-cancellous bone);
c) degradation resistance (e.g., capable of bearing at least 15 MPa, preferably at least 25 MPa) for at least one year, preferably at least 18 months;
d) resorbability.

Accordingly, in one embodiment, the present invention is an intervertebral spinal fusion device comprising a resorbable load-bearing material wherein the combination of the resorbable load-bearing material and the new bone growth provides a load-carrying capacity that is at least sufficient to support spinal load. Preferably, the load-bearing material includes or is supplemented by an osteobiologic component. In another embodiment, the present invention is a method of making an intervertebral fusion device comprising selecting a resorbable load-bearing material wherein the combination of the resorbable load-bearing material and the new bone growth provides a load-carrying capacity that is at least sufficient to support spinal load.

In one embodiment, the strut should have a size sufficient to provide a footprint covering between about 3% and about 40% of the area of the corresponding vertebral endplate. Preferably, the strut foot covers between about 10% and about 30%, more preferably between about 10% and about 20% of the corresponding vertebral endplate.

In some embodiments, in which the osteobiologic component contains at least one of a) a growth factor and b) an osteogenic component, e.g. a source of cells (such as stem cells), it is believed that the strut footprint can be in the range of about 10% to about 20% of the disc space. This is because it is believed that these additives sufficiently shorten the time to fusion so that the danger of strut subsidence is sufficiently low. Similarly, in some embodiments, in which the osteobiologic component contains both a) a growth factor and b) stem cells, it is believed that the strut footprint can be in the range of about 5% to about 10% of the disc space.

It is further believed that providing the osteobiologic component with both a) a growth factor and b) stem cells provides further desirable design options. These additives may also reduce or eliminate the need for posterior or supplemental fixation. Currently posterior fixation is generally thought to be highly desirable to achieve a fusion success in the interbody space. In some embodiments, the provision of effective amounts of such additives can increase the speed for fusion so as to render superfluous the posterior or supplemental fixation, and patients would no longer need to endure a more invasive pedicle screw procedure to apply the stability needed for fusion.

In some embodiments, the device can comprise a balloon of semicircular, circular, bilateral (comprising more than one balloon) and generally toroidal shape. Preferred embodiments and positions of a device of the present invention on an endplate 8 of a vertebra 10 are shown in FIGS. 2 (*a*) through (*e*). Now referring to FIG. 2 (*a*), this shape allows the balloon 12 to essentially cover at least the anterior periphery 14 of the corresponding vertebral endplate 8, and thereby bear a substantial portion of the spinal load. This shape further allows the surgeon to first place the device in place and then fill the remaining portion of the disc space with, for example, an osteobiologic component.

In other embodiments, as in FIG. 2 (*b*), the balloon 12 has a quasi-circular shape. This device has the advantage of providing even more of a load-bearing footprint than the embodiment of FIG. 2 (*a*), and also substantially prevents unwanted leakage of the osetobiologic component during subsequent filling of an open cavity defined by an outer surface of the balloon.

Now referring to FIG. 2 (*c*), in some embodiments, the device comprises two balloons 12 that can be used to support the vertebral load. The use of two balloons allows a surgeon to evenly support the load on each side of the endplate 8.

Now referring to FIG. 2 (*d*), in some embodiments, the balloon 12 has a generally toroidal ("banana") shape. The banana shape allows the surgeon to put in place a single device preferably on the anterior half 14 of the disc space. In other embodiments, the strut has the footprint of a banana cage such as that described in "Novel Banana Cage", filed Dec. 31, 2002, U.S. Ser. No. 10/334,599, the specification of which is incorporated by reference in its entirety.

Now referring to FIG. 2 (*e*), in some embodiments, the strut 12 is introduced translaterally so as to form a single ramp stretching essentially transversely across the endplate 8. This design in advantageous when used in a posterolateral approach of surgery, as this approach takes advantage of the fact that the muscle planes in the vicinity of the approach allow the implant to be delivered in a less invasive manner.

Now referring to FIG. 2 (*f*), in a preferred embodiment, the device 12 of the present invention has a substantially semiannular footprint. The device 12 is placed on the anterior portion of the endplate 8 of a vertebra 10 so that height D of a anterior portion of the device is equal or greater than height h of a posterior portion of the device 12. Referring to FIG. 2 (*g*), the device 12 defines an internal radius $r_i$, an external radius $r_e$ and thickness t. In one embodiment, illustrated in FIG. 2 (*g*), $r_i$ is approximately about 22 mm, $r_e$ is approximately about 25 mm and t is approximately about 3 mm.

In preferred embodiments, the height of the strut is at least 90%, and preferably at least equal to, the height of the natural disc space. This allows the surgeon to distract the disc space and restore at least a portion of the disc height. In some embodiments, the height of the strut is greater than that of the natural disc space.

As used herein the word "distraction" will refer to the separation of joint surfaces to a desired extent, without rupture of their binding ligaments and without displacement. Distraction can be accomplished by any suitable means, for example mechanical or hydrostatic means. Mechanical means can include, for instance, attaching hooks or jacks to the bony endplates and using those hooks or jacks to separate the bones. Optionally, the surgeon can employ external traction. In one embodiment, an in-situ foaming material is used as a distraction device. Other means include, for example, hydrostatic means, e.g., by pressurized injection of the biomaterial itself. By the use of distraction, the disc space can be sufficiently re-established to achieve any desired final dimensions and position. Optionally, and preferably, the means used to accomplish distraction also serves the purpose of forming one or more barriers (e.g., balloons) for the flowable load bearing strut material.

The disc space can be distracted prior to and/or during either a discectomy itself and/or delivery of a flowable biomaterial. A constricted disc space is generally on the order of 3 to 4 mm in height. Suitable distraction means are capable of providing on the order of about 3 atmospheres to about 4 atmospheres, (or on the order of about 40 psi to about 60 psi) in order to distract that space to on the order of 8 to 12 mm in height.

In one embodiments, the strut has a wedged shape so that the height of the anterior portion of the expanded device is greater than the height of the posterior portion of the expanded device. This allows the surgeon to restore lordosis when the interbody fusion device is used in either the lumbar or cervical regions of the spine. Preferably, the wedged shape produces an angle of between 5 and 20 degrees, more preferably between 5 and 15 degrees.

In another embodiment, the strut has a wedged shape so that the height of the anterior portion of the expanded device is smaller than the height of the posterior portion of the expanded device. This allows the surgeon to restore kyphosis when the interbody fusion device is used in thoracic regions of the spine. Preferably, the wedged shape produces an angle of between 5 and 20 degrees, more preferably between 5 and 15 degrees.

In preferred embodiments, the height of the medial portion of the strut is greater than the height of the lateral portion of the expanded device. This geometry more closely mimics the natural doming of the disc space.

With the injectable device of the present invention, there is provided a "custom" implant formed to the anatomy of the patient's endplates. The provision of a conformable implant may provide a faster and more consistent fusion.

In some embodiments, the annulus fibrosus can itself serve as a suitable mold for the delivery and solidification of either the flowable load-bearing material (in one embodiment) or the osteobiologic component (in another embodiment). Free injection may optimize the extent to which the injectable device conforms to the contour of the disc space, thereby enhancing resistance to retropulsion. Optionally, the interior surface of the annulus fibrosus can be treated or covered with a suitable material in order to enhance its integrity and use as a mold.

In some embodiments, at least one of the flowable materials is delivered into an inflatable device (such as a balloon) previously placed in the disc space.

Figure 3A:
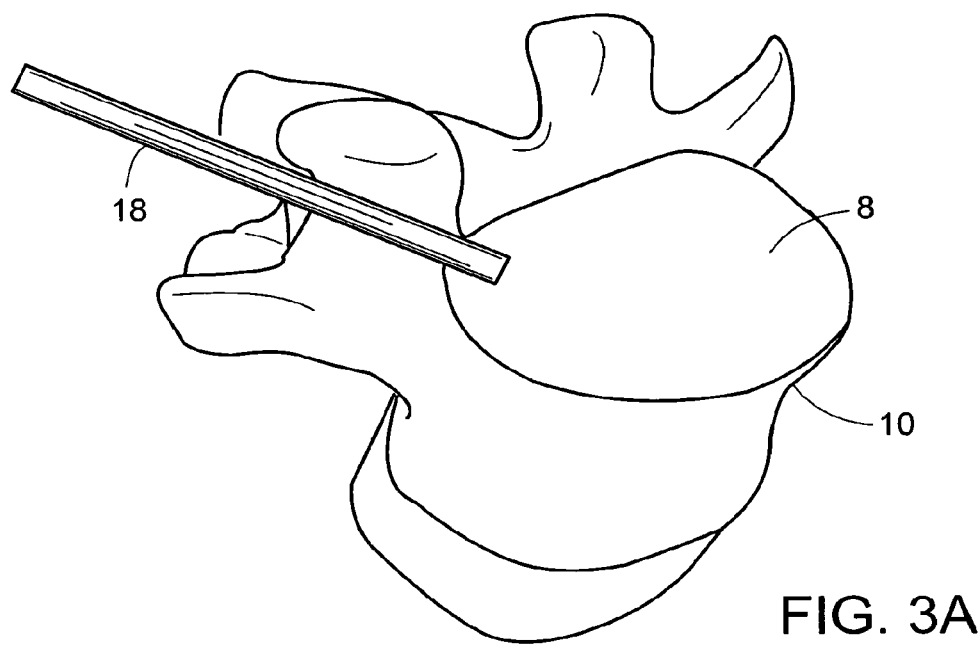
FIG. 3 (a) and FIG. 3 (b) show a perspective and a top view, respectively, of a preferred method of the introduction of a cannula into the disc space.
Figure 3B:
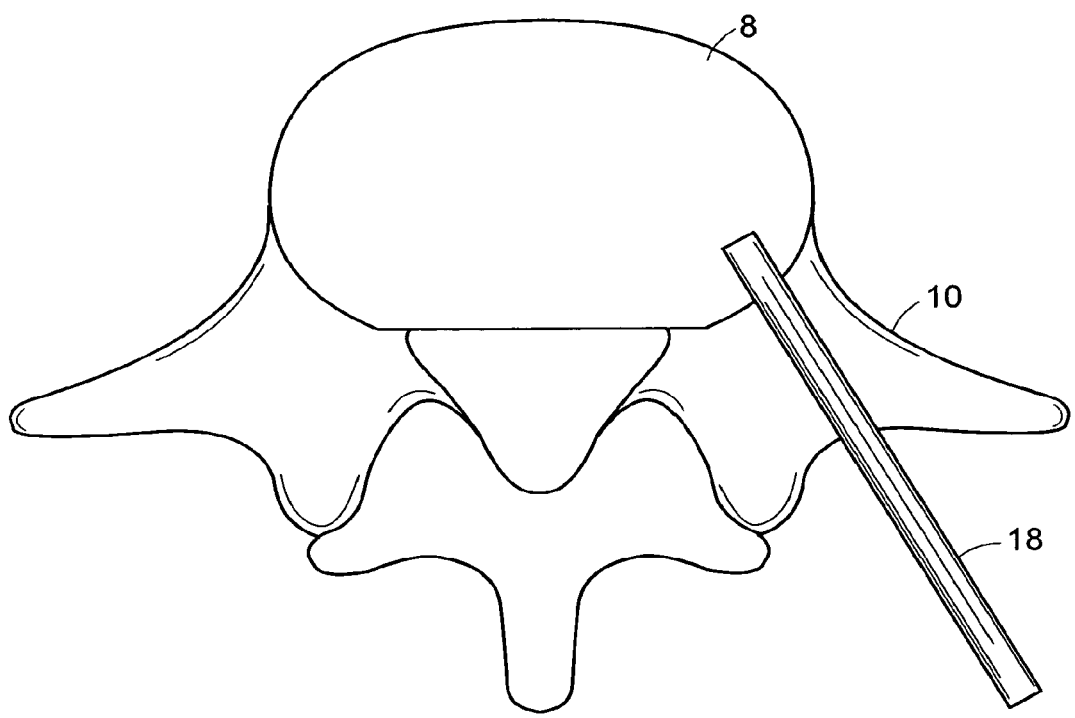
Figure 4A:
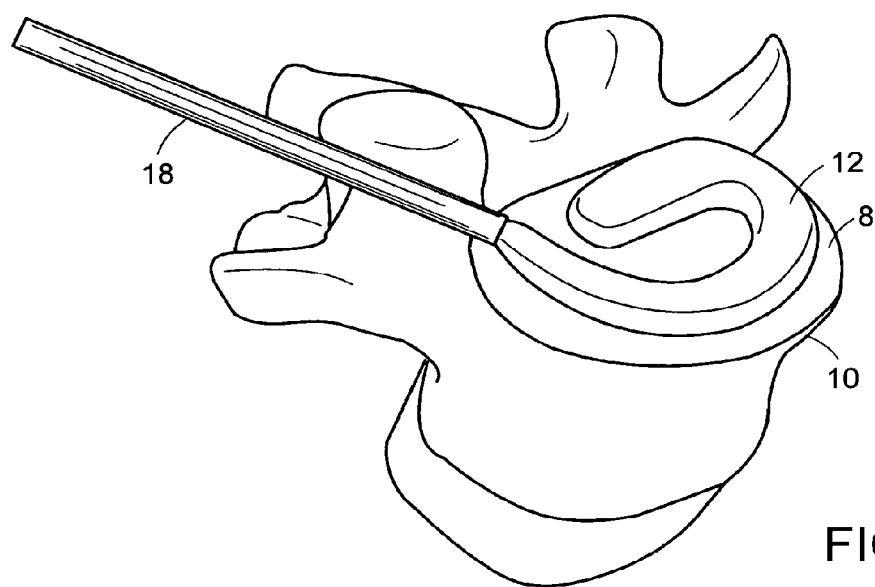
FIG. 4 (a) and FIG. 4 (b) show a perspective and a top view, respectively, of a preferred method of the deployment of an inflatable device into the disc space through the cannula.
Figure 4B:
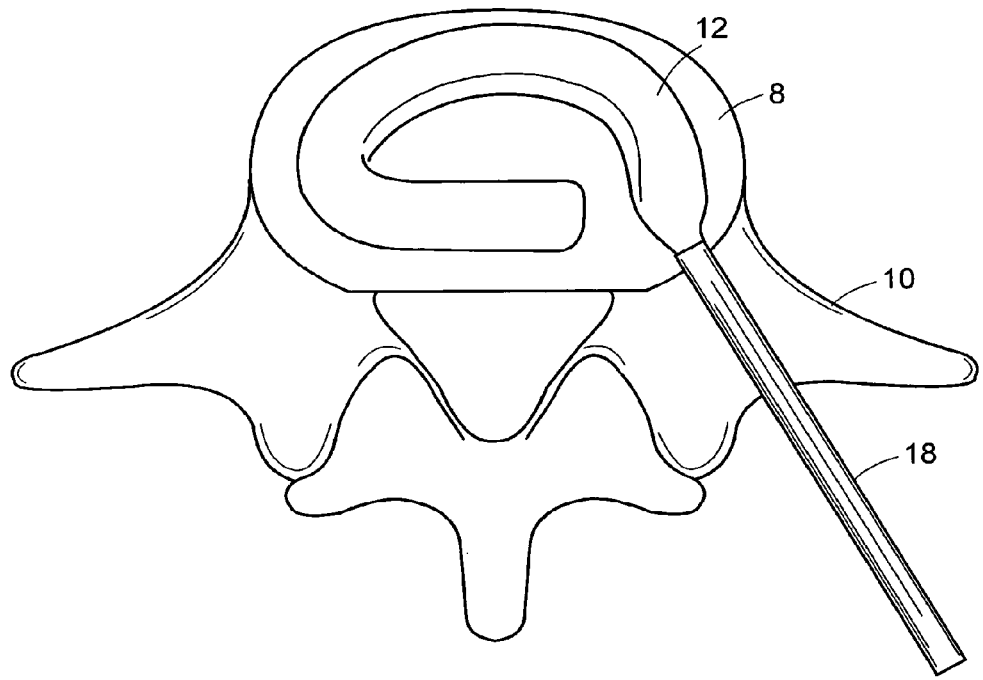

In some embodiments, the load bearing composition is delivered into an inflatable device (such as a balloon) previously placed in the disc space. Now referring to FIGS. 3 (a) and (b), in one preferred method, a cannula 18, having an inner diameter of no more than 6 mm, is inserted into the disc space. Next, and now referring to FIGS. 4 (a) and (b), the inflatable device 12 is deployed through the exit opening of the cannula 18 and the flowable load bearing composition is introduced into the inflatable device at a pressure and volume suitable to expand the inflatable device and distract the disc space.

The fixed shape of the expanded device allows the surgeon to predetermine the shape of the flowable material and simply fill the device with the flowable material. The device substantially prevents unwanted flow of the material. The prevention of unwanted flow desirably prevents the material from damaging important surrounding structures such as the spinal cord, aorta and vena cava. Also, the inflatable device can be tailored to fill any portion of the disc space.

Further, the present inventors believe that inclusion of an inflatable balloon in a strut can assure that the opposing trends of degradation of bioabsorbable materials and new bone growth will result in fusion of the vertebrae in a position approximating the natural angle between two adjacent vertebrae. If the balloon is made of a resorbable, water-impermeable material, the balloon will effectively shield the load-bearing composition from water during the initial stages of fusion and so delay the onset of hydrolysis and degradation of the load-bearing material. Preferably, the balloon begins to degrade within about 1-2 months after fusion of the osteobiologic composition, thereby allowing the load-bearing material it contains to slowly degrade and grow bone.

In some preferred embodiments, the distraction of the disc space is accomplished by an inflatable, yet rigid, balloon or bladder. The balloon can be delivered in deflated form to the interior of the annulus and there inflated in order to distract the disc space and provide a region for the delivery of biomaterial. The balloon is preferably of sufficient strength and of suitable dimensions to distract the space to a desired extent and to maintain the space in distracted position for a period of time sufficient for the biomaterial to be delivered and, optionally, to harden.

One of the primary functions of the balloon is to influence or control the shape of the hardenable material, following injection therein. The implantable balloon is not normally required to restrain pressure over an extended period of time. Thus, a greater design flexibility may be permitted, as compared to conventional angioplasty or other dilatation balloons. For example, the balloon may be porous, either for drug delivery as has been discussed, or to permit osteoincorporation and/or bony ingrowth.

In one particularly preferred embodiment, there is provided a method for fusing an intervertebral disc space, comprising the steps of:
a) using microsurgical techniques to perform a discectomy while preserving an outer annular shell;
b) inserting a deflated balloon into the disc space;
c) injecting a flowable load bearing composition into the deflated balloon (preferably, in an amount sufficient to distract the disc space), and
d) solidifying the flowable strut material.

In one particularly preferred embodiment, there is provided a method for fusing an intervertebral disc space, comprising the steps of:
a) using microsurgical techniques to perform a discectomy while preserving an outer annular shell,
b) inserting a deflated balloon having peripheral struts into the disc space,
c) injecting an osteobiologic component into the deflated balloon in an amount sufficient to inflate the balloon and distract the disc space with the strut component of the balloon.

Optionally, and preferably, the space is distracted by the use of one or more suitable insertable or inflatable devices, e.g., in the form of inflatable balloons. When inflated, such balloons provide rigid walls (e.g., fiber supported) that are sufficiently strong to distract the space. An inflatable device providing sufficient strength and dimensions can be prepared using conventional materials. In one embodiment, the uninflated balloon can be delivered to the center of the annular shell, and there inflated to expand the annular shell and in turn, distract the space. In another embodiment, the uninflated balloon can be delivered to the anterior rim of the annular shell, and there inflated to provide a cavity for the injection of the load bearing flowable material. Preferably, the load bearing composition is injected in an amount sufficient to distract the space.

The inflatable device can be delivered to the disc space by any suitable means, e.g., in deflated form retained within or upon the end of a rigid or semi-rigid rod. Once positioned within the disc, either centrally within the annular shell or along the annular rim, a suitable gas (e.g., nitrogen or carbon dioxide) or the flowable load-bearing material can be delivered through the rod in order to inflate the balloon in situ, in a substantially radial or longitudinal direction. In some embodiments, beads of the load bearing strut material are simply packed into the balloon. The fact that the balloon is properly placed can be confirmed by the use of ancillary means, such as using a C-arm, or by self-effecting means embodied within the balloon itself or its delivery apparatus.

In terms of its component parts, in one preferred balloon delivery system of the present invention there is provided an inflatable device, a motor drive unit, with a remote controller, associated tube sets, a nonscope inflow delivery cannula having independent fluid dynamics pressure and flow rate adjustments, attachments for the flush, vacuum, waste canister, and overflow jars.

Suitable materials for preparing balloons of the present invention may include those that are presently used for such purposes as balloon angioplasty. Suitable materials provide an optimal combination of such properties as compliance, biostability and biocompatability, and mechanical characteristics such as elasticity and strength. Balloons can be provided in any suitable form, including those having a plurality of layers and those having a plurality of compartments when expanded. A useful balloon apparatus will include the balloon itself, together with a delivery catheter (optionally having a plurality of lumen extending longitudinally therewith), and fluid or gas pressure means.

Examples of suitable materials (e.g., resins) for making balloons include, but are not limited to, polyolefin copolymers, polyethylene, polycarbonate, polyethylene terephthalate and ether-ketone polymers such as poly(etheretherketone). Such polymeric materials can be used in either unsupported form, or in supported form, e.g., by the integration of Dacron™ or other fibers. Preferably, the materials of construction of the balloon are resistant to softening or melting at a temperature of at least 80° C., preferably at least 100° C., more preferably at least 250° C. In addition, the balloon (or balloon-like structure) may be made out of any of a wide variety of woven or nonwoven fibers, fabrics, metal mesh such as woven or braided wires, and carbon. Biocompatible fabrics or sheet material such as ePTFE and Dacron™ may also be used.

Balloons can also take several forms, depending on the manner in which the biomaterial is to be delivered and cured. A single, thin walled balloon can be used, for instance, to contact and form a barrier along the interior surface of the remaining annular material. Once positioned, the flowable load bearing component can be delivered and solidified within the balloon to serve as a load bearing strut of the present invention. In such an embodiment, the balloon is preferably of a type that will allow it to remain in position, without undue detrimental effect, between the annular material and the solidified load-bearing component.

Optionally, a balloon can be provided that fills essentially only the central portion of the disc space. In such an embodiment, the balloon can be, for instance, in the shape of a cylinder. Such a balloon can be provided such that its upper and lower walls can be positioned to contact the opposing vertebral bodies, and its side walls will provide sufficient strength to cause, distraction of the space upon inflation. Thereafter, the load-bearing component is delivered to the perimeter of the annular space, i.e., the space between the annular material and the balloon, and there solidified. Optionally, the balloon can be gradually deflated as additional biomaterial is inserted into the space. Then, once the load bearing material is stably positioned, the osteobiologic component is introduced into the balloon, thereby filling the balloon.

In some embodiments, the balloon has metallic wires or other imageable means incorporated into it. Any material that can be seen under fluoroscopy would be acceptable. Potential materials include any metal, metal alloys, or ceramics that could be combined with a polymer. The material can be in the form of wires, a mesh, or particles incorporated into the balloon or on its surface.

In some embodiments, the balloon has an inner surface that is chemically active so as to bond with the balloon filler as it polymerizes. As used herein, a chemical "bond" is said to exist between two atoms or groups of atoms when the forces acting between them are strong enough to lead to the formation of an aggregate with sufficient stability to be regarded as an independent species. As used herein, "chemically active" means capable of forming a chemical bond. In one example, the surface is chemically modified by means such as plasma polymerization. In this case, the balloon is placed in a vacuum chamber and plasma containing a small molecule (an amine for example) is created. The balloon surface is bombarded by the small molecule and the small molecule is chemically attached to its surface. The balloon's surface with its amine groups can then react with the polymer that is injected into the balloon (i.e., an epoxy), forming a device that would have greater fatigue properties since the "composite" of balloon and balloon filler are chemically bonded to one another.

The desired quantities of the load-bearing and osteobiologic components of the present invention are delivered by minimally invasive means to the prepared site. Prior to delivery, these components can be stored in suitable storage containers, e.g., sterile, teflon-lined metal canisters. The flowable components can be delivered, as with a pump, from a storage canister to the delivery cannula on demand. The components can be delivered in the form of a single composition, or can be delivered in the form of a plurality of components or ingredients.

In some embodiments, the inflatable device can be filled with a viscous material that later solidifies to form the strut or osteobiologic component. The viscous material can be a heated polymer (such as a composition containing polycaprolactone), or polymer precursor components (such as the photopolymerizable anhydrides disclosed by A. K. Burkoth, *Biomaterials* (2000) 21:2395-2404, the entire teachings of which are incorporated herein by reference).

In some embodiments, a flowable load bearing composition, such as polycaprolactone, heated to a temperature yielding a viscosity in the range of from about 100 to about 500 cps is injected into the balloon under pressure such as by using a pump and pressure within the range of from about 4 ATM to about 10 ATM or more depending upon viscosity, balloon strength and other design considerations. The pump is run for a sufficient duration and under a sufficient pressure to ensure that the polycaprolactone wets all of the p-dioxanone fibers. This may range from about 10 minutes or more to about an hour, and, in one application where the pump was run at about 5 ATM pressure, requires at least about 1 hour. Specific method parameters may be optimized depending upon the viscosity of the polycaprolactone, infusion pressure, infusion flow rate, density of the packed fibers, and other variables as will be apparent to those of skill in the art in view of the disclosure herein.

It has been reported in the literature that balloons inserted into the disc space may be subject to retropulsion. Therefore, in some embodiments of the present invention, upon expansion, the inflatable device forms an upper surface having a first plurality of teeth projecting outwards from the upper surface. Upon expansion of the device, these teeth will project in the direction of the upper endplate and, upon complete expansion of the device, will engage the endplate to from a secure interlock with the endplate and resist retropulsion.

Preferably, the teeth are made of a stiff resorbable material, such as polyetheretherketone (PEEK). Preferably, the teeth have a height of between 0.5 and 1.5 mm, and have a triangular cross-section.

In some embodiments of the present invention, upon expansion, the inflatable device forms an upper surface formed of a material having a high coefficient of friction. Upon expansion of the device, the high coefficient of friction of the upper and lower surfaces will case a drag upon any movement of the upper surface and therefore keep the device in place and resist retropulsion.

Preferably, the upper and lower surfaces of the inflatable device are made from a material selected from a group consisting of polyether block copolymer (PEBAX), ABS (acrylonitrile butadiene styrene); ANS (acrylonitrile styrene); Delrin®; PVC (polyvinyl chloride); PEN (polyethylene napthalate); PBT (polybutylene terephthalate); polycarbonate; PEI (polyetherimide); PES (polyether sulfone); PET (polyethylene terephthalate); PETG (polyethylene terephthalate glycol), high and medium melt temperature: polyamides, aromatic polyamides, polyethers, polyesters, Hytrell®, polymethylmethacrylate, polyurethanes: copolymers, EVA (ethylene vinyl acetate) or ethylene vinyl alcohol; low, linear low, medium and high density polyethylenes, latex rubbers, FEP, TFE, PFA, polypropylenes, polyolefins; polysiloxanes, liquid crystal polymers, inomers, Surlins, silicone rubbers, SAN (styrene acrylonitrile), nylons: 6, 6/6, 6/66, 6/9, 6/10, 6/12, 11, all PEBAXs 12; polyether block amides; thermoplastic elastomers and the like.

In some embodiments, the vertebral endplates opposing the disc space are roughened. The roughening provides hills and valleys into which a flowable polymer can flow and harden, thereby forming a mechanical interlock between the device and the bony surface and resisting retropulsion.

The roughening can be provided mechanically (as with a curette), or chemically (as by an acid), or by an energy-transmitting device (as with an ablation unit preferably assisted with hyperconductive fluid, such as hypertonic saline).

In some embodiments, the flowable polymer forming a mechanical interlock can be a separate layer. In others, the flowable polymer can be a component of the strut. In others, the flowable polymer can be a component of the osteobiologic composition.

In some embodiments, the strut portion of the device can have an outer layer of a scaffold material appropriately seeded with osteogenic factors and/or growth factors to produce quick bone ingrowth, thereby effectively locking the strut in place.

In some embodiments, an outer layer of a scaffold material appropriately seeded with osteogenic factors and/or growth factors can also be applied to a balloon component of the osteobiologic component. The seeding again produces quick bone ingrowth, thereby effectively locking the osteobiologic component in place.

Balloons of the present invention can be made using materials and manufacturing techniques used for balloon angioplasty devices. U.S. Pat. No. 5,807,327 by Green, the entire teachings of which are incorporated herein by reference, (hereinafter "Green") discloses balloons that may be used in the present invention. The materials disclosed by Green for the formation of the balloon include tough non-compliant layer materials (col. 8, lines 18-36) and high coefficient of friction layer materials (col. 8, lines 42-54).

Figure 5A:
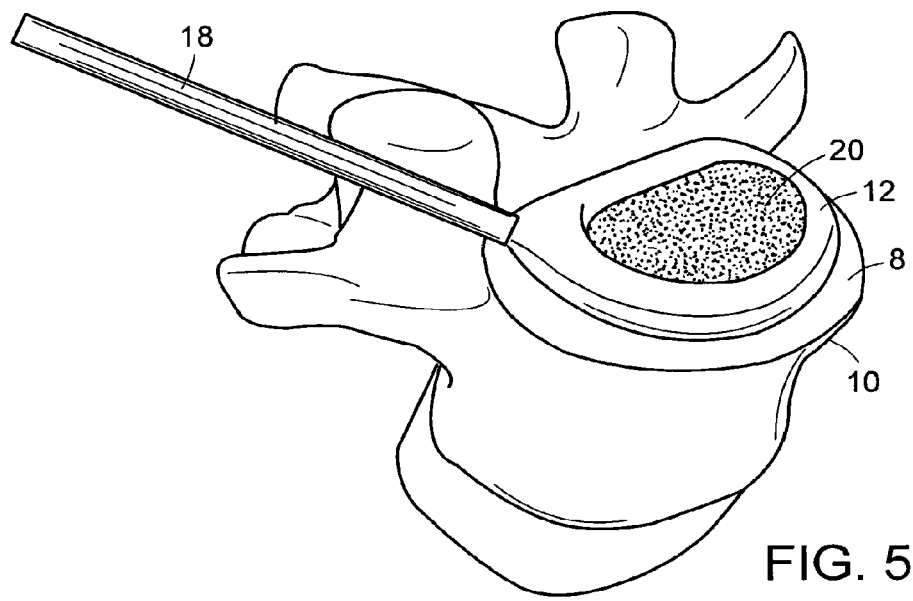
FIG. 5 (a) and FIG. 5 (b) show a perspective and a top view, respectively, of an embodiment of the present invention wherein the device comprises a generally toroidal balloon and the osteobiologic component is injected into an open cavity defined by the outer surface of the generally toroidal balloon.
Figure 5B:
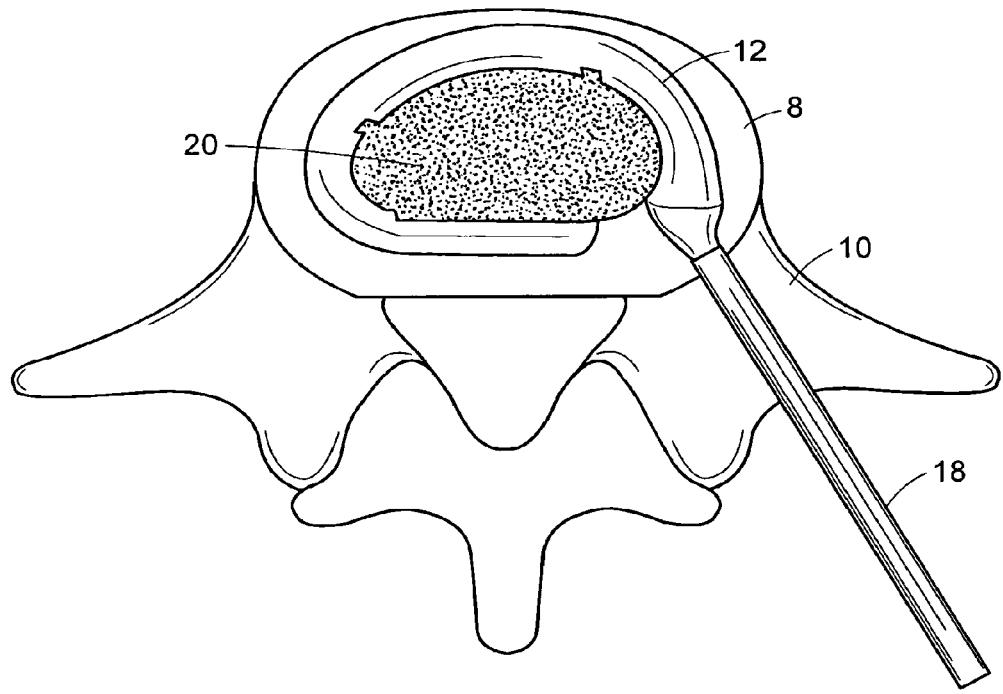

Now referring to FIGS. 5 (*a*) and (*b*), in some embodiments, the load-bearing component is delivered into the disc space through an inflatable balloon 12, and the osteobiologic component 20 is freely injected. This embodiment is desirable because the balloon 12 can act as a barrier to hydrolysis of the load-bearing component, thereby increasing the longevity of the load-bearing component. In contrast, the absence of the balloon covering the osteobiologic component may be desirable in instances in which it is desirable to immediately begin the bone growth process.

This embodiment may also be desirable in instances in which the load-bearing component comprises a cross-linkable composition, and the surgeon desires to provide a barrier between the patient's tissue and the precursors during the reaction of the precursors.

Figure 6A:
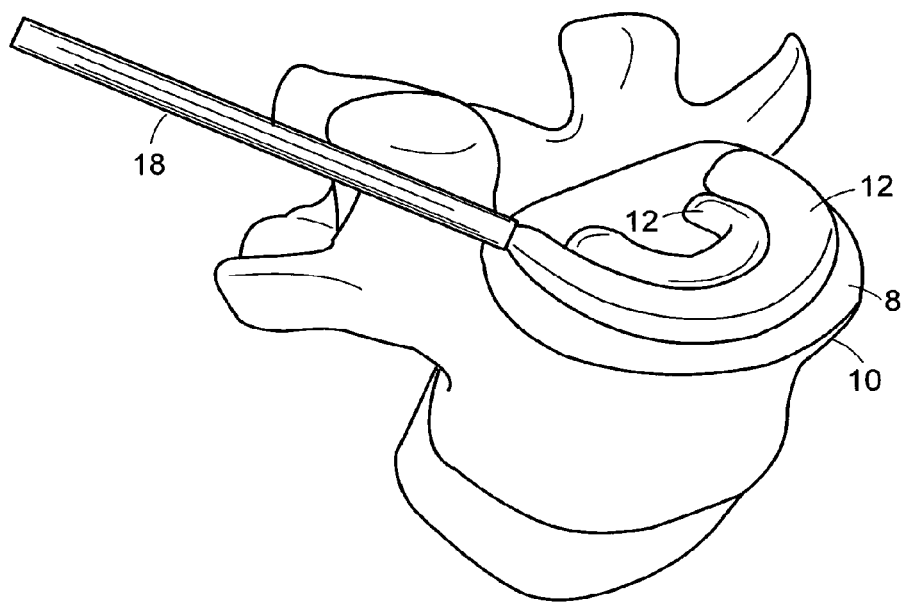
FIG. 6 (a) and FIG. 6 (b) show a perspective and a top view, respectively, of an embodiment of the present invention comprising more than one balloon.
Figure 6B:
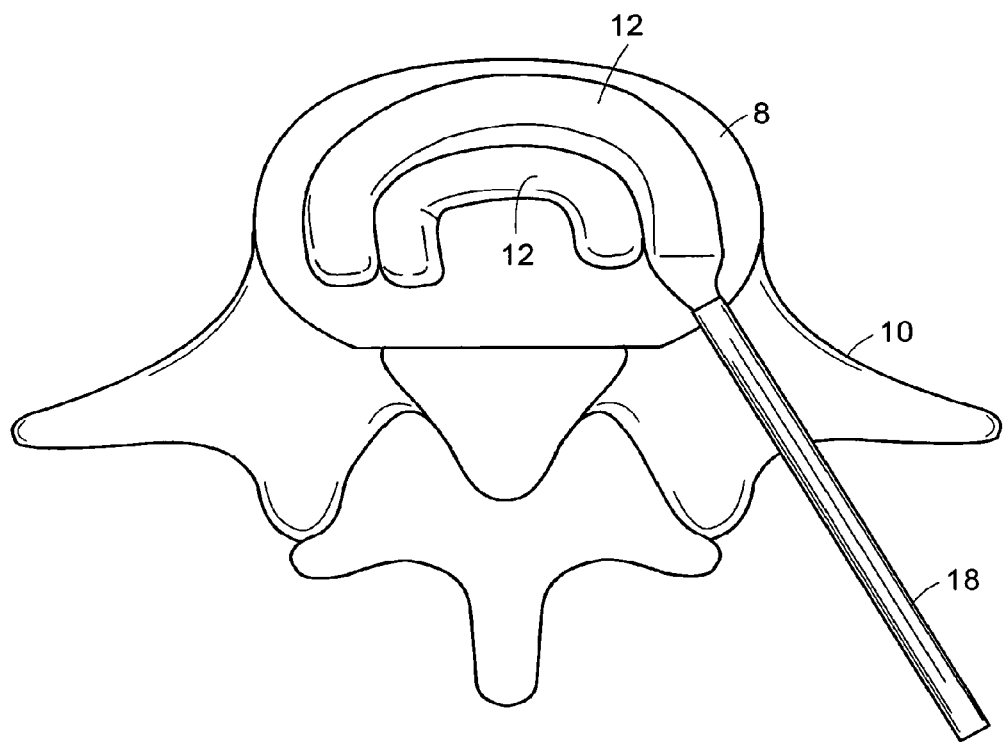

Now referring to FIGS. 6 (*a*) and (*b*), in some embodiments, both the load bearing and the osteobiologic components are delivered into the disc space using a device comprising two separate inflatable balloons 12. This embodiment is desirable in instances in which both the annulus fibrosis has been functionally breached, and there is a concern that flowable materials would flow from the disc space and through the breach and into the remainder of the body. In this embodiment, it is preferred that the balloon containing the osteobiologic material be at least semi-permeable to nutrients and preferably resorbable. As used herein, the term "semipermeable" refers to a material that is non-permeable to the flowable materials described above yet permeable to important water and nutrients to support bone growth therein. Suitable semi-permeable materials include both porous and non-porous polymeric constructs such as films, fabrics (woven and non-woven) and foams.

In some embodiments, both the load bearing and the osteobiologic components are delivered into the disc space through the same inflatable device.

Figure 7A:
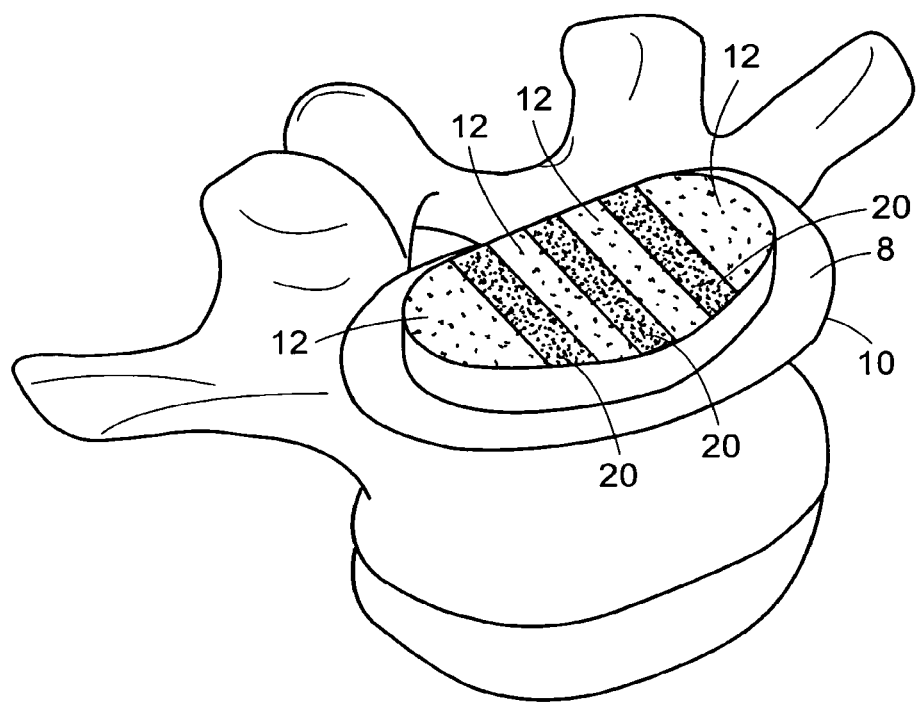
FIG. 7 (a) and FIG. 7 (b) show a perspective and a top view, respectively, of another embodiment of the present invention comprising more than one balloon.
Figure 7B:
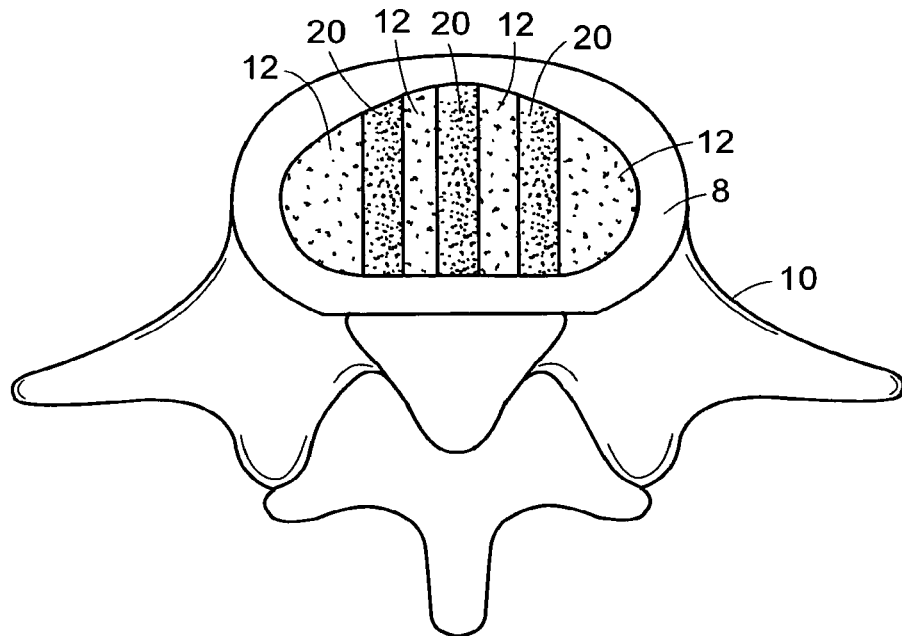

Now referring to FIGS. 7 (*a*) and (*b*), another embodiment of the device and method of the present invention is shown wherein the device comprises at least two inflatable balloons 12. In this embodiment, the load-bearing component is delivered into the disc space through at least two inflatable balloons 12 and the osteobiologic component 20 is freely injected into the disk space using the space between the balloons.

In some embodiments, the osteobiologic component is delivered into the disc space through an inflatable device, and the load-bearing component is freely injected. This embodiment may be desirable in instances in which the osteobiologic component comprises an in situ hardenable composition such as a calcium containing cement, or a crosslinkable polymer such as polypropylene fumarate), polyanhydride, or polyoxaester, and the surgeon desires to cordon off the patient from the precursors during their reaction. In this embodiment, it is further preferred that the balloon containing the osteobiologic material be at least semi-permeable to nutrients and preferably resorbable. This embodiment may also be desirable in instances in which the load-bearing composition comprises growth factors and the surgeon desires to immediately begin the bone growth process in the load-bearing component.

In some embodiments, the load-bearing component is delivered into the disc space through an inflatable device, and the osteobiologic component is freely injected. This embodiment may also be desirable in instances in which the annulus fibrosis in essentially intact and the surgeon desires to immediately begin the bone growth process in the load-bearing component.

In some embodiments, the inflatable device comprises a single peripheral wall having an upper and lower surface, upper and lower walls, and a cavity formed therebetween. For the purposes of the present invention, this shape of this embodiment is referred to as a "puck". The peripheral wall and upper and lower walls of the puck could be designed so as to be percutaneously deliverable through a cannula having an inside diameter of between 0.5 and 18 mm, preferably no more than 4 mm.

In one embodiment, the peripheral wall of the puck is designed to be load bearing when the inflatable device is disposed in its inflated position. Preferably, the peripheral wall is made of a shape-memory metal, such as Nitinol, or a thin film alloy.

In some embodiments, the periphery of the balloon is reinforced with fibers. In some embodiments thereof, the peripheral wall comprises polymer fibers. These fibers can be made into a weave that is sufficiently flexible (in the longitudinal direction of the fiber) to pass through the cannula and expand into the expanded state. Typically, these fibers have high tensile strengths so that they can very efficiently accommodate the problematic hoop stresses that may be transferred from the osteobiologic component contained within the middle annulus of the balloon.

Various patterns of reinforcement of the peripheral sidewalls with the fibers are contemplated. In one embodiment, the fibers form X-shaped cross-hatching pattern. In another embodiment, the fibers form a continuous wave-like pattern having peaks and troughs, where said peaks and troughs approach upper and lower surfaces.

In one embodiment, the walls of the device are reinforced by an internal frame forming a polygonal structure having sides on the upper, lower and peripheral surfaces.

In some embodiments, the peripheral reinforcement is made of a resorbable polymer fiber.

The upper and lower walls of this puck embodiment are designed to initially accept and contain the osteobiologic component that is flowed into the puck cavity. Accordingly, the upper and lower walls should be at least semi-permeable so as to contain the osteobiologic component. In preferred embodiments, the upper and lower walls are made of a resorbable material that quickly resorbs, thereby exposing the contained osteobiologic material to blood flowing from the decorticated endplates.

In some embodiments, this absorbable material has an elastomeric quality. This elastomeric quality allows the resorbable upper and lower walls to be delivered through the cannula, and flatten upon device expansion. In preferred embodiments, this elastomeric polymer is selected from the materials disclosed in U.S. Pat. No. 6,113,624 by Bezwada, the entire teachings of which are incorporated herein by reference (hereinafter "Bezwada"). In other embodiments, this absorbable material is not elastomeric, and is preferably made of a thin film metal alloy or a braided metal alloy.

Figure 8A:
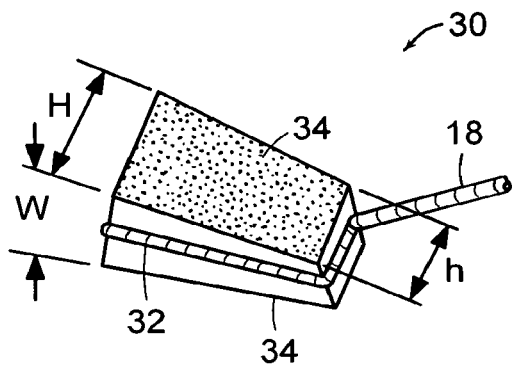
FIG. 8 (a) and FIG. 8 (b) show an embodiments of the present invention comprising an arcuate inflatable balloon with reinforced walls.
Figure 8B:
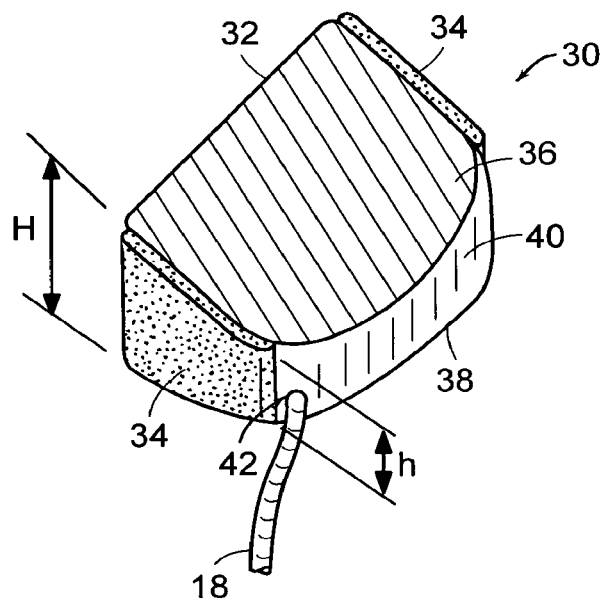
Figure 9A:
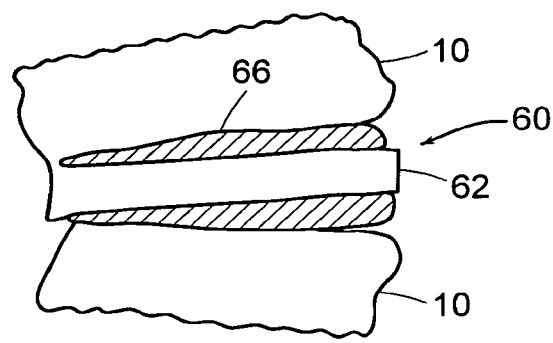
FIGS. 9 (a) through (d) show an embodiment of an inflatable device and a method of inserting an inflatable device of the present invention into the disc space, wherein a pair of semi-circular flexible members is used for guiding the device.
Figure 9B:
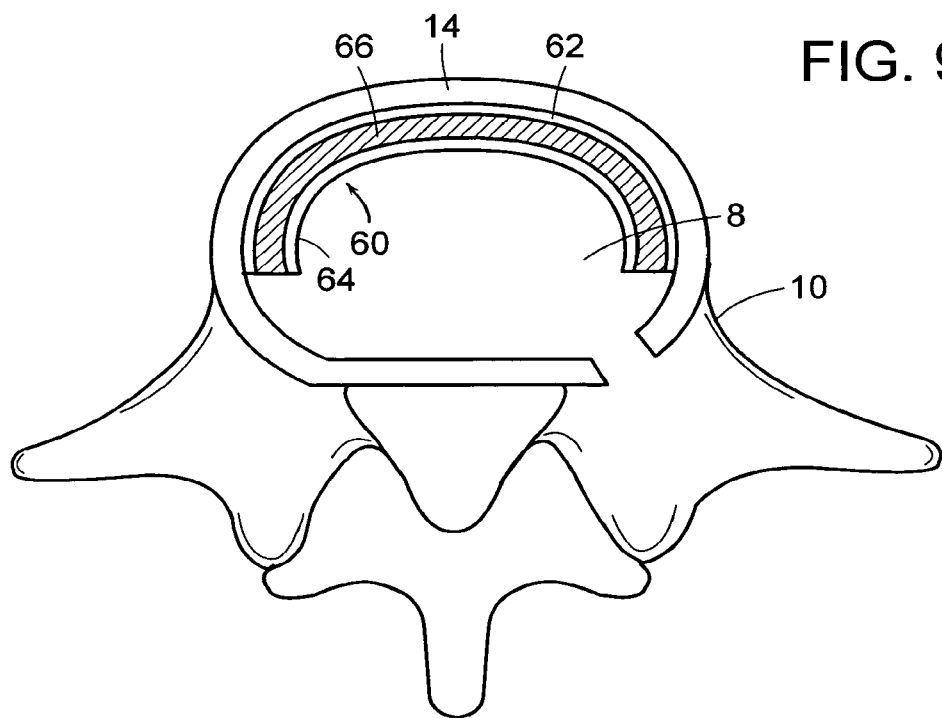
Figure 9C:
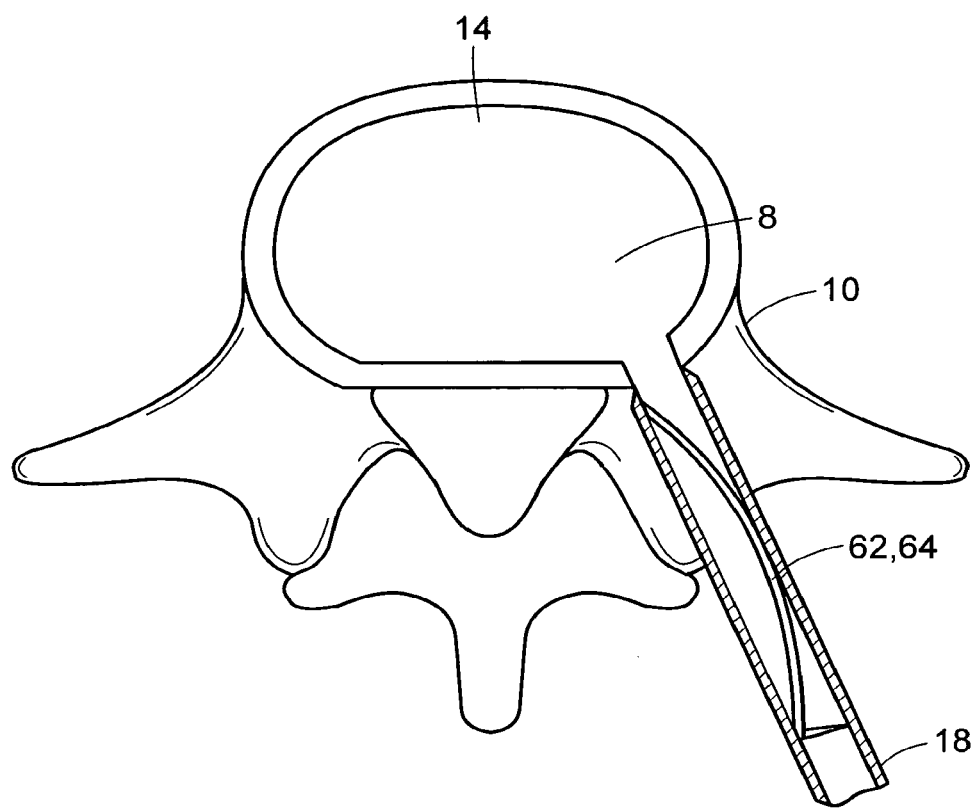
Figure 9D:
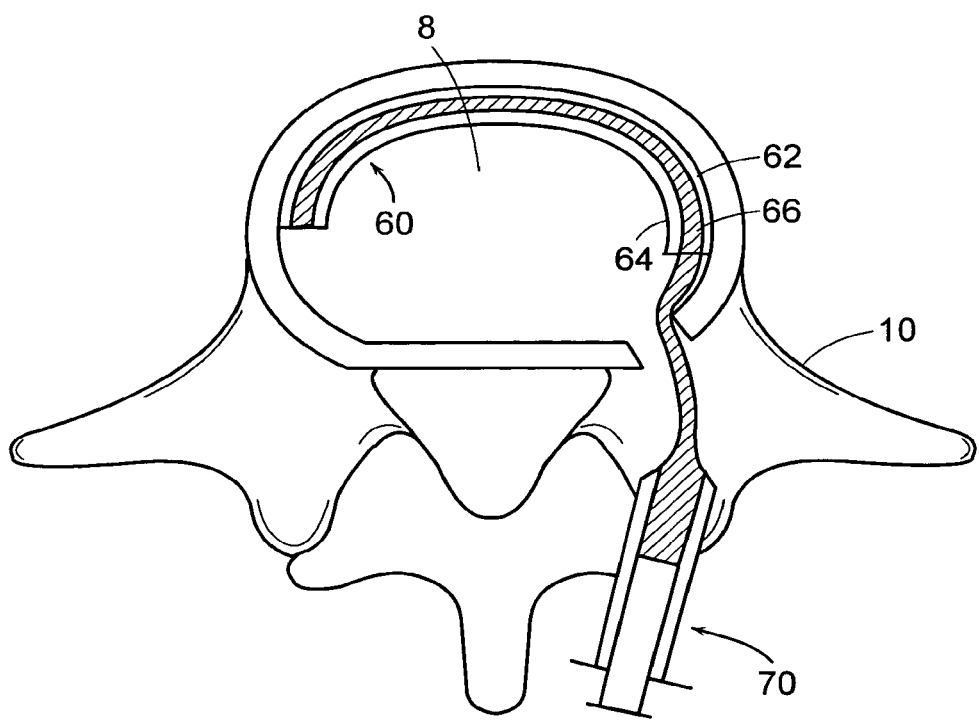

Now referring to FIGS. 8 (*a*) and 8 (*b*) there is provided a device 30 of the present invention comprising an inflatable portion 32 that includes an arcuate inflatable balloon.

Now referring to FIG. 8 (*a*), in its pre-deployed state, the inflatable portion 32 of the device 30 is conveniently repeatedly folded upon itself, thereby decreasing the size of the device 30 and allowing for minimally invasive insertion into the disc space. During insertion into the disc space, the device 30 is preferably inserted in the sandwich orientation as shown in FIG. 8 (*a*) wherein the structural walls 34 are disposed essentially parallel to the vertebral endplates. The sandwich orientation allows height H of the structural walls 34 to meet or exceed the disc space height, while the folded width W does not exceed the disc space height.

Now referring to FIG. 8 (*b*), after insertion into the disc space, fluid is flown into the inflatable portion 32 of the device 30, thereby expanding the device 30 into the configuration as shown. The height H of the structural walls 34 is sufficient to restore the natural height of the disc space. After the device 30 distracts the disc space, the cavity, formed by the expanded portion 32, is filled by an osteobiologic component.

The structural walls 34 of this embodiment are preferably attached to the inflatable portion 32 by an adhesive. The structural walls 34 should be designed so that the width W and the strength and modulus of the material of construction allow for both support of the disc space and bony fusion through the osteobiologic component.

In some embodiments, the height H of the structural wall 34 is at least equal to the height of the natural disc space. This condition desirably restores the height of the disc space when the inflatable portion 32 is expanded. In some embodiments, the height H of the anterior portion of the wall 34 is greater than the height h of the posterior portion of the wall 34. This condition desirably provides a lordotic effect upon expansion of the inflatable portion 32.

In some embodiments, the walls 34 are made of allograft bone, and preferably comprise cortical bone. In others, the walls are made of a synthetic resorbable polymeric material. In some embodiments, the walls may be sufficiently porous to provide an effective scaffold, thereby allowing bony fusion therethrough.

In some embodiments, the wall component 34 of this embodiment is made of bone graft. In alternative embodiments, component 34 comprises additional inflatable portions. After insertion into the disc space, a load bearing composition may be flowed into the cavities of these additional inflatable portions, thereby expanding these additional inflatable portions and eventually producing the desired dimensions of the walls 34.

In some embodiments, each wall 34 is translaterally oriented in the expanded device. In this condition, a first wall supports essentially the anterior portion of the opposing cortical rims, while the second wall supports essentially the posterior portion of the opposing cortical rims, so that one of these walls will essentially bear the entire load during flexion and the other wall will bear essentially the entire load during extension. Preferably, these walls have a length L corresponding to the anterior and posterior aspects of the cortical rim.

The inflatable portion 32 has upper and lower surfaces 36 and 38 for contacting the adjacent vertebral endplates, a peripheral side surface 40 connecting the upper and lower surfaces 36 and 38, and an opening 42 in the peripheral side surface 40. Upon a flow of fluid through the opening 42 from a cannula 18, the inflatable portion 32 is expanded and surfaces 36, 38 and 40 are pushed apart sufficiently to form an internal cavity suitable for containing an osteobiologic component. Because the osteobiologic component retained within this cavity is preferably at least semipermeable in order to provide bony fusion, the upper and lower surfaces 36 and 38 of the inflatable portion 32 preferably do not act as barriers to bony fusion. Accordingly, it is preferred that the upper and lower surfaces 36 and 38 are either porous (preferably, semipermeable) or quickly resorbable. Preferably, the upper and lower surfaces 36 and 38 are made of a material that resorbs within 7 days, preferably 3 days, preferably one day. Examples of fast-resorbing materials include denatured collagen, polysaccharide-based materials such as starch and oxidized regenerated cellulose, and hydroxylated lactide-glycolide copolymers. In some embodiments, the opening in the side surface 40 is formed closely adjacent to the structural wall 34, positioned anteriorly on a vertebral endplate.

In some embodiments, the inflatable device 30 of this embodiment has a configuration designed to match the geometry of the disc space, and is selected from the group consisting of an anterior lumbar interbody fusion (ALIF) configuration, a posterior lumbar interbody fusion (PLIF) configuration, a vertebral body replacement (VBR) configuration, and an anterior cervical discectomy and fusion (ACDF) configuration.

By reducing the effective size of the device 30, this embodiment of the present invention desirably minimizes the access window required for insertion of intervertebral devices. By providing anatomically appropriate structural walls 34, the device 30 provides a stable environment for the muskuloskeletal growth factors to develop.

Now referring to FIGS. 9 (*a*) and (*b*), one embodiment of an inflatable device of the present invention is shown. The device 60 comprises an outer side-wall component 62, an inner side-wall component 64, and a balloon 66 disposed between and attached to said inner and outer wall components. The short cranial-caudal height of the inner and outer walls allows for the device to be inserted into the disc space without having to distract the disc space prior to insertion. Subsequent filling of the balloon with an in-situ hardenable, load-bearing material causes the balloon to expand beyond the cranial and caudal margins of the sidewalls, thus providing the necessary distraction of the disc space. Furthermore, the sidewalls prevent expansion of the balloon such that the thickness of the device is minimized upon inflation. Minimized wall thickness is important for ensuring maximum area for bone growth (fusion) between the adjacent vertebrae. In some embodiments, the footprints of the outer and inner side-wall components 62 and 64 represent substantially equal arcs of two concentric circumferences. This allows placing device 60 along the periphery of the anterior portion 14 of a vertebral endplate 8 and filling a cavity therewithin with a load bearing material.

In some embodiments of device 60, the outer and inner walls 62 and 64 are made of a flexible plastic such as poly(ethyleneterephthalate), a superelastic metal such as Nitinol, or a flexible material/geometry combination, whereby each wall can be deformed into a relatively elongated shape for delivery to the disc space through a cannula 18. The sidewalls are sufficiently rigid to guide the device into the desired location in the disc space but sufficiently flexible to allow delivery through the cannula. Referring to FIG. 9 (*c*), during the insertion of the device 60, upon release from the cannula 18, components 62 and 64 can then take on the desired arcuate shape. Referring to FIG. 9 (*d*), subsequent to insertion, the device 60 is expanded by injecting a load-bearing component, an osteobiologic component or a combination thereof into a cavity formed by the components 62, 64, and 66. Any suitable injection means can be used, for example, a syringe pump 70.

The above characteristics of components 62 and 64 ensure that the cavity produced between side walls 62, 64 can be filled so that the device 60 distracts the disc space and can also create a wedge shape for creating or restoring healthy curvature of the spine.

Figure 10A:
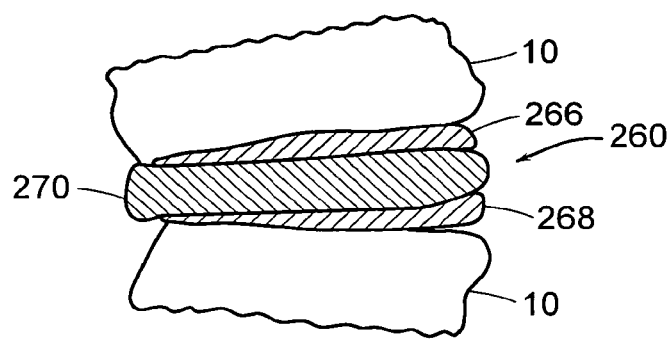
FIGS. 10 (a) and 10 (b) represent plan and lateral views, respectively, of an embodiment of an inflatable device of the invention whereby a pair of semi-circular flexible upper and lower wall components, which can be used for guiding the device, are joined by an inflatable balloon.
Figure 10B:
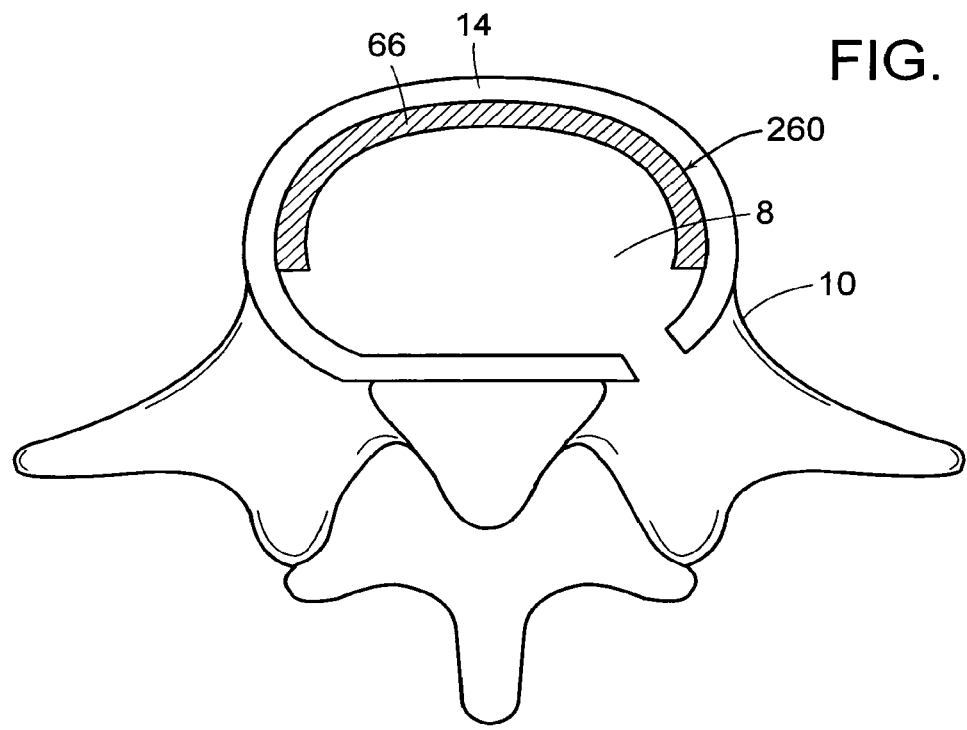

An alternative embodiment of inflatable device of the present invention is shown in FIGS. 10 (*a*) and (*b*). Device 260 comprises an upper wall component 266 and a lower wall component 268 joined by an inflatable balloon 270. In some embodiments, the footprints of the upper and lower wall components 266 and 268 represent substantially equal arcs of two concentric circumferences. This allows placing device 260 along the periphery of the anterior portion 14 of a vertebral endplate 8 and filling a cavity therewithin with a load bearing material.

In some embodiments of device 260, the upper and lower wall components 266 and 268 are made of a superelastic material such as Nitinol, or a flexible material/geometry combination, whereby each wall can be deformed into a relatively elongated shape for delivery to the disc space through a cannula 18. Operationally, device 260 is similar to device 60. Insertion of device 260 can be accomplished in a manner depicted in FIG. 9 (*c*). Upon release from cannula 18, components 266 and 268 can then take on the desired arcuate shape. Subsequent to insertion, device 260 is inflated by injecting a load-bearing component, an osteobiologic component or a combination thereof into balloon 270. Any suitable injection means can be used, for example a syringe pump.

Preferably, balloon 270 is semi-permeable. In preferred embodiments, balloon 270 is made of a material that quickly resorbs, thereby exposing the contained osteobiologic material to blood flowing from the decorticated endplates.

Generally, the strut is deliverable through a cannula having an inside diameter of between 3 mm and 18 mm, preferably between 4 mm and 12 mm, more preferably between 5 mm and 10 mm.

In some embodiments in which the surgeon desires to minimize the size of the incision, the strut is preferably deliverable through a cannula having an inside diameter of between 0.5 mm and 6 mm, preferably between 1 mm and 4 mm, more preferably between 2 mm and 3 mm.

Preferably, the upper and lower surfaces of the upper and lower walls, respectively, have teeth that prevent excessive movement of the strut after implantation.

Figure 11A:
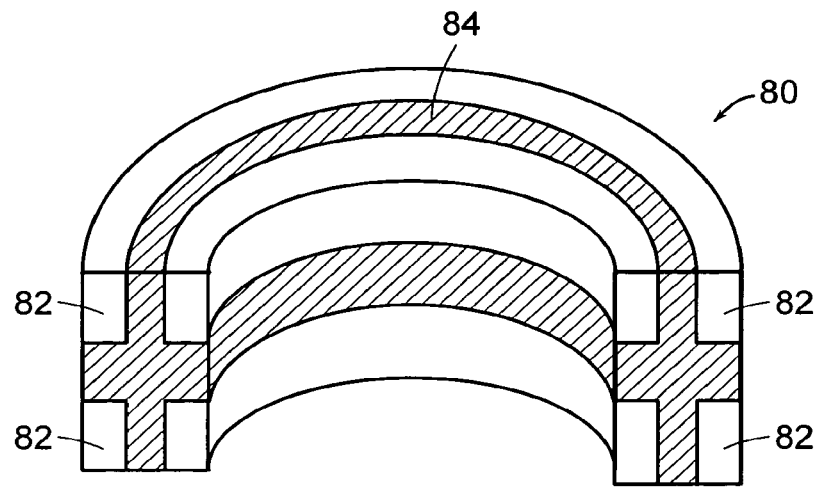
FIGS. 11 (a) and (b) show an embodiment of the present invention wherein the device comprises four semi-circular flexible components for guiding the inflatable device into the disc space.
Figure 11B:
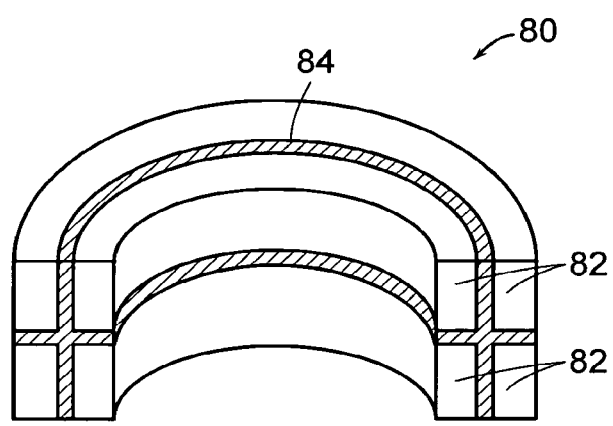

Now referring to FIGS. 11 (*a*) and (*b*), the device 80 comprises four rail components 82 wherein the footprints of the rail components 82 represent substantially equal arcs of two concentric circumferences. Components 82 are joined by an inflatable balloon 84 such that the device can be inserted in a collapsed configuration as shown in FIG. 11 (*b*) and then expanded as shown in FIG. 11(*a*) once filled with a load-bearing material to increase disc height and provide thickness for load bearing support.

Figure 12A:
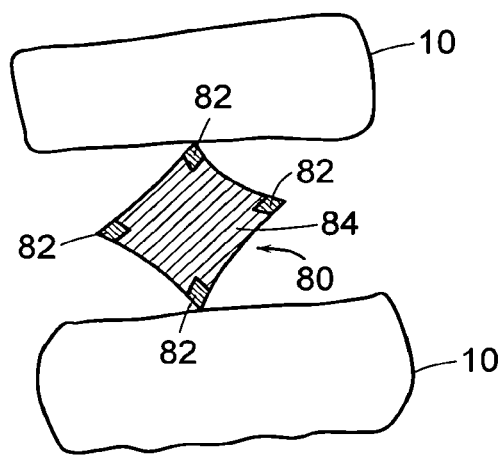
FIGS. 12 (a) and (b) show another embodiment of device of the present invention that includes guiding members.
Figure 12B:
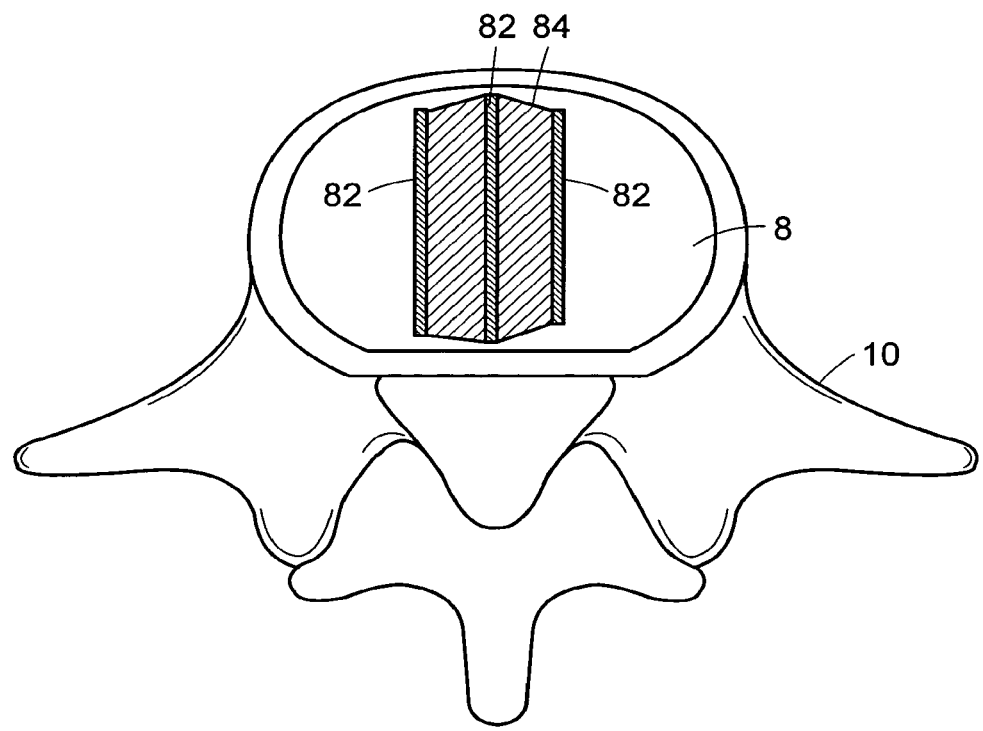
Figure 13A:
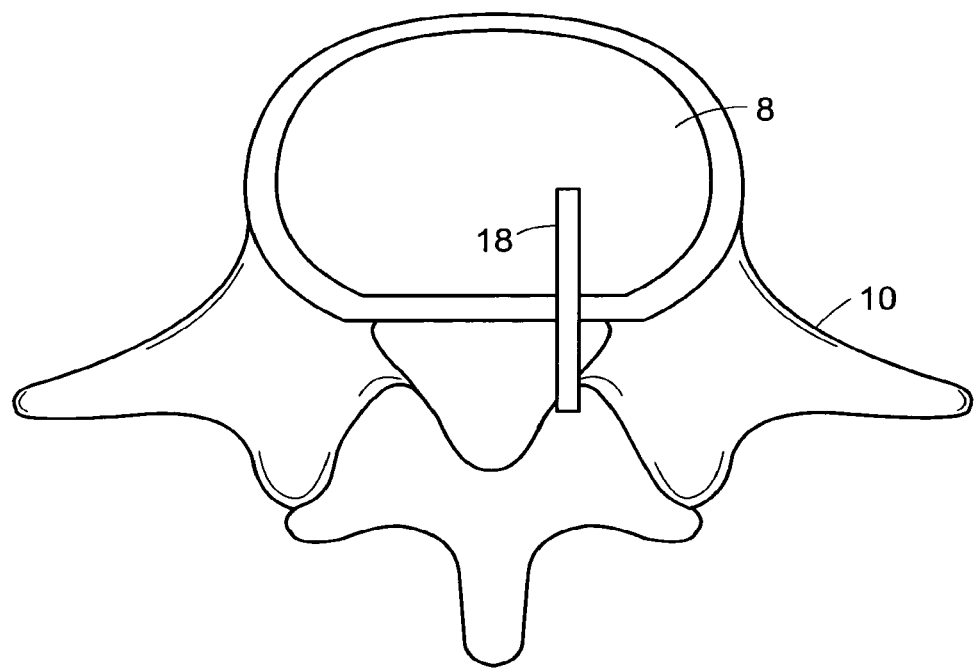
FIGS. 13 (a) through (d) shows a preferred embodiment of the method of the present invention.
Figure 13B:
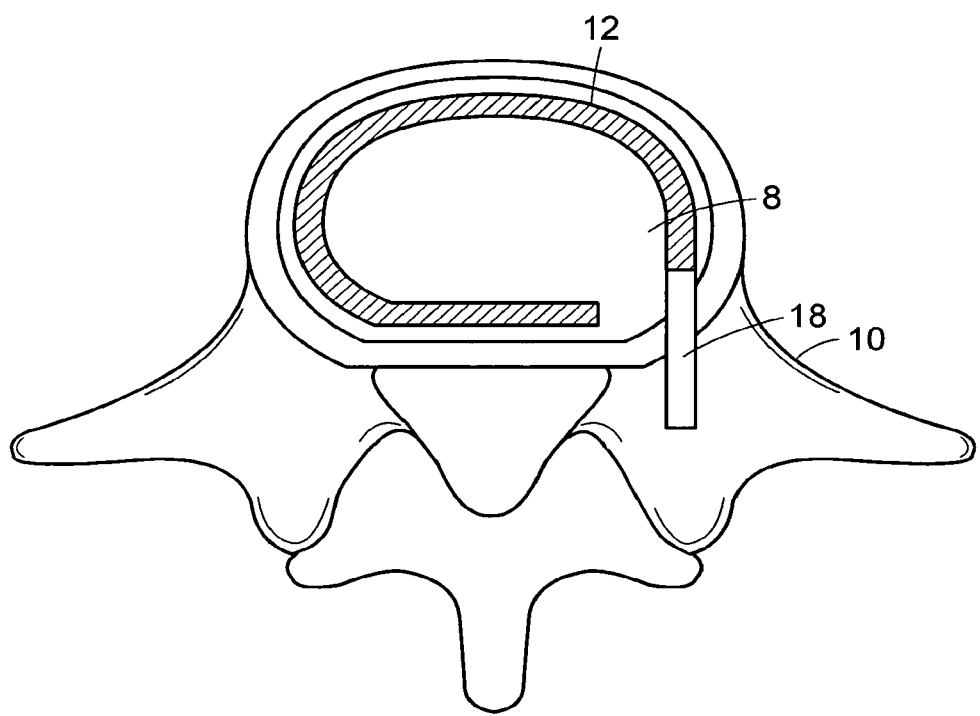
Figure 13C:
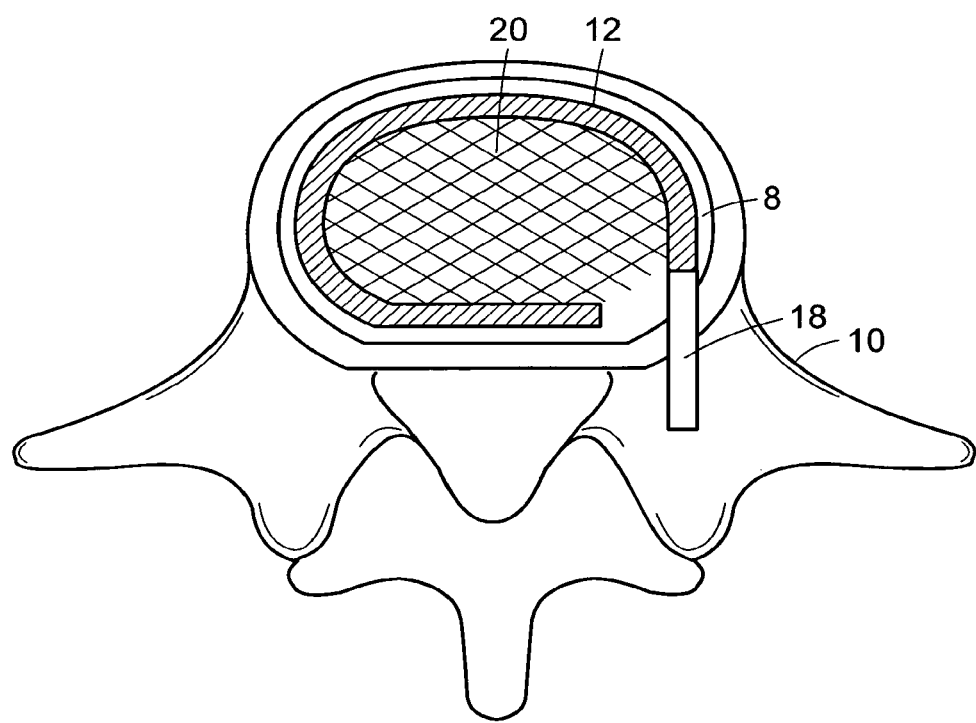
Figure 13D:
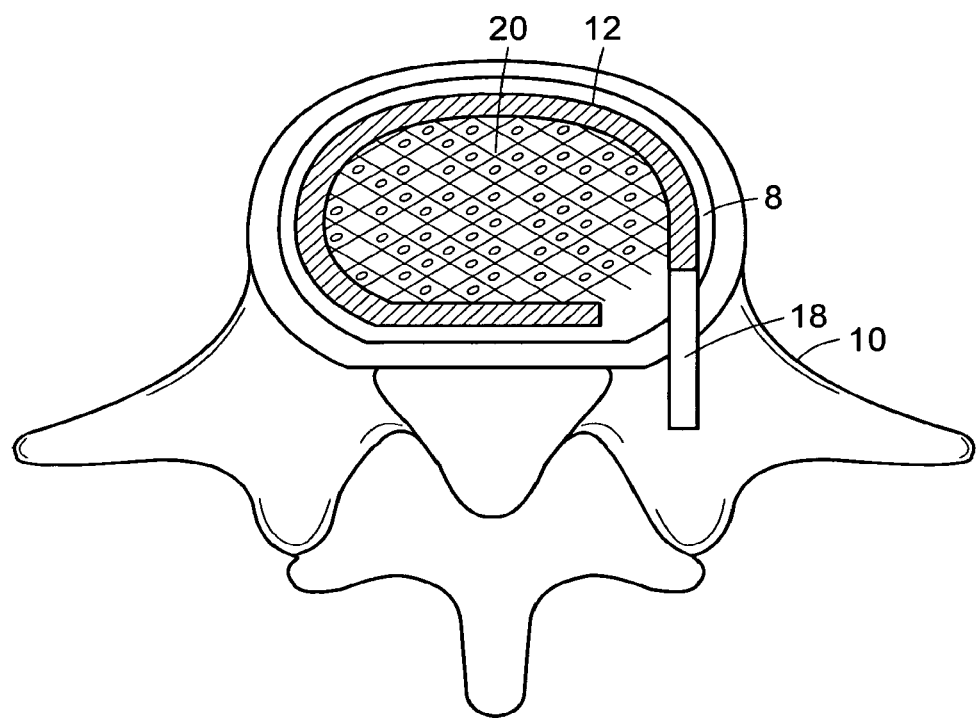
Figure 14A:
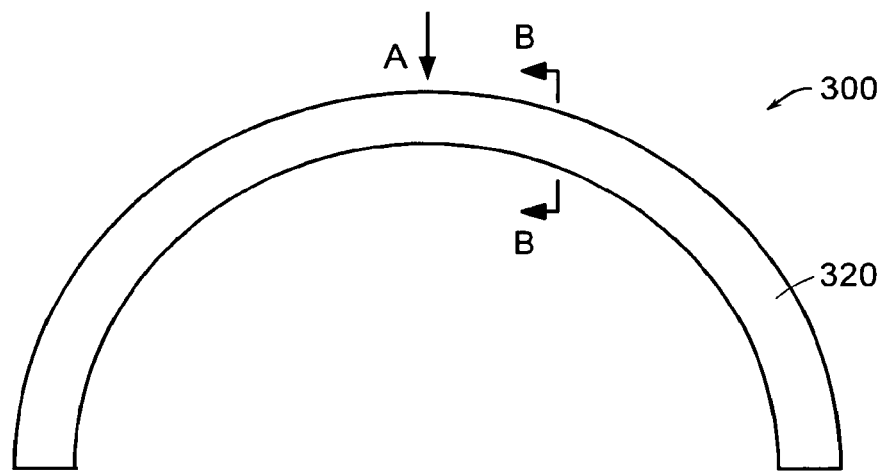
FIGS. 14 (a) and (b) show a top and a lateral view, respectively, of another embodiment of a device of the present invention employing a ramp.
Figure 14B:
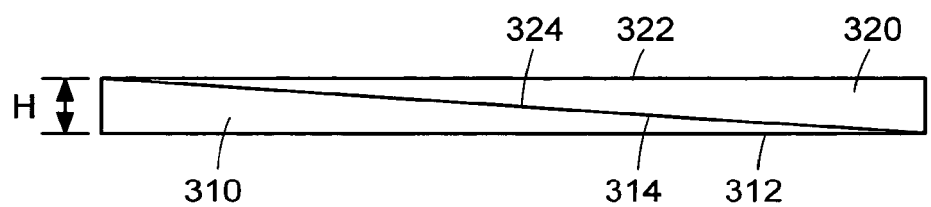
Figure 14C:
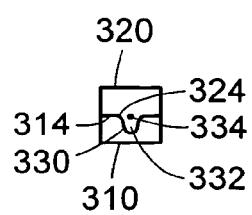
Figure 14D:
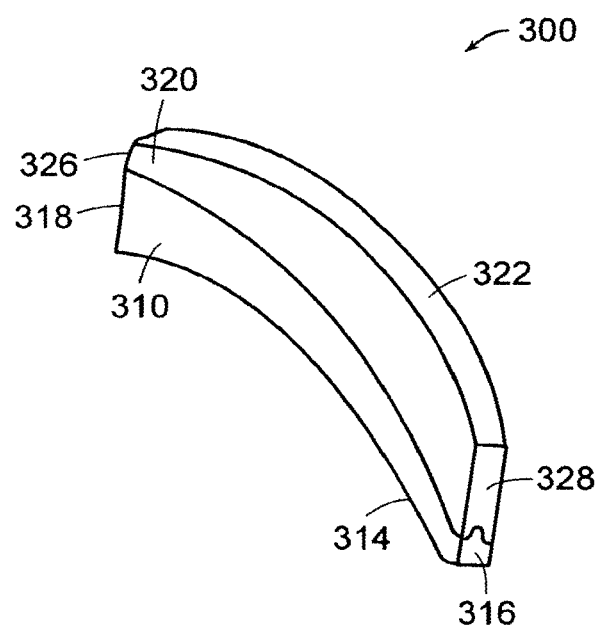

In one embodiment of the present invention, device 80 is shown in FIGS. 12 (*a*) and (*b*). In this embodiment, device 80 is delivered in a generally diamond-shaped configuration, shown in plan view on FIG. 12 (*a*) and in lateral view in FIG. 12 (*b*). In this embodiment, the upper and lower rails 82 will cause slight subsidence of the vertebral body endplates, thus providing stability of the implanted device.

Now referring to FIGS. 13 (*a*) through (*d*) a preferred embodiment of the method of the present invention is shown. As shown in FIGS. 13 (*a*) and 13 (*b*), a cannula 18 is inserted into an intervertebral space. Next an inflatable balloon 12 of a generally toroidal shape is inserted through the cannula 18 into the intervertebral space. The balloon 12 is expanded by directing a load-bearing component into said balloon. Referring to FIG. 13 (*c*), subsequent to balloon expansion, osteobiologic component 20 is injected into the open cavity defined by the outer surface of the balloon 12. Preferably, the osteobiologic component comprises a water-soluble component. Next, the water-soluble component is dissolved, thus forming a porous matrix shown in FIG. 13 (*d*).

In one embodiment of the present invention the load-bearing component is delivered through a balloon, and the osteogenic component is provided in a hydrogel phase of the osteobiologic component. Examples of suitable hydrogels are provided hereinbelow.

In other embodiments, solid components of the strut are inserted into the body percutaneously and assembled in situ to form the strut. In some in situ embodiments, the strut is formed by bonding together two bondable components. Preferably, the bondable materials are selected from the group consisting of heat bondable materials such as polycaprolactone, and polymerizable materials such as polypropylene fumarate) and polyoxaesters including photo-curable materials such as polyanhydrides.

In other embodiments, load-bearing materials in the form of beads is delivered into the inflatable device and packed into the device so as to create a stable strut having an open interstitial porosity. In some embodiments, the beads may be packed without subsequent stabilization other than closing off the opening of the balloon. In these embodiments, the beads are preferably polyarylether ketone (PAEK), more preferably polyetherether ketone (PEEK) with chopped carbon fiber.

In some embodiments, a bonding material may be subsequently flowed into the interstitial porosity to further stabilize the packed beads. Preferably, this bonding material comprises an aliphatic polyester such as polycaprolactone (PCL). The bonding material may be resorbable and may include osteogenic additives such as growth factors and stem cells.

In some bead embodiments of the device, the beads of the load-bearing material are made of a heat-bondable material, such as polycaprolactone. When the beads are so constituted, heat may be delivered into the packing and soften the contacting surfaces of the beads. Upon subsequent cool down to body temperature, the contacting surfaces solidify to further stabilize the packed structure. In some embodiments, the heat is provided exogenously. In other embodiments, the heat is provided by the patient's body heat (~37° C.).

Now referring to FIGS. 14 (a)-(d), another embodiment of the device of the present invention 300 comprises at least two bondable components 310 and 320, that are delivered into the disc space in unassembled form, placed closely adjacent one another, and then bonded together, preferably by heat bonding.

Referring to FIG. 14 (b), representing a lateral view of the device of FIG. 14 (a) as seen in the direction of arrow A, and to FIG. 14 (d), representing a perspective view of device 300, in one embodiment, device 300 comprises first and second portions 310 and 320. First portion 310 has a lower bearing wall 312, upper angled wall 314, and a leading wall 316 and a trailing wall 318. Second portion 320 has an upper bearing wall 322, lower angled wall 324 and a leading wall 326 and a trailing wall 328. The combined height of the assembled portion H exceeds that of the disc space. The angled walls form the same angle so that the leading edge of the second portion can be ramped up the angled wall of the first portion.

In use, the first portion 310 is placed in the disc space. Because the height of the first portion is less than the disc space, the first portion 310 is easily positionable anywhere within the disc space. Next, the second portion 320 is introduced into the disc space and ramped up the angled wall of the first portion. Corresponding rails and groove are provided on the angled walls of the first and second portion so as to guide the second portion along the anlong wall of the first portion (see below). Because the second portion only contacts the lower portions of the first portion, the upper wall 322 of the second portion 320 does not touch the adjacent endplate during ramping and so the ramping is easy. Only when the ramping is essentially complete does the upper wall of the second portion contact the adjacent upper endplate. Preferably, the overall height of the ramp H is slightly greater than that of the disc space, so that distraction is achieved when the leading edge of the second portion reaches the leading edge of the first portion.

Referring to FIG. 14 (c), in one embodiment, a cross-section of the device of FIG. 14 (a) is shown, taken along arrows B. As shown in FIG. 14 (c), angled wall 314 of first portion 310 includes a grove 330, while angled wall 324 of second portion 320 includes a ridge 332, designed to fit into a slide against grove 330. In some embodiments, ridge 332 further includes a metal filament 334.

It is understood that the locations of grove 330 and ridge 332 can be interchanged to between angled walls 314 and 324 of upper and lower portions 310 and 320.

Preferably, the rail and groove feature of the ramps has a Morse taper so as to lock the ramp in its assembled form when the leading edge of the second portion reaches the leading edge of the first portion.

Once the two ramp portions are in place, an electric current or heat is passed through wire that passes through the length of the rail of the first portion. The resulting localized heating of the contacting areas softens this region without changing the dimensions of the ramp. Upon cooling, a highly stable, heat bonded ramp results.

Because the ramp of this embodiment is not flowed into the disc space, and the heating is very localized, extremely strong, high temperature materials such as PEEK may be used as the material of construction. In some embodiments, the ramp is made of a high temperature resorbable material. In some embodiments, the high temperature absorbable material is amorphous and has a glass transition temperature of above 100° C. Preferably, the amorphous absorbable is PLA. In some embodiments, the high temperature absorbable material is crystalline and has a melting point of above 100° C. Preferably, the crystalline absorbable is p-dioxanone.

In some ramp embodiments, a guidewire is guided through the center of the ramp guide. The guidewire would allow the ramps to be inserted over the guidewire. The guidewire could be remotely steered into place via IGS or equivalent, and then the ramps could be passed over the guidewire into place. The ramps could be semi-rigid which would allow them to follow the guidewire through the soft tissue, over the wire.

In other ramp embodiments, an "I"-Beam ramp cage is provided. The ramp cage discussed above could incorporate or mate with modular tops and bottoms. These tops and bottoms would have tracks, which would locate on guides fixed to the ramps (or the guides could be on the modular top, and tracks on the ramps) which would aid insertion and ensure the ramps were connected to these modular tops and bottoms. The surfaces of the modular tops and bottoms would go between the ramps and the vertebral bodies such that when assembled, a cross-section of the ramp/top/bottom assembly would resemble an "I"-Beam. This would allow for thinner ramps to ease insertion via an MIS technique or equivalent, and the modular tops and bottoms would provide sufficient surface area to prevent subsidence of the implant into the vertebral bodies. The ramps and modular tops could be shaped in several configurations, inserted assembled, or assembled within the disk space.

In other embodiments, there is provided a ribbon-shaped ramp having a longitudinal through-hole. A threaded rod is inserted through the middle of the ribbon so that, as the threaded rod is turned, the ribbon would "accordion" itself, increasing its height within the disk space. This "accordion"-ing could be achieved by other methods, such as a spring, a cable, etc.

Figure 15:
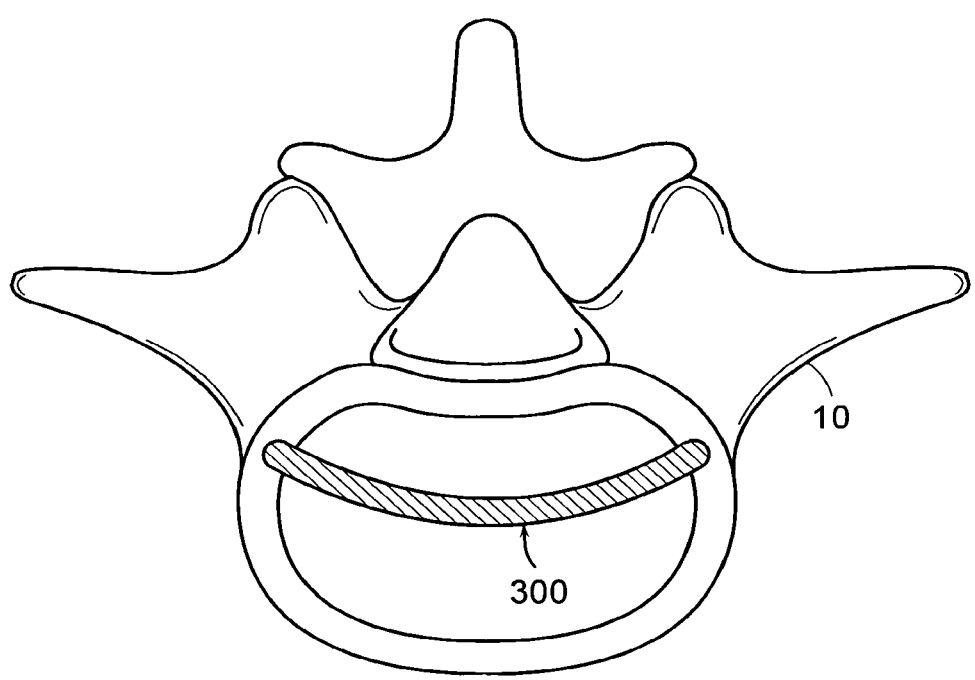
FIG. 15 shows one embodiment of a method of deployment of the device of FIGS. 14 (a)-(d).

Now referring to FIG. 15, one embodiment of a method of use of device 300 shown in FIGS. 14 (a)-(d) is depicted. In this embodiment, the first and second ramp portions 310 and 320 are introduced translaterally so as to form a single ramp stretching essentially transversely across the disc space. This design in advantageous when used in a posterolateral approach, as this approach takes advantage of the fact that the muscle planes in the vicinity of the approach allow the implant to be delivered in a less invasive manner.

embodiments, the sidewalls of the strut also have such openings. In some embodiments, the openings have a diameter of at least 2 mm. In other embodiments, the openings are in the range of from 50-500 um, more preferably between 100 and 300 urn, preferably between 100 and 250 um. These preferred opening sizes are believed to be more conductive to bone growth.

Materials and Compositions Suitable for Use in the Invention

Provided below is a listing of various attributes of the load bearing composition and osteobiologic component of the present invention:

| Feature | Load Bearing Application | Typical Load Bearing Application | Osteobiologic Application | Typical Osteobiologic Application |
| --- | --- | --- | --- | --- |
| Resorption of Matrix | >12 months, preferably beginning >12 months | 12-24 months | 1-3 months | 2 months |
| Overall Strength | High | >50 MPa | Moderate | 1-5 MPa |
| Overall Compression Modulus | Cortico-cancellous Bone | 0.1-2 GPa | Cancellous Bone | 0.1-0.5 GPa |
| Second Phase | Reinforcement | fibers | Osteoconductive | Nano HA particles |
| Aqueous phase | No | no | Yes | Alginate |
| Osteogenic component | No | no | Yes | MSCs |
| Growth factors | Yes | BMP | Yes | BMP |
| Footprint | Support of disc space | 5-40 areal % | Bony fusion volume | 60-95 areal % |

Figure 16:
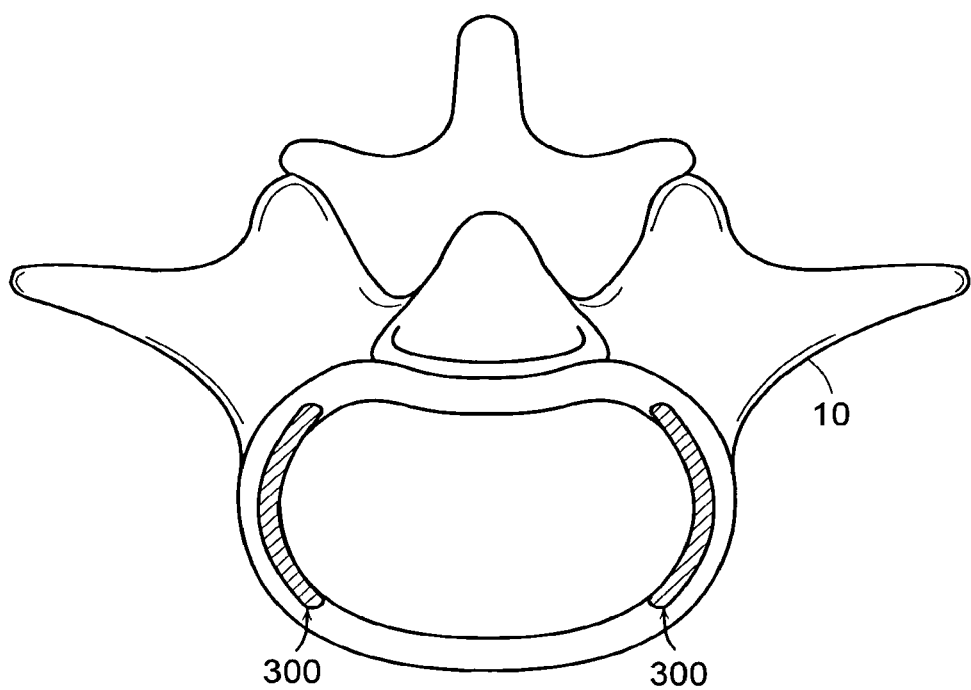
FIG. 16 shows another embodiment of a method of deployment of the device of FIGS. 14 (a)-(d).

In some embodiments thereof, the medial portion of the ramp has a height that is higher than the lateral portions. This feature provides the doming that is advantageous in interbody fusions Now referring to FIG. 16, another embodiment of a method of use of device 300, shown in FIGS. 14 (a)-(c) is depicted. In this embodiment, the ramp of the present invention may be advantageously used in a PLIF procedure. In particular, two ramps may be constructed in-situ so as to form bilateral struts similar to the Steffee struts.

Therefore, in accordance with the present invention, there is provided an intervertebral fusion device comprising a strut comprising:
 a) a first component comprising:
  i) a lower bearing surface adapted for bearing against a lower vertebral endplate, and,
  ii) an upper surface comprising a leading end, an angled middle portion and a trailing end; and
 b) a second component comprising:
  i) an upper bearing surface adapted for bearing against an upper vertebral endplate, and,
  ii) an upper surface comprising a leading end, an angled middle portion and a trailing end,
  wherein the angled portion of the first component mates with the angled portion of the second component.

In some embodiments of the present invention, the struts are completely dense. This feature maximizes the strength of the strut, and so is desirable for the load bearing. In other embodiments, the strut has openings sized to permit bony fusion therethrough. In some embodiments, the upper and lower walls have openings designed to promote bony fusion from the upper endplate to the lower endplate. In other As used herein, the term "second phase" refers to an additive that enhances the performance of the material, for example carbon fibers enhance the strength of the material and calcium phosphate particulates enhance the osteoconductivity of the material. As used herein, the term "aqueous phase" refers to a component of the material capable of maintaining cell viability, e.g. an alginate hydrogel.

Examples of load-bearing components that satisfy the above Table include at least one compound selected from the group consisting of poly(lactic acid), poly(glycolic acid), p-dioxanone fibers, polyarylethyl, polymethylmethacrylate, polyurethane, amino-acid-derived polycarbonate, polycaprolactone, aliphatic polyesters, calcium phosphate, unsaturated linear polyesters, vinyl pyrrolidone and polypropylene fumarate diacrylate or mixtures thereof.

Examples of osteobiologic components that satisfy the above Table include at least one member selected from the group consisting of mesenchymal stem cells, a growth factor, cancellous bone chips, hydroxyapatite, tri-calcium phosphate, polylactic acid, polyglycolic acid, polygalactic acid, polycaprolactone, polyethylene oxide, polypropylene oxide, polysulfone, polyethylene, polypropylene, hyaluronic acid, bioglass, gelatin, collagen and a polymeric fiber.

Because the overall mechanical properties of the load bearing and osteobiologic components can be significantly varied by the inclusion or exclusion of additives such as fibers, particles, cross-linking agents and aqueous phases, some matrix components may be used in some instances as the matrix for the load bearing component and in other instances as the matrix for the osteobiologic component. For example, polycaprolactone may be used in conjunction with p-dioxanone reinforcing fibers as a matrix for a load bearing component, and may also be used in conjunction with polylactic acid and hydroxyapatite as a matrix for an osteobiologic component.

For the purposes of the present invention, the term "hardenable" refers to a material that can be delivered through a cannula into the disc space in a viscous form. In one embodiment, material that can be delivered through a cannula, having at least about 6 mm internal diameter. In another embodiment, a cannula has a diameter of no more than about 6 mm.

Generally, the flowable load-bearing composition and osteobiologic component of the present invention are flowable, meaning they are of sufficient viscosity to allow their delivery through a cannula of on the order of about 2 mm to about 6 mm inner diameter, and preferably of about 3 mm to about 5 mm inner diameter. Such biomaterials are also hardenable, meaning that they can solidify, in situ, at the tissue site, in order to retain a desired position and configuration.

In some instances, the hardenable material is simply a material (such as a low temperature polymer) having a melting point (for crystalline materials) or a glass transition temperature (for amorphous materials) less than 100° C., and is solid a body temperature (37° C.). In some embodiments, these low temperature materials are simply heated to the point where they are viscous and flowable and then injected into the disc space. The subsequent cooling of the viscous material to body temperature then solidifies them. Because these materials do not need to react in-situ, they are desirable for their relative inertness. Accordingly, in some embodiments, they may be freely injected into the disc space without a protective balloon.

In some instances, the hardenable material comprises a cross-linkable component (or "cross-linking agent"). These materials are desirable because cross-linking enhances the strength of the resulting material. Accordingly, in some embodiments, the load-bearing component comprises a cross-linking agent. In such embodiments, it is desirable that the cross-linking agent be delivered into the disc space through a balloon so that the balloon may protect the surrounding tissue from the reactive components during the reaction.

In some embodiments, the load-bearing component comprises a cross-linking agent. In some embodiments, the osteobiologic component comprises a cross-linking agent.

In some embodiments, the hardenable material comprises a polymer and a cross-link agent. In some embodiments, the hardenable material may further comprise a monomer. In some embodiments, the hardenable material may further comprise an initiator. In some embodiments, the hardenable material may further comprise an accelerant.

Preferably, the cross-linking component is made from a two-part composition comprising a monomer and a cross-linking agent.

In some embodiments, the cross-linked composition is flowable at a temperature of between 37° C. and 40° C.

In preferred embodiments, the cross-linkable component is resorbable. For the purposes of the present invention, a resorbable material loses 50% of its initial strength within no more than two years after implantation.

Providing a resorbable cross-linkable component is desirable because it not only provides the high initial strength required for supporting the disc space in an intervertebral fusion application, but also allows for the eventual replacement by bone fusion.

In some preferred embodiments, the resorbable cross-linkable component comprises those cross-linkable components disclosed by Wise in U.S. Pat. No. 6,071,982, the entire teachings of which are incorporated herein by reference.

In preferred embodiments, the cross-linkable component is UV curable. Examples of UV curable cross-linkable components are disclosed in *Biomaterials* (2000), 21:2395-2404 and by Shastri in U.S. Pat. No. 5,837,752, the entire teachings of which are incorporated herein by reference.

In some embodiments, the cross-linkable component is water-curable. In such instances, the resulting body is typically somewhat weak, and so it is preferred that the water-curable cross-linkable compound be used as a matrix for the osteobiologic component.

In some embodiments, the strut is made of a non-resorbable material. Since the non-resorbable material does not degrade over time, the use of the non-resorbable material provides the surgeon with a measure of safety and prevents collapse of the disc space in the event the osetobiologic composition does not produce a fusion.

Preferably, the non-resorbable material is a polymer. The selection of a polymer allows the material to be flowed into place.

In some embodiments, the load bearing polymer is a polyarylethyl ketone (PAEK). More preferably, the PAEK is selected from the group consisting of polyetherether ketone PEEK, polyether ketone ketone PEKK and polyether ketone PEK. In preferred embodiments, the PAEK is polyetherether ketone.

In general, although they possess high strength, PAEK-type polymers have a very high melting point (e.g., 250° C.) and so are not amenable to flow at desirable temperatures. Accordingly, embodiments of the present invention using PAEK as the load bearing composition would typically deliver PAEK in a solid form, such as in bead form or as pre-constructed components, and then assemble and heat bond the components in the disc space under very high temperatures (e.g., 250° C.). These high temperatures would likely require the use of a highly insulated expanded device.

In some embodiments, the strut is a composite comprising fiber, preferably carbon fiber. Composite struts comprising carbon fiber are advantageous in that they typically have a strength and stiffness that is superior to neat polymer materials such as a polyarylethyl ketone PAEK.

In some embodiments, the fiber, preferably carbon fiber, comprises between 1 percent by volume and 60 percent by volume (vol %). More preferably, the fiber comprises between 10 vol % and 50 vol % of the composite. In some embodiments, the polymer and carbon fibers are homogeneously mixed. In others, the composite strut is a laminate. In some embodiments, the carbon fiber is present as chopped state. Preferably, the chopped carbon fibers have a median length of between 1 mm and 12 mm, more preferably between 4.5 mm and 7.5 mm. In some embodiments, the carbon fiber is present as continuous strands.

In especially preferred embodiments, the composite strut comprises:
a) about 40% to about 99% (more preferably, about 60% to about 80 vol %) polyarylethyl ketone PAEK, and
b) about 1% to about 60% (more preferably, about 20 vol % to about 40 vol %) carbon fiber,
wherein the polyarylethyl ketone PAEK is selected from the group consisting of polyetherether ketone PEEK, polyether ketone ketone PEKK and polyether ketone PEK.

In some embodiments, the composite strut consists essentially of PAEK and carbon fiber. More preferably, the composite strut comprises about 60 wt % to about 80 wt % PAEK and about 20 wt % to about 40 wt % carbon fiber. Still more preferably the composite strut comprises about 65 wt % to about 75 wt % PAEK and about 25 wt % to about 35 wt % carbon fiber.

In the context of an arc-shaped inflatable container, for use as a container for the load bearing composition of the present invention, the physical requirements of the flowable load bearing component will depend upon the length and diameter of the arc as well as the physical requirements imposed by the implantation site. For certain embodiments, certain load-bearing compositions may or may not exhibit sufficient physical properties. Physical properties of the load bearing components can also be modified through the addition of any of a variety of reinforcements, such as carbon fibers, Kevlar™ or Titanium Rods, woven or laser etched metallic tubular stents, or other strength enhancers as will be understood in the art.

Certain composite materials, such as carbon fibers embedded in a bonding agent such as a polycaprolactone are believed to be particularly useful in forming the load bearing component of the present invention. For example, graphite (carbon fibers) having a diameter within the range of from about 0.003 to about 0.007 inches is provided in bundles (tows) composed of from about 3,000 to about 12,000 fibers. One typical fiber useful for this purpose is manufactured by Hexcel Carbon Fibers, Salt Lake City, Utah, Part No. HS/CP-5000/IM7-GP 12K. Preferably, the Tow tensile strength is in the range of from about 5,000 to about 7,000 Mpa. Tow tensile modulus is within the range of from about 250 to about 350 Gpa. Within the range of from about 30 to about 60 bundles of the carbon fiber described above is packed in a deflated balloon, optionally along with a Ni—Ti stent having an 8 mm diameter and 8 cm length. Although any of a variety of stents may be utilized, one useful structure is similar to the Smart Stent (Cordis), and it helps keep the structure intact and also adds structural strength to the implanted structure.

In an alternate embodiment, carbon fibers having within the range of from about 15 to about 45 degrees of braids are utilized within the inflatable device to reinforce the load bearing material. The braid may be in the form of a plain weave, and may be obtained, for example, from Composite Structures Technology (Tehachapi, Calif.). A 0.5 inch diameter of 45 degrees braided carbon fiber sleeve is positioned within the center of the balloon. This braided sleeve conforms dimensionally to the inside diameter of the balloon. A 0.3 inch diameter braided carbon sleeve may also be positioned concentrically within the balloon, within the outer braided carbon fiber sleeve. Unidirectional fibers are thereafter introduced inside of the ID of the inner braided carbon sleeve. Unidirectional fibers are also introduced into the annular gap between the two braided sleeves. The volume of the fiber per volume of balloon is generally within the range of from about 40% to about 55%. After placement of the foregoing structure within the portals of the screws, the flowable load bearing material of the present invention having a viscosity within the range of from about 100 cps to about 500 cps is injected under 10 atmospheres pressure into the balloon. The use of braided sleeves will produce higher structural resistance to sheer stress as a result of torsional loads, plus the ability to distribute unidirectional fibers in a homogenous manner within the balloon at all times.

In some embodiments, the polymer comprises polymethylmethacrylate (PMMA). In preferred embodiments, the matrix comprises a radio-opaque agent. A blend of diurethane dimethacrylate (DUDMA) and triethylene glycol dimethacrylate (TEGDMA) that is suitable for the load bearing strut is disclosed in WO 03/005937, the entire teachings of which are incorporated herein by reference.

In some embodiments, the load bearing composition comprises polyurethane. In some embodiments, the polyurethane materials disclosed in U.S. Pat. No. 6,306,177 by Felt (hereinafter "Felt"), the specification of which is incorporated by reference to the extent it is not inconsistent with the remainder of the specification, is selected.

Polyurethanes can be tailored to have optimal stiffness by adjusting the ratio of soft segment to hard segment ratio in the polymer. Furthermore, polyurethanes can be prepared as two-part systems that will cure upon mixing. Preferred polyurethanes, e.g., thermoplastic polyurethanes ("TPU"), are typically prepared using three reactants: an isocyanate, a long-chain macrodiol, and a short-chain diol extender. The isocyanate and long-chain diol form a "soft" segment, while the isocyanate and short-chain diol form a "hard" segment. The hard segments form ordered domains held together by hydrogen bonding. These domains act as cross-links to the linear chains, making the material similar to a cross-linked rubber. It is the interaction of soft and hard segments that determines and provides the polymer with rubber-like properties.

In some embodiments, the strut comprises a photocurable material. In some photocurable embodiments, the material comprises organophosphorous compounds. These compounds are advantageous because the resulting product is calcium phosphate based, and so is both biocompatible and resorbable.

In some embodiments the strut has a resorbable matrix material. A resorbable matrix material is desirable because it is eventually resorbed by the body, and may eventually be replaced by bone.

In some embodiments, the resorbable strut is a high temperature material. For the purposes of the present invention, a high temperature material flows above 100° C. In these cases, the high temperature absorbable material enters the disc space as a plurality of components in a solid form. The components are then contacted in the disc space, and heat is applied to bond the components without deforming the assembled shape.

In some embodiments, the load bearing composition includes a matrix comprising an amino-acid derived polycarbonate.

In some embodiments, the osteobiologic component comprises a matrix comprising a biodegradable polyurethane.

In some embodiments, the osteobiologic component comprises a matrix comprising an amorphous polymer and has a glass transition temperature of below 100° C. Preferably, the amorphous absorbable is D,L-polylactic acid (PLA).

In general, little modification of polylactic acid polymers is possible because there are no other functional groups on the side chain, except the methyl of the lactic acid residue. One possibility to modify the properties of these polymers is to form copolymers with residues having more diverse side chain structures, e.g., lysine.

A poly(lactide-co-lysine) functionalized with peptide containing the arginine-glycine-aspartate (RGD) sequence was prepared by removal of the benzyoxycarbonyl protecting group on the lysyl residue and peptide coupling. The peptide concentration was found to be approximately 3.1 mmol/g, which could be translated into a peptide surface density of 310 fmol/cm$^2$. A surface density of as low as 1 fmol/cm$^2$ of an RGD peptide has been previously determined to promote cell adhesion to an otherwise nonadherent surface (Massia and Hubbell, 1991). Therefore, by carefully processing the copolymer, biodegradable films with cell adhering properties can be prepared from the copolymer of lactide and lysine.

Other strategies have also been employed to widen the properties of polylactides. For example, polylactic acid (PLA) has also been synthesized as an acrylic macromonomer and subsequently copolymerized with polar acrylic monomers (e.g., 2-hydroxyethylmethacrylate) (Barakat et al., 1996). These polymers were studied as amphiphilic graft copolymers for drug delivery purposes. The surface properties of these polymers may be controlled by the ratio of the polylactic acid graft length and copolymer content, and can be potentially used to control the drug release profile and biodistribution. Other examples of this approach include grafting polylactic acid blocks to geraniol and pregnenolone (Kricheldorf and Kreiser-Saunders, 1996).

In some embodiments, the high temperature resorbable material is semi-crystalline and has a melting point of above 100° C. Preferably, the semi-crystalline absorbable is selected from the group consisting of p-dioxanone, L-polylactic acid and poly(glycolic acid) (PGA), and mixtures thereof.

In some embodiments, the strut comprises at last 90 wt % of an aliphatic polyester. Preferably, the aliphatic polyester is polycaprolactone ("PCL").

Polycaprolactone (PCL) is a linear polyester formed through the ring opening of the monomer epsilon-caprolactone. Polycaprolactone is a semi-crystalline thermoplastic resin, which can be readily molded at moderate temperatures to yield tough translucent products. Its crystalline melting point is about 60° C., which represents a theoretical upper temperature limit of use for the present invention. Above its melting point the material is characterized by a high degree of conformability and workability.

Other polymers such as poly(dodecene-1) and transpolyisoprene are also useful in this invention. These polymers are characterized by being crystalline at room temperature, non-crystalline at about 70° C. and having a relatively rapid rate of crystallization when cooled to body temperature. These polymers do not crystallize like simple compounds so that there is a reasonable time lag after the polymer reaches body temperature before crystallization is complete. This permits sufficient time for the flowable composition to be positioned in the disc space while the polymer is still pliable.

In some embodiments, there is provided an absorbable component comprising a polymer formed from aliphatic lactone monomers selected from the group consisting of p-dioxanone, trimethylene carbonate, ε-caprolactone, glycolide, lactide (l, d, dl, meso), delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 1,4-dioxan-2-one, 6,8-dioxabicycloctane-7-one, and combinations thereof.

In one preferred embodiment, the strut comprises a load bearing composition consisting essentially of polycaprolactone. According to Walsh, *Biomaterials* (2001), 22:1205-1212, the compressive strength of essentially solid polycaprolactone is about 15 MPa, and its compressive modulus is about 0.5 GPa.

In general, the higher molecular weight polycaprolactones (PCLs) are preferred, as they tend to have a higher strength and degrade more slowly. Preferably, the molecular weight of the polycaprolactone is at least 30,000 Daltons. More preferably, the molecular weight of the polycaprolactone is at least 40,000 Daltons.

In one preferred embodiment, the strut comprises a load bearing composition of cross-linked polycaprolactone. The cross-linking of the polycaprolactone should enhance its strength. More preferably, the load bearing composition comprises a self-interpenetrating network (S-IPN) comprising a network of host polycaprolactone and cross-linked polycaprolactone. According to Hao, *Biomaterials* (2003), 24:1531-39, the entire teachings of which are incorporated herein by reference, certain mechanical properties of polycaprolactone increased by about 3 fold when it was formed as a S-IPN. When at least 15 wt % HAP was added, the tensile modulus increased to 6 fold over conventional polycaprolactone. If the 3 fold increase in certain mechanical properties reported by Hao would also be realized in compressive strength and compressive modulus, then, the compressive strength of the S-IPN of polycaprolactone may be about 45 MPa, and its compressive modulus may be about 1.5 GPa.

In some embodiments, the polycaprolactone is heat treated to enhance its crystallinity, and thereby even further enhance its resistance to degradation.

In yet a further aspect of the present invention, the above described polymers of the present invention may be liquid or low melting temperature, low molecular weight polymers, with or without photocurable groups. The liquid or low melting polymers are of sufficiently low molecular weight, having an inherent viscosity of about 0.05 to about 0.5 dL/g, to yield materials which can easily flow, with or without heat being applied, through a small diameter delivery device such as a syringe or cannula, with or without mechanical assistance, a caulking gun, a soft-sided tube, and the like.

The aliphatic polyesters useful in the practice of the present invention will typically be synthesized by conventional techniques using conventional processes. For example, in a ring opening polymerization, the lactone monomers are polymerized in the presence of an organometallic catalyst and an initiator at elevated temperatures. The organometallic catalyst is preferably tin based, e.g., stannous octoate, and is present in the monomer mixture at a molar ratio of monomer to catalyst ranging from about 10,000/1 to about 100,000/1. The initiator is typically an alkanol, a glycol, a hydroxyacid, or an amine, and is present in the monomer mixture at a molar ratio of monomer to initiator ranging from about 100/1 to about 5000/1. The polymerization is typically carried out at a temperature range from about 80° C. to about 220° C., preferably from about 160° C. to about 200° C., until the desired molecular weight and viscosity are achieved.

Under the above described conditions, the homopolymers and copolymers of aliphatic polyesters, will typically have a weight average molecular weight of about 5,000 grams per mole to about 200,000 grams per mole, and more preferably about 10,000 grams per mole to about 100,000 grams per mole. Polymers of these molecular weights exhibit inherent viscosities between about 0.05 to about 3.0 deciliters per gram (dL/g), and more preferably about 0.1 to about 2.5 dL/g as measured in a 0.1 g/dL solution of hexafluoroisopropanol (HFIP) or chloroform at 25° C.

Suitable lactone monomers used in the matrices of the present invention may be selected from the group consisting of glycolide, lactide (l, d, dl, meso), p-dioxanone, trimethylene carbonate, ε-caprolactone, delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 1,4-dioxan-2-one, 6,8-dioxabicycloctane-7-one and combinations of two or more thereof. Preferred lactone monomers are selected from the group consisting of glycolide, lactide, p-dioxanone, trimethylene carbonate and ε-caprolactone.

Most preferably, the aliphatic polyesters used in the matrices of the present invention consist of homopolymers of poly(ε-caprolactone), poly(p-dioxanone), or poly(trimethylene carbonate) or copolymers or mixtures thereof, or copolyesters of p-dioxanone or trimethylene carbonate and glycolide or lactide or mixtures thereof, and in particular, copolymers of p-dioxanone/glycolide, p-dioxanone/lactide, trimethylene carbonate/glycolide and trimethylene carbonate/lactide, or copolyesters of .epsilon.-caprolactone and glycolide or mixtures thereof, or mixtures of homopolymers of ε-caprolactone and lactide.

In a specific embodiment of the present invention, a biocompatible, non-absorbable, flowable polymer whose melting point is from about 45° C. to about 75° C. and which is a rigid solid at body temperatures below about 42° C. is placed in a standard Toomeytype disposable syringe with a 35 mm diameter and appropriate capacity of about 50-100 milliliters. The filled syringe is placed in a peel-apart package for sterile delivery and sterilized with cobalt radiation or heat, the former being preferred. Alternatively, the polymer can be placed in a squeeze bottle of suitable capacity and having a slit orifice.

In some embodiments, the strut comprises at least 90 wt % calcium phosphate. According to Hitchon et al. *J. Neurosurg.* (Spine 2) (2001), 95:215-220, the entire teachings of which are incorporated herein by reference, the compressive strength of hydroxyapatite is about 65 MPa and the tensile strength of hydroxyapatite is about 10.6 MPa. The present inventors believe that these values should satisfy typical strut load requirements.

In some embodiments, the matrix is made of a cross-linkable compound. In general, cross-linkable compounds cross-link in-situ and provide higher compressive strengths (typically on the order of 20-120 MPa) than heat-flowable polymers (typically on the order of 1-20 MPa.

In some embodiments, the cross-linkable compound comprises an unsaturated linear polyester.

In some embodiments, the unsaturated linear polyester comprises a fumarate double bond, and more preferably comprises polypropylene fumarate.

In some embodiments, the cross-linkable compound is cross-linked by a monomer, preferably a vinyl monomer, more preferably vinyl pyrrolidone.

In some embodiments, the links produced by the cross-linking agent are biodegradable. Preferred embodiments thereof include polypropylene fumarat-diacrylate.

In some embodiments, the cross-linking reaction is aided by an initiator. In preferred embodiments, the initiator is benzoyl peroxide. In other, light is used as the photoinitiator.

In some embodiments, the cross-linking reaction is aided by an accelerant. In preferred embodiments, the accelerant is N,N-Dimethyl-p-toluidine.

It is believed that the terminal functional groups affect the strength and degradation resistance of the cross-linked matrix. In some embodiments, the cross-linked compound is terminated by a terminal group selected from the group consisting of diepoxide, or diacryal functional groups. In preferred embodiments, the terminal groups are diepoxide functional groups. These terminal functional groups were shown to be more resistant to degradation than divinyl terminated polypropylene fumarat (Domb 1996).

In some embodiments, a porogen such as NaCl or a foaming agent is added to the cross-linkable composition. Preferably, the porogen is water soluble, more preferably it is a water soluble salt or sucrose.

In some embodiments, a calcium phosphate based compound, such as hydroxyapatite or tricalcium phosphate, is added to the cross-linkable composition. These compounds are desirable because they can provide an osteoconductive pathway for bone growth, they can neutralize any acid produced from hydrolysis of the polymer matrix, and provide reinforcement. Preferably, the calcium phosphate is nano high aspect hydroxyapatite.

In some embodiments, the strut of the present invention comprises a load bearing composition comprising a fumarate-based polymer (such as polypropylene fumarate) cross-linked with a cross-linking agent containing a polypropylene fumarate-unit, such as polypropylene fumarate-diacrylate. Exemplary compositions are disclosed in Timmer, *Biomaterials* (2003) 24:571-577, the entire teachings of which are incorporated herein by reference. These compositions are characterized by a high initial compressive strength (about 10-30 MPa) that typically increases over the first 12 weeks, high resistance to hydrolytic degradation (about 20-50 at 52 weeks), and an acceptable modulus for use as a strut (0.5-1.2 GPa).

In preferred embodiments, the polypropylene fumarate: polypropylene fumarate-diacrylate double bond ratio is between about 0.1 and about 3. In more preferred embodiments, the polypropylene fumarate-diacrylate double bond ratio is between about 0.25 and about 1.5.

In more preferred embodiments, the load bearing composition comprising polypropylene fumarate cross-linked by polypropylene fumarate-diacrylate further comprises tricalcium phosphate (TCP), preferably in an amount of between about 0.1 wt % and about 1 wt %. This composition is characterized by a high initial compressive strength (about 30 MPa) that typically increases over the first 12 weeks (to about 45 MPa), a high resistance to hydrolytic degradation (about 45 MPa at 52 weeks), and an acceptable modulus for use as a strut (1.2 GPa at 52 weeks).

In some embodiments, the strut or load bearing composition comprises two cross-linkable polymer compositions. Upon exposure to appropriate cross-linking agents, each of the cross-linkable compositions cross-links with itself, but not with the other cross-linked polymer. The result thereof is a matrix comprising two cross-linked polymers. These are called "interpenetrating networks" ("IPN").

In other embodiments, the strut or load bearing composition comprises a first cross-linkable polymer composition and a second non-cross linkable polymer composition. Upon exposure to an appropriate cross-linking agent, the first cross-linkable compound cross-links with itself, while the second polymer remains unaffected. The result thereof is a matrix comprising a first cross linked polymer and a second non-cross linked polymers. These are called "semi-interpenetrating networks" ("S-IPN")

In some embodiments, the S-IPNs comprise a first biodegradable polymer capable of producing acidic products upon hydrolytic degradation; a second biodegradable polymer, which, preferably via crosslinking, provides a biopolymer scaffolding or internal reinforcement; and optionally a buffering compound that buffers the acidic products within a desired pH range. In a preferred embodiment, the second biodegradable polymer comprises polypropylene fumarate (PPF) which is cross-linked, desirably by a vinyl monomer such as vinyl pyrrolidone (VP) to form the biopolymer scaffolding which provides the semi-IPN with the requisite dimensional and geometric stability. A beneficial end use of this material is in the form of internal fixation devices (IFDs) such as bone supports, plates, and pins, and/or bone cements for bone repair which are formed from the semi-IPN alloy disclosed herein.

In some embodiments, the S-IPN comprises a bone cement containing a biodegradable polymeric semi-IPN alloy comprising a first biodegradable polymer (such as PLGA) capable of producing acidic products upon hydrolytic degradation; and a second biodegradable polymer (such as polypropylene fumarate), which provides a biopolymer scaffolding or internal reinforcement, wherein the second biodegradable polymer is polymerized in vivo to provide a hardened, semi-IPN alloy bone cement. Both the bone cement and dimensionally and geometrically stable IFDs of the disclosure of the invention may advantageously also contain other agents such as bone repair proteins (BRPs) and antibiotics, to, e.g., actively promote bone growth and prevent infection while the bone cement or IFD is in place.

In some embodiments, S-IPNs of the present invention include at least two components. The first component is a linear, hydrophobic biodegradable polymer, preferably a homopolymer or copolymer which includes hydroxy acid and/or anhydride linkages or a linear, non-biodegradable hydrophilic polymer, preferably polyethylene oxide or polyethylene glycol. The second component is one or more crosslinkable monomers or macromers. At least one of the monomers or macromers includes a degradable linkage, preferably an anhydride linkage. The linear polymer preferably constituted between 10 and 90% by weight of the composition, more preferably between 30 and 70% of the composition. The crosslinked polymer preferably constitutes between about 30 and 70% by weight of the semi-interpenetrating network composition, more preferably, between 40 and 60 percent of the composition, with the balance being excipients, therapeutic agents, and other components. The compositions form semi-interpenetrating polymer networks when these components are mixed, and the crosslinkable component is crosslinked. Semi-interpenetrating networks are defined as compositions that include two independent components, where one component is a crosslinked polymer and the other component is a non-crosslinked polymer.

These S-IPN compositions can have a viscosity before crosslinking anywhere between a viscous liquid suitable for injection to a moldable, paste-like putty. The viscosity can be adjusted by adding reactive diluents and/or by adding appropriate solvents. When crosslinked, however, the compositions are solid semi-interpenetrating networks, which are capable of supporting, bone growth and repair.

Linear polymers are defined as homopolymers or block copolymers that are not crosslinked. Hydrophobic polymers are well known to those of skill in the art. Biodegradable polymers are those that have a half-life under physiological conditions of between about two hours and one year, preferably less than six months, more preferably, less than three months. Examples of suitable biodegradable polymers include polyanhydrides, polyorthoesters, polyhydroxy acids, polydioxanones, polycarbonates, and polyaminocarbonates. Preferred polymers are polyhydroxy acids and polyanhydrides. Polyanhydrides are the most preferred polymers.

Linear, hydrophilic polymers are well known to those of skill in the art. Non-biodegradable polymers are those that have a half-life longer than approximately one year under physiological conditions. Examples of suitable hydrophilic non-biodegradable polymers include poly(ethylene glycol), poly(ethylene oxide), partially or fully hydrolyzed poly (vinyl alcohol), poly(ethylene oxide)-co-poly(propylene oxide) block copolymers (poloxamers and meroxapols) and poloxamines. Preferred polymers are poly(ethylene glycol), poloxamines, poloxamers and meroxapols. Poly(ethylene glycol) is the most preferred polymer.

The composition includes one or more monomers or macromers. However, at least one of the monomers or macromers includes an anhydride linkage. Other monomers or macromers that can be used include biocompatible monomers and macromers, which include at least one free-radical polymerizable group. For example, polymers including ethylenically unsaturated groups, which can be photochemically crosslinked, may be used, as disclosed in WO 93/17669 by the Board of Regents, University of Texas System, the entire teachings of which are incorporated by reference.

In some embodiments, the cross-linking polymer of the S-IPN comprises a fumarate, preferably polypropylene fumarate.

For the purposes of the present invention, the non-crosslinkable polymer of an S-IPN may also be referred to as a host polymer. In some embodiments, the host polymer for the S-IPN is selected from the group consisting of polylactic acid, polyglycolic acid, and their copolymers.

The present inventors have observed that both Hao and Timmer report significantly greater mechanical properties and resistance to degradation when the host polymer is cross linked by a monomer having the same repeating unit as the host polymer.

In some embodiments, the cross-linkable compound in the S-IPN is cross-linked by N-vinyl pyrrolidone, polyethylene glycol dimethacrylate (PEG-DMA), ethylene dimethacrylate (EDMA), 2-hydroxyethyl methacrylate (HEMA) or methylmethacrylate (MMA).

In some embodiments, a photopolymerized anhydride is used as the matrix material. These materials are characterized as being strong (compressive strength 30-40 MPa), and relatively stiff (tensile modulus of about 600 MPA to about 1400 MPa).

A. K. Burkoth, *Biomaterials* (2000) 21:2395-2404, the entire teaching of which are incorporated herein by reference, discloses a number of photopolymerizable anhydrides as suitable for orthopaedic use. The repeating unit of these anhydrides comprises a pair of diacid molecules linked by anhydride bonds that are susceptible to hydrolysis. Because the diacid molecules are hydrophobic, there is a limited diffusion of water into the polymer, and so the polymer is subject only to surface degradation (not bulk degradation). This is advantageous because the strength of the polymer will essentially correspond to the mass of the polymer.

In some embodiments, the photopolymerized anhydride is selected from the group consisting of polymers of methacrylated sebacic acid (MSA), methacrylated 1,6-bis(p-carboxyphenoxy) hexane (MCPH), 1,3-bis(p-carboxyphenoxy) propane (CPP), methacrylated cholesterol (MC), methacrylated stearic acid (MstA) and blends and copolymers therefrom.

In some embodiments, the photopolymerization is carried out by adapting a light source to the distal end of the delivery cannula that enters the disc space. In other embodiments, a photo-optic cable is used to transmit light energy into the precursor components that have been deposited in the disc space. In other embodiments, light is transmitted through the skin (i.e, transcutaneously) or through the annulus fibrosus. In some embodiments thereof, a photobleaching initiating system is used.

In some embodiments, a linear polyanhydride is first dissolved in a monomer, and then photopolymerized to form a S-IPN of a photopolymerized anhydride. These are particularly desirable where increased resistance to hydroysis is desired. Accordingly, in some embodiments, the load bearing composition of the present invention comprises a S-IPN comprising a photopolymerized anhydride.

In some embodiments, poly(1,6-bis(p-carboxyphenoxy) hexane (PCPH) is used. This polymer has a degradation of about 496 days, and so is desirably used as the load bearing composition in a strut of the present invention.

Polymerization is preferably initiated using photoinitiators. Photoinitiators that generate an active species on exposure to UV light are well known to those of skill in the art. Active species can also be formed in a relatively mild manner from photon absorption of certain dyes and chemical compounds.

These groups can be polymerized using photoinitiators that generate active species upon exposure to UV light, or, preferably, using long-wavelength ultraviolet light (LWUV) or visible light. LWUV and visible light are preferred because they cause less damage to tissue and other biological materials than UV light. Useful photoinitiators are those, which can be used to initiate polymerization of the macromers without cytotoxicity and within a short time frame, minutes at most and most preferably seconds.

Exposure of dyes and co-catalysts such as amines to visible or LWUV light can generate active species. Light absorption by the dye causes the dye to assume a triplet state, and the triplet state subsequently reacts with the amine to form an active species, which initiates polymerization. Polymerization can be initiated by irradiation with light at a wavelength of between about 200-700 nm, most preferably in the long wavelength ultraviolet range or visible range, 320 nm or higher, and most preferably between about 365 and 514 nm.

Numerous dyes can be used for photopolymerization. Suitable dyes are well known to those of skill in the art. Preferred dyes include erythrosin, phloxime, rose bengal, thonine, camphorquinone, ethyl eosin, eosin, methylene blue, riboflavin, 2,2-dimethyl-2-phenylacetophenone, 2-methoxy-2-phenylacetophenone, 2,2-dimethoxy-2-phenyl acetophenone, other acetophenone derivatives, and camphorquinone. Suitable cocatalysts include amines such as N-methyl diethanolamine, N,N-dimethyl benzylamine, triethanol amine, triethylamine, dibenzyl amine, N-benzylethanolamine, N-isopropyl benzylamine. Triethanolamine is a preferred cocatalyst.

Photopolymerization of these polymer solutions is based on the discovery that combinations of polymers and photoinitiators (in a concentration not toxic to the cells, less than 0.1% by weight, more preferably between 0.05 and 0.01% by weight percent initiator) will crosslink upon exposure to light equivalent to between one and three mWatts/cm.sup.2 applied to the skin of nude mice.

In some embodiments, the matrix comprises a co-polymer having shape memory qualities. In preferred embodiments, the shape memory polymer comprises a first crosslinkable monomer and a second monomer having shape memory qualities. Preferably, the linear polyester has a molecular weight of at least 10,000. Preferably, the first monomer is a linear polyester. Preferably, the second shape memory monomer is n-butyl acrylate. Preferably, cross-linking is induced without an initiator.

Preferably, the shape memory polymer comprises between about 70 wt % and about 90 wt % of the first crosslinkable monomer and between 10 and 30 wt % of the a second monomer having shape memory qualities.

Preferably, the shape memory polymer matrix has a compressive strength of at least 15 MPa. This would make it a suitable candidate as a load bearing composition in a strut of the present invention.

Representative shape memory matrices are disclosed in Lendlein, PNAS, 98(3), Jan. 30, 2001, pp. 842-7, the entire teachings of which are incorporated herein by reference, which discloses polycaprolactone as the first linear polyester. In other embodiments, polylactic acid is the first linear polyester. It is believed that polylactic acid would provide a strong, stiffer matrix, more suitable for use as a load bearing composition in the strut of the present invention.

In one embodiment, the S-IPN comprises:
a) a first part comprising a first bioerodible polymer capable of producing acidic products upon hydrolytic degradation, and
b) a second part comprising a second bioerodible scaffolding polymer, which upon crosslinking provides a biopolymeric scaffolding or internal reinforcement for the S-IPN, and a crosslinking agent for the second bioerodible scaffolding polymer.

In more preferred embodiments, the S-IPN comprises:
a) a first part comprising a first bioerodible polymer capable of producing acidic products upon hydrolytic degradation, a crosslinking initiator, and preferably, a therapeutically effective amount of a biologically active or therapeutic agent and a combination of citric acid and sodium bicarbonate; and
b) a second part comprising a second bioerodible scaffolding polymer, which upon crosslinking provides a biopolymeric scaffolding or internal reinforcement for the S-IPN, and a crosslinking agent for said second bioerodible scaffolding polymer.

In general, many of the resorbable materials are believed to have only moderate strength and stiffness. Therefore, it may be desirable to increase the strength and stiffness of the strut's matrix material by adding reinforcements to the matrix. Although the fibers can be made of non-resorbable materials (such as chopped carbon fibers), preferably the reinforcements are made of materials that are also resorbable.

In some embodiments, the fiber comprises carbon fiber. Preferably, carbon fiber comprises between about 1 vol % and about 60 vol % (more preferably, between about 10 vol % and about 50 vol %) of the load bearing composition. In some embodiments, the polymer and carbon fibers are homogeneously mixed. In others, the material is a laminate. In some embodiments, the carbon fiber is present as chopped state. Preferably, the chopped carbon fibers have a median length of between 1 mm and 12 mm, more preferably between about 4.5 mm and about 7.5 mm. In some embodiments, the carbon fiber is present as continuous strands.

Biodegradable polymers are known, commercially available, or can be synthesized into fibers using known and published methods. Examples of polymers useful in the present invention include poly(L-lactic acid), poly(D,L-lactic acid), poly(D L-lactic-co-glycolic acid), poly(glycolic acid), poly(epsilon-caprolactone), polyorthoesters, and polyanhydrides. These polymers may be obtained in or prepared to the molecular weights and molecular weight distribution needed for service as either the matrix polymer or the pore-forming polymer by processes known in the art. Preferred polymers are poly(alpha-hydroxy esters). Suitable solvent systems are known in the art and are published in standard textbooks and publications. See, for example, Lange's Handbook of Chemistry, Thirteenth Edition, John A. Dean, (Ed.), McGraw-Hill Book Co., New York, 1985, the entire teachings of which are incorporated herein by reference. These polymers may be formed into fibers and webs by standard processing techniques including melt extrusion and spin casting, and are commercially available in woven or non-woven form.

In some embodiments, p-dioxanone fibers are used as the reinforcing phase of the strut. These fibers are advantageous because the high melting point of p-dioxanone resists any thermal degradation of the fibers during injection into the disc space.

In some preferred embodiments, the strut compositions comprise aliphatic polyesters reinforced with p-dioxanone fibers. In more preferred embodiments, those compositions disclosed in U.S. Pat. No. 6,147,135 by Yuan (hereinafter "Yuan"), the specification of which is incorporated herein by reference in its entirety, are selected.

In some embodiments, both the osetobiologic composition and the strut are bioresorbable. The selection of a bioresorbable strut is advantageous because it reduces the amount of foreign materials left in the body.

In some embodiments load-bearing component is used alone.

If desired, the strut material can also include bone growth materials, such as growth factors and stem cells that promote bone growth upon eventual resorption of the resorbable strut. However, since the stem cells must typically be housed in an aqueous phase (such as a hydrogel), the inclusion of stem cells likely requires the introduction of a porosity into the strut that may significantly degrade the strength of the strut. Since the primary purpose of the strut is to support the disc space while the osteogeneic composition promotes fusion, adding stem cells to the strut composition may not be fully desirable in all circumstances. Therefore, in preferred embodiments, only growth factors are added to the strut composition.

In one embodiment, the growth factors are first provided in an aqueous solution and particles of the resorbable strut material are added to the solution. The growth factors cling to the outer surface of the particles. Next, the growth factor-laden particles are separated from the growth factor solution. Next, the growth factor-laden particles are added to the viscous resorbable material.

In some embodiments, the device of the present invention has at least one of the following characteristics:

| Specification | Desired Range of Values | Typical Range of Values |
| --- | --- | --- |
| Ultimate Load in Axial Compression | >5 kN | 5-25 kN |
| Stiffness in Axial Compression | >5 kN/mm | 5-25 kN/mm |
| Ultimate Load in Compression Shear | >2 kN | 2-6 kN |
| Stiffness in Compression Shear | >3 kN/mm | 3-9 kN/mm |
| Ultimate Load in Static Torsion | >5 N-m | 5-20 N-m |
| Stiffness in Compression Shear | >>1 kN/mm | 1-4 kN/mm |

In some embodiments, the material comprising the strut of the present invention has at least one of the following intrinsic properties:

| Intrinsic Property | Preferred Value | More Preferred Value |
| --- | --- | --- |
| Compression Strength | >11 MPa | >25 MPa |
| Fracture Strength | >20 MPa | >40 MPa |
| Compression Modulus | 0.1-10 GPa | 0.5-2 GPa |

In some embodiments, the strut device of the present invention has at least one of the following mechanical performance characteristics:

| Mechanical Property | Preferred Value | More Preferred Value |
| --- | --- | --- |
| Static Compressive Load | >2 kN | >4 kN |
| Cyclic Comp. Load ($10^6$ cycles) | >1 kN | >2 kN |

One example of this embodiment is shown in FIGS. 2 (f) and (g). The arcuate shape has a thickness (t) of 3 mm, inner radius ($r_i$) of 22 mm, an outer radius ($r_o$) of 25 mm and an average height if 15 mm. When this device is produced from a photopolymerized polyanhydride with an intrinsic compressive strength of 30 MPa and compressive modulus of 1 GPa, the static compressive load required to fail the device is 6.6 kN and the compressive stiffness is 15 kN/mm.

In some embodiments, the novel struts of the present invention can be used with conventional osteobiologic materials, such as platelet-rich plasma (PRP), allograft particles (such as demineralized bone matrix (DBM) and cancellous chips) and autograft.

In preferred embodiments, the osteobiologic component of the present invention acts in a manner similar to the cancellous core of a vertebral body. Desirable features for the osteobiologic composition of the strut are as follows:

a) strength similar to that of cancellous bone;
b) stiffness similar to that of cancellous bone (or, in relatively large footprint embodiments, cortico-cancellous bone);
c) mild degradation resistance (e.g., degrades in manner that allows bone growth therethrough; and
d) resorbable.

As noted above, in preferred embodiments, the in-situ formed osteobiologic composition comprises:

a) a matrix material (preferably, a polymer flowable at between 40° C. and 80° C.; a linear anhydride, or a fumarate,
b) osteogenic component (preferably, mesenchymal stem cells present in a concentrated amount), and
c) an osteoinductive factors (preferably, a bone morphogenetic protein).

Examples of matrices that could be used in the osteobiologic component include ceramics comprising calcium phosphate such as, for example, hydroxyapatite or tricalcium phosphate, polylactic acid, polyglycolic acid, polygalactic acid, polycaprolactone, polyethylene oxide, polypropylene oxide, polysulfone, polyethylene, and polypropylene, hyaluronic acid, which may be purified with or without crosslinking, bioglass, gelatin and collagen.

Preferably, the matrix is a resorbable composition that resorbs within a 2-4 month time period after in-situ formation and comprises:

a) a polymer phase that flows or softens at a temperature of between 40° C. and 80° C. (more preferably, comprising an aliphatic polyester such as polycaprolactone) and is preferably present in an amount of between 50 vol % and 70 vol % of the osteobiologic composition, and b) an osteoconductive calcium phosphate phase (more preferably hydroxyapatite) preferably present in an amount of between 10 vol % and 30 vol % of the osteobiologic composition.

Optionally, a reinforcing phase (preferably, resorbable polymeric chopped fiber) is also preferably present in an amount of between about 10 vol % and, about 30 vol % of the osteobiologic composition.

Preferably, the osteogenic component comprises an aqueous phase (preferably a hydrogel phase) having viable osteoprogenitor cells (preferably mesenchymal stem cells) present therein in a concentrated amount. Preferably, the aqueous phase is present as an interconnected phase throughout the osetobiologic composition, and is present in an amount of between about 25 vol % and about 35 vol % of the osteobiologic composition and has an average diameter of between 100 and 250 µm.

Preferably, the osteoinductive factor is selected from the group consisting of a bone morphogenetic protein and a transforming growth factor. More preferably, the osteoinductive factor is a bone morphogenetic protein. The bone morphogenetic protein may be present in any phase of the osteobiologic composition. When immediate delivery of the bone morphogenetic protein is desirable, the bone morphogenetic protein is present in the hydrogel phase. When intermediate delivery of the bone morphogenetic protein is desirable, the bone morphogenetic protein is present in the polymer phase. When long term delivery of the bone morphogenetic protein is desirable, the bone morphogenetic protein is present in the ceramic phase. It is preferable to have at least twice the autologous level of bone morphogenetic protein, and more preferably, at least 10 times the autologous level of bone morphogenetic protein.

In one preferred embodiment, the matrix comprises a material having a melting point between about 42° C. and about 95° C., (preferably between about 42° C. and about 90° C.) which allows it to be flowed into the disc space without causing tissue necrosis, and then in-situ solidified to provide the needed structural support. The scaffold material further comprises a porogen that allows it to be made into a porous scaffold by conventional leaching techniques. Lastly, growth factors and osteoprogenitor cells such as mesenchymnal stem cells can be flowed through the open porosity of the scaffold to induce bone growth throughout the scaffold.

In another preferred embodiment, mesenchymnal stem cells are isolated from a bone marrow aspirate taken from the patient and incorporated into bioabsorbable particles capable of maintaining cell viability, such as hydrogels. Preferably the hydrogels will absorb quickly such that the cells will be released to form bone. The particulate are then mixed with a scaffold material in a first liquid form that will solidify upon implantation. Preferably, the scaffold material resorbs slowly such that bone can be formed throughout the porosity before the scaffold degrades away. Preferred scaffold materials are polymers that can be dissolved in a cell-friendly solvent such as dimethyl sulfoxide (DMSO), which will leach out once implanted, causing the polymer to precipitate out of solution and create a solid scaffold. Preferably a growth/nutritive factor cocktail for inducing the osteoprogenitor cells to form bone and continue to support the bone formation process is incorporated into the cell-seeded hydrogel as well as the scaffold material. Following disc space preparation the system is injected to the disc space and no other surgical steps are required.

In some aspects of the present invention, there is provided an in-situ formed (and preferably injectable) intervertebral fusion device comprising:
  a) a porous scaffold having a porosity suitable for new bone formation,
  b) viable osteoprogenitor cells, and
  c) osteoinductive factors required to signal the osteoprogenitor cells to form new bone.

Porous scaffolds that can form upon injection through a minimally invasive surgical procedure can be made of a material selected from the group consisting of crosslinked natural and synthetic polymers, low melting point polymers, polymers dissolved in biocompatible solvents, and setting ceramics. Porous scaffolds suitable for use in the present invention are disclosed in U.S. Pat. Nos. 6,280,474 and 6,264,695 (swellable polymers), U.S. Pat. No. 5,888,220 (polycaprolactone/polyurethane), U.S. Pat. No. 6,224,894 (absorbable polyoxaester hydrogels) and U.S. Pat. No. 6,071,982, the entire teachings of the forgoing U.S. patents are incorporated herein by reference.

In many embodiments, the resorbable polymers, calcium phosphates and reinforcing phases disclosed above in the description of the strut may be used to form the preferred matrix. In general, the matrix is substantially weaker (owing to the presence of either open porosity or an interconnected hydrogel phase) than the strut, and hydrolyzes quicker.

In one aspect of the present invention, the matrix has a first absorbable phase of about 1 weight percent to about 99 weight percent of any of the aliphatic homopolyesters of ε-caprolactone, p-dioxanone, or trimethylene carbonate or copolymers or mixtures thereof, with the remaining resorbable phase comprising a bone osteoconductive or osteoinductive calcium containing, non-fibrous, powdered compound, preferably a calcium phosphate such as hydroxyapatite, tri- or tetra-calcium phosphate, or a bioactive glass, or mixtures thereof.

In a further aspect of the present invention, the matrix has a first absorbable phase of about 1 weight percent to about 99 weight percent of aliphatic copolyesters of p-dioxanone or trimethylene carbonate, and glycolide or lactide or mixtures thereof, and in particular, copolymers of p-dioxanone/glycolide, p-dioxanone/lactide, trimethylene carbonate/glycolide and trimethylene carbonate/lactide, with a remaining resorbable phase comprising a bone osteoconductive or osteoinductive calcium containing, non-fibrous, powdered compound, preferably a calcium phosphate such as hydroxyapatite, tri- or tetra-calcium phosphate, or a bioactive glass, or mixtures thereof.

In a further aspect of the present invention, the matrix has a first absorbable phase of about 1 weight percent to about 99 weight percent of aliphatic copolyesters of ε-caprolactone and glycolide or mixtures thereof, or mixtures of homopolymers of ε-caprolactone and lactide, with a remaining resorbable phase comprising a bone osteoconductive or osteoinductive calcium containing, non-fibrous, powdered compound, preferably a calcium phosphate such as hydroxyapatite, tri- or tetra-calcium phosphate, or a bioactive glass, or mixtures thereof.

The above-noted matrices will contain sufficient amounts of the absorbable polymer phase and sufficient amounts of the resorbable second bone regenerating phase to effectively function as bone cements or bone substitutes. Typically, the composites will contain about 1 to about 99 weight percent of polymer phase, and more preferably about 5 to about 95 weight percent. The composites will typically contain about 1 to about 99 weight percent of the bone regenerating phase, and more preferably about 5 to about 95 weight percent.

It will be appreciated by those skilled in the art that the relative amounts of the first absorbable, polymeric phase to the second resorbable phase in the above-noted matrices will depend upon various parameters including, inter alia, the levels of strength, stiffness, and other physical and thermal properties, absorption and resorption rates, setting and hardening rates, deliverability, etc., which are required. The desired properties of the composites of the present invention and their level of requirement will depend upon the body structure area where the bone cement or substitute is needed. Accordingly, the composites of the present invention will typically contain about 1 weight percent to about 99 weight percent, and more preferably about 5 weight percent to about 95 weight percent of aliphatic polyester homo- or co-polymers, or blends thereof.

A further aspect of the present invention is a process by which the matrix component of the osteobiologic composition is prepared. The matrix can be prepared by a one-step or a two-step process in which a bone regenerating material is mixed in the reaction vessel with a just-formed polymer (one-step process), or mixed with a preformed polymer in a separate vessel (two-step process).

The composites of the present invention can be manufactured in the following two-step process. The preformed polymers and bone regenerating materials are individually charged into a conventional mixing vessel having a conventional mixing device mounted therein such as an impeller. Then, the polymers and bone substitutes are mixed at a temperature of about 150° C. to about 220° C., more preferably about 160° C. to about 200° C., for about 5 to about 90 minutes, more preferably for about 10 to about 45 minutes, until a uniformly dispersed composite is obtained. Then, the composite is further processed by removing it from the mixing device, cooling to room temperature, grinding, and drying under pressures below atmospheric at elevated temperatures for a period of time.

In addition to the above manufacturing method, the composites can be prepared by a one-step process by charging the bone regenerating material to a reaction vessel which contains the just-formed polymers. Then, the polymers and bone substitutes are mixed at a temperature of about 150° C. to about 220° C., more preferably about 160° C. to about 200° C., for about 5 to about 90 minutes, more preferably for about 10 to about 45 minutes, until a uniformly dispersed composite is obtained. Then, the composite is further processed by removing it from the mixing vessel, cooling to room temperature, grinding, and drying under pressures below atmospheric at elevated temperatures for a period of time.

In other embodiments, the matrix of the present invention includes a bone implant material, which can be readily molded at a selected temperature at or below about 60° C. The material is formed as a cohesive mixture of hard filler particles and a binder composed of a biocompatible, biodegradable thermoplastic polymer having fluid-flow properties at the selected temperature at or below about 60° C.

Any hard biocompatible filler particles, including autogenous bone chips, can be used in this invention. However hydroxyapatite is a preferred filler for its performance and biological profile. Tricalcium phosphate and glass granules may also be used alone or in combination with hydroxyapatite, particularly if some degree of resorption is desired in the filler.

The binder preferably ranges in fluid-flow properties (flowability) between a highly viscous fluid and a putty-like semi-solid, at the selected temperature. With too low a binder viscosity, the implant material suffers the same problems seen in loose-particle implants: poor shape retention, once molded, and poor cohesiveness, leading to exfoliation of particles before or during the tissue ingrowth period. In a preferred embodiment, the polymer includes polylactic acid having a molecular weight between about 400 and about 5,000 daltons.

The binder preferably constitutes no more than about one-third of the total solid volume of the material, leaving void space in the material, which can accommodate tissue ingrowth. The minimum amount of binder is that necessary to give easy formability and provide sufficient particle cohesion and shape retention during the period of tissue ingrowth.

By similar methods, polylactic acid having progressively greater molecular weights between about 2,000 and about 5,000 daltons were prepared and tested for binder characteristics when formulated with hydroxyapatite particles. Above about 2,000 daltons, the implant material was quite hard and difficult to mold by hand at 40° C., and at 5,000 daltons, temperatures up to about 60° C. were required to achieve moldability.

To form the implant material of the invention, the binder from above is mixed with hydroxyapatite particles, and the components are thoroughly blended. Preferably the material contains some void space, to allow tissue ingrowth independent of polymer breakdown. Since the void space of a mass of spherical particles is about one-third that of the particle mass, the implant material preferably contains less than about one-third by volume of binder. To optimize the void space, the minimum amount of binder needed to produce good particle cohesiveness, typically between about 5% and 20% of the total solid volume of the material, is added. In one embodiment, implant material containing 80% hydroxyapatite particles (average particle size of about 650 microns), and 20% of polylactic acid polymer having average polymer molecular weights of about 1,100 daltons was prepared. The material was easily moldable by hand at 50° C., and showed good cohesiveness and shape retention at 37° C.

In practicing the invention, there is provided a moldable hydroxyapatite bone-implant material. As described above, implant material having a range of molding temperatures and biodegradability can be provided, by adjusting the composition and amount of binder in the material. Material having a relatively high molding temperature, e.g., between about 40° C. to about 60° C., is generally preferred where the implant needs to be in a relatively rigid condition during the process of tissue ingrowth, for example, to prevent significant shape deformation. Here the material is applied and shaped to the bone site in a heated state; after cooling, it assumes the desired rigid condition.

The material can be formulated with thermoplastic polymer binders of various composition and molecular weights, to achieve a selected molding temperature, rigidity in the bone site, and rate of binder breakdown. By varying the relative proportions of binder and particles, selected changes in the void space and cohesiveness of the material are possible.

Matrix scaffold polymers can also be produced by first dissolving the polymer in a biocompatible, water-soluble solvent, injecting the material into the disc space, and then allowing the solvent to leach out of the polymer into the body, thereby causing the polymer to solidify in vivo. Suitable polymers compatible with such solvents include, but are not limited to, poly(lactic acid), poly(glycolic acid) and copolymers therefrom. Suitable biocompatible, water-soluble solvents include dimethylsulfoxide (DMSO). Preferably, the volume ratio of polymer to solvent is at least 1:5, more preferably at least 1:2. By maximizing the amount of polymer in the polymer/solvent injection, the amount of structural material solidified in the body is maximized while minimizing the amount of solvent to be excreted by the body.

Injectable ceramics can also serve as components in the matrix of the osteobiologic component. Preferred injectable, resorbable ceramics are amorphous calcium phosphates or hydroxyapatites. (See U.S. Pat. Nos. 6,214,368 and 6,331,312, the entire teachings of which are incorporated herein by reference.)

In some embodiments of the present invention, porosity is produced in the matrix to produce a porous scaffold material. Once in-situ porosity is produced in the osetobiologic composition, the surgeon can then inject an osteogenic component (such as mesenchymnal stem cells) or an osteoinductive component (such as bone morphogenetic protein) into the porosity, thereby enhancing the ostobiologic nature of the composition.

Providing porosity in-situ allows the matrix of the osteobiologic composition to comprise materials such as polymers that flow at temperatures only well above body temperature. For example, many polymers such as polycaprolactone flow at about 60° C., a temperature that may well destroy the viability of mesenchymnal stem cells contained within the flowable polymer.

Therefore, in some embodiments of the present invention, polymeric materials that become flowable above 45° C. are first made flowable by raising their temperature to at least 45° C., the flowable polymer is then injected into the disc space, the in-situ formed material is then made porous, and porous material is then injected with mesenchymnal stem cells.

In some embodiments of the present invention, in-situ porosity is accomplished by first delivering the matrix material into the disc space as beads, then tightly packing the beads within the disc space, and then bonding the beads, preferably by heat bonding, into a stable structure.

In some embodiments of the present invention, porosity is produced in the matrix to including a foaming agent in the matrix material.

According to another embodiment, porous injectable graft materials are optionally made by adding a degradable gas-producing compound. As gas bubbles are produced from the gas-producing compound, pores are formed in the bone-like materials. The size of the pores are preferably controlled by adjusting the amount of gas-producing compound and the viscosity of the mineral matrix in the fluid used to mix the materials. In a specific embodiment, sodium bicarbonate and/or calcium bicarbonate is added to the flowable matrix material and a precise amount of acid (e.g. citric acid, formic, acetic, phosphoric acids, hydrochloric acid) is added to the mixing fluid. The acidity of the mixing fluid causes carbon dioxide to be released from the sodium bicarbonate, wherein the carbon dioxide ultimately forms pores in the matrix material. In an alternative embodiment, hydrogen peroxide is combined with peroxidase in the graft material. The peroxidase releases oxygen from the hydrogen peroxide, which has the added advantage of sterilizing the wound site.

In some embodiments of the present invention, in-situ porosity can be produced in the matrix material including a porogen with the matrix material, and then in-situ leaching out of the porogen. Preferably, a porogen is a water-soluble materials. Biodegradable materials can be fabricated into three dimensional anatomical shapes having load bearing properties similar to or exceeding that of natural bone. A matrix component of the osteobiologic component has the capability of being rendered porous and can serve to foster bony fusion. In these embodiments, the osteobiologic composition can be implanted without first being rendered to its porous state. Porosity can be achieved after implantation by a faster rate of biodegradation of a pore-forming component of the osteobiologic component relative to a slower rate of degradation of the matrix component of the osteobiologic component. The porous osteobiologic component has sufficient compressive strength and modulus to serve as a bone replacement prosthesis during that period wherein the body regenerates new natural bone within and to the shape of the osteobiologic component. Ultimately, the osteobiologic component is replaced by natural bone as the osteobiologic component biodegrades and by such process is displaced or eliminated from the body by natural processes.

In such embodiments, the osteobiologic composition comprises at least two components, a continuous matrix component and an included pore-forming component. The matrix component comprises a biodegradable material having a rate of degradation, which at least matches the rate at which the body regenerates natural bone tissue. The pore-forming component is a material, which differs from the matrix material such that it may be differentiated from the matrix component and ultimately be removed therefrom by differential dissolution or biodegradation to provide porosity to the prosthetic template either prior to or after implantation.

Unless wholly removed from the matrix polymer of the implant before implantation, the molecular weight, molecular weight distribution and degree of crystallinity of the pore-forming polymer is also of significant concern. Generally, the pore-forming polymer should biodegrade and/or bioresorb at a rate that is at least four times greater than that of the matrix polymer. Further, the pore-forming polymer should have a polydispersity index of at least 3 to provide for a controlled degradation over a period of time that avoids intolerable localized pH concentrations due to its degradation by-products.

The osteobiologic compositions of these embodiments can contain a relatively high ultimate porosity capacity. That is, the osteobiologic composition is fabricated in a manner, which results in an osteobiologic component capable of being rendered highly porous prior to implantation. For example, the matrix may be formed around included particles or fibers which particles or fibers are subsequently removed from the matrix by solvent dissolution or other methods of degradation, leaving a highly porous matrix scaffold structure. Alternatively, the particles or fibers embedded within the formed matrix may be retained in the osteobiologic composition for dissolution or degradation in situ after implantation. In addition, portions of the pore-creating material may be removed prior to implantation of the osteobiologic composition providing a range of actual to ultimate porosities of the implantable osteobiologic components.

The ultimate porosity capacity may be defined as the percent porosity of the matrix after at least 90% of the pore forming material has been removed from the template, either in vitro or in vivo. In the present invention, it is preferred that the ultimate porosity capacity of the biodegradable/bioresorbable osteobiologic component be in the range of between about 20% and about 50% volume of the osteobiologic component.

The biodegradable osteobiologic composition of the present invention, which has the porogen features described above, including high mechanical strength necessary for replacement of load bearing bones, high ultimate porosity capacity to permit bony fission therethrough, and a rate of degradation approximately matching the rate of new tissue growth may, for example, be formed by the methods described below. In its simplest embodiment, these osteobiologic compositions of the present invention are formed by distributing within a polymeric matrix a pore-creating substance (or "porogen"). Regardless of the specific methods used to form the osteobiologic composition, the product will include a three-dimensional, anatomically-shaped osteobiologic composition having a high ultimate porosity capacity due to the presence of a pore creating substance dispersed within the matrix.

The pore creating substance may be formed for example of salts, polysaccharides, protein, polymers other than the matrix polymers, or other non-toxic materials such as gelatin which are, for example, soluble in a solvent which does not dissolve the matrix polymer; made fluid at a higher glass transition temperature (Tg) or melting temperature (Tm) than the matrix polymer; or otherwise differentiated from the matrix polymer so as to retain an independent structure from the polymeric matrix. When subsequently removed, the desired pores are formed within the matrix.

The temperature required to fluidize polymers is that which permits non-hindered flow of polymer chains. For amorphous polymers, this "flow temperature" is the glass transition temperature (Tg). However, for semi-crystalline polymers this "flow temperature" is the melting temperature (Tm). As used herein, flow temperature is meant to be that temperature which permits non-hindered flow of polymer chains and includes, as appropriate, Tg for amorphous polymers and Tm for at least semi-crystalline polymers.

The pore creating substance may be in the form of particles such as salt, which after forming a matrix in which the particles have been included, the particles are leached out or otherwise removed from the matrix leaving a polymeric matrix with high porosity. The pore creating substance may be in the form of fibers such as polymeric fibers or webs dispersed within a formed polymeric matrix. The dispersed fibers and the surrounding matrix possess differential rates of degradation, with the fibers being degraded at a faster rate than the matrix, thereby being removed from the osteobiologic composition and creating a highly porous polymeric, osteobiologic composition.

The porogen-containing osteobiologic composition may be formed by dispersing the pore-creating substance in a body of powdered polymer. Preferably, the pore-creating substance is a first polymer in fiber or web form dispersed in a body of powdered second polymer. The second polymer has a lower flow temperature (Tf) such that when the dispersion is heated above the flow temperature of the powder, the powder is fluid, but the dispersed fibers are not. The fluid polymer is next solidified, e.g., by permitting the dispersion to return to ambient temperature, resulting in a polymeric matrix having entrapped therein the pore-forming substance.

In a preferred embodiment, a first polymer is used to form the matrix and a second polymer is used to form the pore-creating substance dispersed within the first polymer. Both first and second polymers are biodegradable but the second degrades at a faster rate than the first polymer, e.g., approximately two to eight times faster, and preferably about four times faster creating the desired porous body for ingrowth and proliferation of cells. For example, poly(glycolic acid) (PGA) fiber meshes may be dispersed within poly(L-lactic acid) (PLLA). Upon curing of the PLLA matrix, the PGA fiber mesh is embedded within the PLLA matrix. The PGA fibers biodegrade at a more rapid rate than PLLA, thus creating a template having a high ultimate porosity capacity.

The pore creating substance may be formed of a low molecular weight polymer while the matrix is formed of a high molecular weight polymer. Because the low molecular weight polymers degrade at a faster rate than the high molecular weight polymers an implant having a desired rate of degradation of each of the pore creating substance and the matrix can be formed.

In vivo degradation of the pore-creating substance at a faster rate than the template matrix, such as PGA fibers which degrade within months of implantation in a PLLA matrix which may take more than one year to degrade, permits gradual replacement of the pore-creating substance with growing bone cells. The resorbing pore-creating substance is gradually replaced with newly formed bone tissue, maintaining a mechanically strong bone prosthesis. The more slowly degrading polymeric matrix is then resorbed and replaced with bone tissue proliferating from the network of growing tissue already present throughout the prosthetic template.

In some embodiments, the matrix has a sufficient number of pores or passageways so that the total accessible surface area of the substrate is at least five times greater than a solid object having the same external dimensions. Thus, the preferred total surface area can be achieved by using a substrate, which comprises a mass of powder, a mass of granules, a mass of fibers, or a highly porous block of substrate material. Preferably, the average pore size in the matrix is greater that 20 µm, more preferably greater than 50 µm, more preferably greater than 100 µm. In some embodiments, the pore size is between about 100 µm and 250 µm.

The osteobiologic compositions of the present invention have a high ultimate porosity capacity, resulting in a highly porous matrix containing a uniformly distributed and interconnected pore structure. Pore volume of the porous osetobiologic composition is approximately 20% to 90%, and the average pore diameter is approximately 50 to 250 µm. The pore volume and diameter also directly relate to the rate of tissue ingrowth and matrix degradation. The porous matrix of the present invention accommodates large number of cells adhering to the matrix, permits cells to be easily distributed throughout the template, and allows an organized network of tissue constituents to be formed. The matrix preferably promotes cell adhesion and permits the attached cells to retain differentiated cell function. In some embodiments, the leachate produces an open porosity having an average pore size of between 20 µm and 500 µm, preferably 50-250 µm. This range is preferred for bone growth.

In some embodiments, the matrices of the osteobiologic component are fabricated of polymers and by methods which result in implants which are capable of being rendered porous for tissue ingrowth while retaining sufficient mechanical strength to be suitable for supporting a disc space. For example, in their preporous state the osteobiologic compositions of the present invention possess a compressive strength of approximately 5 MPa to 50 MPa and a compressive modulus of approximately 50 MPa to 500 MPa as tested by an Instron Materials Testing Machine according to American Society for Testing and Materials (ASTM) Standard F451-86. The values of 5 MPa compressive strength and 50 MPa compressive modulus correspond to the mid-range values for human trabecular bone.

The biodegradable, bioresorbable matrices of the present invention preferably are formed of polymeric materials, the matrix polymer having a rate of degradation which is matched to the rate of tissue in-growth. The matrix polymeric substance preferably ranges in weight average molecular weight from approximately 50,000 to 200,000. Crystallinity of the matrix polymer of implant is approximately 0 to 25%. The molecular weight and molecular weight distribution of the matrix polymer is related to the rate at which the matrix biodegrades. In a matrix of broad molecular weight distribution, e.g., having a polydispersity index (Mw/Mn) greater than 2 fractions of the material exist in short to long polymeric chains. This diversity allows a continuation of degradation over time without sharp changes, e.g., in pH due to degradation products, as may occur with a material having a narrow molecular weight distribution. In the present invention, the polydispersity index of the matrix is preferably in the range of 3-6.

In some embodiments possessing in-situ created porosity, mesenchymnal stem cells ("MSCs") are then delivered into the porous matrix.

In some embodiments, the mesenchymnal stem cells are delivered into the porosity of the scaffold by simply directing an aqueous solution containing mesenchymnal stem cells into the scaffold. In some embodiments, an additional cannula can be placed near the porous matrix to serve as an exit cannula for the fluid.

In some embodiments, a hydrophilic matrix material such as polylactic acid may be used. In these instances, it has been found that mesenchymnal stem cells do not tenaciously adhere to the surface of the polylactic acid. Accordingly, in some embodiments, a lining material, such as hydroxyapatite (HA), may be used to line the inner surface of the scaffold with a material to which mesenchymnal stem cells more tenaciously adhere. In some embodiments, the linings disclosed in U.S. Pat. No. 5,133,755 by Brekke, the entire teachings of which are incorporated herein by reference (hereinafter "Brekke"), are selected.

In some embodiments, other cell adhesion molecules may be bound to the inner surface of the matrix in order to enhance the adhesion of the mesenchymnal stem cells to the scaffold. The term "cell adhesion molecules" refers collectively to laminins, fibronectin, vitronectin, vascular cell adhesion molecules (V-CAM), intercellular adhesion molecules (I-CAM), tenascin, thrombospondin, osteonectin, osteopontin, bone sialoprotein, and collagens.

Preferably, the mesenchymnal stem cells are delivered into the in-situ porosity under pressure, such as by injection. In these cases, it is helpful to surround the porous osteobiologic composition with a containing envelope in order to contain the osteogenic component within the in-situ porosity and prevents its leakage outside the osteobiologic composition.

In some embodiments, the envelope is the strut component having a 360 degree span. In other embodiments, the envelope can be an inflatable device component of the osteobiologic composition.

Although it may be useful to create in-situ porosity, it may sometimes be problematic to evenly distribute the mesenchymnal stem cells throughout the in-situ created porosity under normal injection pressures. In some embodiments of the present invention, the mesenchymnal stem cells are delivered into the in-situ porosity under a higher pressure that is sufficient to fill 90% of the porosity. Preferably, the pressure is high enough to completely fill the porosity.

Therefore, in accordance with the present invention, there is provided a method delivering an osteogenic component, comprising the steps of:

a) injecting an osteobiologic composition into a disc space,
b) creating in-situ porosity in the osteobiologic component, and
c) delivering an osteogenic component into the in-situ porosity under a pressure of at least sufficient to fill at least 90% of the porosity.

In some embodiments of the present invention, the osteobiologic component of the present invention further comprises a gelled aqueous phase, wherein viable mesenchymnal stem cells are located in the aqueous phase.

Because mesenchymnal stem cells (and many growth factors) are very heat sensitive, it is desirable to deliver mesenchymnal stem cells and growth factors at or near body temperature. However, many of the bioabsorbable polymers are flowable at temperatures well in excess of body temperature. Similarly, many cross-linked polymers experience an exotherm of over 100° C. It is not known whether mesenchymnal stem cells and growth factors could remain viable after prolonged exposure to these temperatures.

Since calcium phosphate can be made flowable at body temperature, it is desirable to select an osteobiologic composition having a matrix comprising calcium phosphate when also choosing to deliver the mesenchymnal stem cells or growth factors to the disc space during the delivery of the matrix component of the osteobiologic composition.

Therefore, in some embodiments there is provided an osteobiologic composition that is flowable at body temperature, the composition comprising a matrix comprising calcium phosphate and an osteogenic component.

Hydrogels are useful in this respect because they can adequately protect bone growth cells contained therein.

A "hydrogel" is a substance formed when an organic polymer (natural or synthetic) is set or solidified to create a three-dimensional open-lattice structure that entraps molecules of water or other solution to form a gel. The solidification can occur, e.g., by aggregation, coagulation, hydrophobic interactions, or cross-linking. The hydrogels employed in this invention rapidly solidify to keep the cells at the application site, thereby eliminating problems of phagocytosis or cellular death and enhancing new cell growth at the application site. The hydrogels are also biocompatible, e.g., not toxic, to cells suspended in the hydrogel.

A "hydrogel-cell composition" is a suspension of a hydrogel containing desired tissue precursor cells. These cells can be isolated directly from a tissue source or can be obtained from a cell culture. A "tissue" is a collection or aggregation of particular cells embedded within its natural matrix, wherein the natural matrix is produced by the particular living cells.

The hydrogel-cell composition forms a uniform distribution of cells with a well-defined and precisely controllable density. Moreover, the hydrogel can support very large densities of cells, e.g., 50 million cells/ml. These factors improve the quality and strength of the new tissue. In addition, the hydrogel allows diffusion of nutrients and waste products to, and away from, the cells, which promotes tissue growth.

Hydrogels suitable for use in the osteobiologic composition of the present invention are water-containing gels, i.e., polymers characterized by hydrophilicity and insolubility in water. See, for instance, "Hydrogels", pages 458-459 in Concise Encyclopedia of Polymer Science and Engineering, Eds. Mark et al., Wiley and Sons, 1990, the disclosure of which is incorporated herein by reference. Although their use is optional in the present invention, the inclusion of hydrogels is highly preferred since they tend to contribute a number of desirable qualities. By virtue of their hydrophilic, water-containing nature, hydrogels generally can:
a) house mesenchymal stems cells,
b) assist the cured composite with load bearing capabilities of the cured composite, and
c) decrease frictional forces on the composite and add thermal elasticity.

Suitable hydrogels generally exhibit an optimal combination of such properties as compatibility with the matrix polymer of choice, and biocompatability.

Where the osteobiologic composition is delivered in conjunction with a strut and therefore is no longer required to bear the majority of loads on the spinal treatment site, the hydrogel phase is preferably between about 50 and about 90 volume percent of the total volume, more preferably between about 70 and about 85 volume percent.

In some embodiments wherein the osteobiologic component is a stand-alone component (i.e., there is essentially no strut), the osetobiologic composition will preferably contain a hydrogel phase at a concentration of between about 15 and 50 volume percent, and preferably between about 20 and about 30 volume percent of the osteobiologic composition. The lower levels of the hydrogel phase provide additional opportunity to use a strong matrix in the osteobiologic component.

Polymer-hydrogel composites demonstrate an optimal combination of physical/chemical properties, particularly in terms of their conformational stability, resorption characteristics, biocompatability, and physical performance, e.g., physical properties such as density, thickness, and surface roughness, and mechanical properties such as load-bearing strength, tensile strength, static shear strength, fatigue of the anchor points, impact absorption, wear characteristics, and surface abrasion.

In general, an unsupported hydrogel is not sufficiently stiff or strong to survive the high spinal loads experienced during the fusion process. Accordingly, in many embodiments of the present invention, the hydrogel is supported not only by the strut component of the present invention, but also by the matrix component of the osteobiologic component. In these cases, the hydrogel is either delivered into the disc space along with the matrix component (as is preferred when the matrix component of the osteobiologic component comprises $CaPO_4$), or is delivered after in-situ porosity has been produced in the matrix component of the osteobiologic component (as with flowable polymers).

However, in some embodiments, the strut component of the present invention may span a sufficiently large portion of the disc space and have sufficient stiffness to adequately support and contain the hydrogel phase within the disc space without the need of a supplemental matrix in the osetobiologic component. In these embodiments, the strut component preferably describes an arc of at least 200 degrees about the disc space, more preferably at least 270 degrees, more preferably at least 350 degrees, and most preferably is about 360 degrees. Such struts are exemplified in FIGS. 2 (*a*) through (*e*), FIGS. 4 (*a*) and (*b*) and FIGS. 5 (*a*) and (*b*).

Therefore, in accordance with the present invention, there is provided an intervertebral body fusion device, comprising:
a) an in situ produced load bearing strut having a shape that spans at least 200 degrees, and
b) an osteobiologic component consisting essentially of: an aqueous phase comprising an osteogenic component.

The hydrogel can include any of the following: polysaccharides, proteins, polyphosphazenes, poly(oxyethylene)-poly(oxypropylene) block polymers, poly(oxyethylene)-poly(oxypropylene) block polymers of ethylene diamine, poly(acrylic acids), poly(methacrylic acids), copolymers of acrylic acid and methacrylic acid, poly(vinyl acetate), and sulfonated polymers.

In general, these polymers are at least partially soluble in aqueous solutions, e.g., water, or aqueous alcohol solutions that have charged side groups, or a monovalent ionic salt thereof. There are many examples of polymers with acidic side groups that can be reacted with cations, e.g., poly (phosphazenes), poly(acrylic acids), and poly(methacrylic acids). Examples of acidic groups include carboxylic acid groups, sulfonic acid groups, and halogenated (preferably fluorinated) alcohol groups. Examples of polymers with basic side groups that can react with anions are poly(vinyl amines), poly(vinyl pyridine), and poly(vinyl imidazole).

Water soluble polymers with charged side groups are cross-linked by reacting the polymer with an aqueous solution containing multivalent ions of the opposite charge, either multivalent cations if the polymer has acidic side groups, or multivalent anions if the polymer has basic side groups. Cations for cross-linking the polymers with acidic side groups to form a hydrogel include divalent and trivalent cations such as copper, calcium, aluminum, magnesium, and strontium. Aqueous solutions of the salts of these cations are added to the polymers to form soft, highly swollen hydrogels.

Anions for cross-linking the polymers to form a hydrogel include divalent and trivalent anions such as low molecular weight dicarboxylate ions, terepthalate ions, sulfate ions, and carbonate ions. Aqueous solutions of the salts of these anions are added to the polymers to form soft, highly swollen hydrogels, as described with respect to cations.

For purposes of preventing the passage of antibodies into the hydrogel, but allowing the entry of nutrients, a useful polymer size in the hydrogel is in the range of between 10,000 D and 18,500 D. Smaller polymers result in gels of higher density with smaller pores.

Ionic polysaccharides, such as alginates or chitosan, can be used to suspend living cells. In one example, the hydrogel is produced by cross-linking the anionic salt of alginic acid, a carbohydrate polymer isolated from seaweed, with ions, such as calcium cations. The strength of the hydrogel increases with either increasing concentrations of calcium ions or alginate. For example, U.S. Pat. No. 4,352,883 describes the ionic cross-linking of alginate with divalent cations, in water, at room temperature, to form a hydrogel matrix.

Tissue precursor cells are mixed with an alginate solution, the solution is delivered to an already implanted support structure and then solidifies in a short time due to the presence in vivo of physiological concentrations of calcium ions. Alternatively, the solution is delivered to the support structure prior to implantation and solidified in an external solution containing calcium ions.

In some embodiments, the hydrogel comprises alginate. Alginate can be gelled under mild conditions, allowing cell immobilization with little damage. Binding of $Mg^{2+}$ and monovalent ions to alginate does not induce gelation of alginate in aqueous solution. However, exposure of alginate to soluble calcium leads to a preferential binding of calcium and subsequent gelling. These gentle gelling conditions are in contrast to the large temperature or solvent changes typically required to induce similar phase changes in most materials.

Alginates have been utilized as immobilization matrices for cell, as an injectable matrix for engineering cartilaginous tissue to treat vesicoureteral reflux in various animal models, and as injectable microcapsules containing islet cells to treat animal models of diabetes.

The open lattice structure and wide distribution of pore sizes in calcium alginate preclude the controlled release of large molecules (e.g., proteins) from these materials and limits the use of pure alginate for entrapment of whole cells or cell organelles. However, alginate membrane can be modified by incorporating other polymeric elements (e.g., lysine, poly(ethylene glycol), poly(vinyl alcohol) or chitosan). These modified systems have been used to control the release of proteins from alginate beads. Haemostatic swabs made of calcium alginate have also been clinically utilized to reduce blood loss during surgical procedures. The calcium ions in alginate may assist the blood clotting process by activating platelets and clotting factor VII.

Collagen-polysaccharide-hydroxyapatite compositions suitable for a matrix of the present invention have been disclosed by Liu in U.S. Pat. No. 5,972,385, the entire teachings of which are incorporated herein by reference. A polysaccharide is reacted with an oxidizing agent to open sugar rings on the polysaccharide to form aldehyde groups. The aldehyde groups are reacted to form covalent linkages to collagen.

The type of polysaccharides which can be used include hyaluronic acid, chondroitin sulfate, dermatan sulfate, keratan sulfate, heparan, heparan sulfate, dextran, dextran sulfate, alginate, and other long chain polysaccharides. In a preferred embodiment, the polysaccharide is hyaluronic acid.

A crosslinked collagen-polysaccharide matrix of the present invention may be used alone to conduct the growth of tissue; in combination with a growth factor to induce the growth of tissue; in combination with fibrin to anchor the matrix into sites of tissue defect, or in combination with both growth factor and fibrin.

The method of making a collagen-polysaccharide matrix of the present invention comprises the steps of oxidizing an exogenous polysaccharide to form a modified exogenous polysaccharide having aldehyde groups, and reacting the modified exogenous polysaccharide with collagen under conditions such that the aldehyde groups covalently react with collagen to form a crosslinked matrix. The method may further comprise the step of adding a growth factor to the matrix. A growth factor can be added before or after the step of reacting the modified polysaccharide with the collagen.

The fibrin used in a crosslinked collagen-polysaccharide matrix of the present invention is prepared by contacting a preformed matrix with a source of fibrinogen and thrombin or by combining the fibrinogen and thrombin with the modified exogenous polysaccharide and collagen at the time of reaction. Alternately, fibrinogen and thrombin in a collagen polysaccharide matrix may be added to another preformed collagen polysaccharide matrix. Therefore, the present invention also comprises a method for preparing a crosslinked collagen-polysaccharide matrix comprising fibrin.

In other embodiments, the hydrogel comprises a microbial polysaccharide. Microbial polysaccharides are ubiquitous in nature and very abundant biopolymers. They are of interest because of their unusual and useful functional properties. Some of these properties are summarized as follows: (i) film-forming and gel-forming capabilities, (ii) stability over broad temperature ranges, (iii) biocompatibility (natural products avoid the release/leaching of toxic metals, residual chemicals, catalyst, or additives), (iv) unusual rheological properties, (v) biodegradability, (vi) water solubility in the native state or reduced solubility if chemically modified, and (vii) thermal processability for some of these polymers. It is worthy to note that gellan, one of the microbial polysaccharides, has been investigated as immobilization materials for enzymes and cells.

In some embodiments, the hydrogel is a synthetic hydrogel. One synthetic hydrogel is polyphosphazene. Polyphosphazenes contain inorganic backbones comprised of alternating single and double bonds between nitrogen and phosphorus atoms, in contrast to the carbon-carbon backbone in most other polymers. The uniqueness of polyphosphazenes stems from the combination of this inorganic backbone with versatile side chain functionalities that can be tailored for different applications. The degradation of polyphosphazenes results in the release of phosphate and ammonium ions along with the side groups.

Linear, uncross-linked polymers such as polyphosphazenes can be prepared by thermal ring opening polymerization of $(NPCl_2)_3$, and the chloro group replaced by amines, alkoxides or organometallic reagents to form hydrolytically stable, high molecular weight poly(organophosphazenes). Depending on the properties of the side groups, the polyphosphazenes can be hydrophobic, hydrophilic or amphiphilic. The polymers can be fabricated into films, membranes and hydrogels for biomedical applications by cross-linking or grafting. Bioerodible polymers for drug delivery devices have been prepared by incorporating hydrolytic side chains of imidazole for skeletal tissue regeneration.

Polyphosphazenes are polymers with backbones consisting of nitrogen and phosphorous atoms separated by alternating single and double bonds. Each phosphorous atom is covalently bonded to two side chains. Polyphosphazenes that can be used have a majority of side chains that are acidic and capable of forming salt bridges with di- or trivalent cations. Examples of acidic side chains are carboxylic acid groups and sulfonic acid groups.

Bioerodible polyphosphazenes have at least two differing types of side chains, acidic side groups capable of forming salt bridges with multivalent cations, and side groups that hydrolyze under in vivo conditions, e.g., imidazole groups, amino acid esters, glycerol, and glucosyl. Bioerodible or biodegradable polymers, i.e., polymers that dissolve or degrade within a period that is acceptable in the desired application (usually in vivo therapy), will degrade in less than about five years and most preferably in less than about one year, once exposed to a physiological solution of pH 6-8 having a temperature of between about 25° C. and 38° C. Hydrolysis of the side chain results in erosion of the polymer. Examples of hydrolyzing side chains are unsubstituted and substituted imidizoles and amino acid esters in which the side chain is bonded to the phosphorous atom through an amino linkage.

Methods for synthesis and the analysis of various types of polyphosphazenes are described in U.S. Pat. Nos. 4,440,921, 4,495,174, and 4,880,622, the entire teachings of which are incorporated herein by reference. Methods for the synthesis of the other polymers described above are known to those skilled in the art. See, for example Concise Encyclopedia of Polymer Science and Engineering, J. I. Kroschwitz, editor John Wiley and Sons, New York, N. Y., 1990, the entire teachings of which are incorporated herein by reference. Many polymers, such as poly(acrylic acid), alginates, and PLURONICS™, are commercially available.

Another synthetic hydrogel is poly(vinyl)alcohol (PVA). PVA is not synthesized directly but is the deacetylated product of poly(vinyl acetate). Polyvinyl acetate is usually prepared by radical polymerization of vinyl acetate (bulk, solution or emulsion polymerizations). PVA is formed by either alcoholysis, hydrolysis or aminolysis processes of poly(vinyl acetate). The hydrophilicity and water solubility of PVA can be readily controlled by the extent of hydrolysis and molecular weight. PVA has been widely used as thickening and wetting agent.

PVA gels can be prepared by cross-linking with formaldehyde in the presence of sulfuric acid. These formaldehyde-cross-linked PVA materials have been used as prosthesis for a variety of plastic surgery applications including breast augmentation, diaphragm replacement and bone replacement. However, a variety of complications were found after long term implantation, including calcification of the PVA.

More recently, PVA was made into an insoluble gel using a physical cross-linking process. These gels were prepared with a repeated freezing-thawing process. This causes structural densification of the hydrogel due to the formation of semicrystalline structures. The use of this gel in drug delivery applications has been reported. However, PVA is not truly biodegradable due to the lack of labile bonds within the polymer bond. Only low molecular weight materials are advisable to be used as implant materials.

Another synthetic hydrogel is polyethylene oxide (PEO). PEO can be produced by the anionic or cationic polymerization of ethylene oxide using a variety of initiators. PEO is highly hydrophilic and biocompatible, and has been utilized in a variety of biomedical applications including preparation of biologically relevant conjugates, induction of cell membrane fusion and surface modification of biomaterials. Different polymer architectures have been synthesized and some of their applications in medicine have been recently reviewed. For example, PEO can be made into hydrogels by γ-ray or electron beam irradiation and chemical crosslinking. These hydrogels have been used as matrices for drug delivery and cell adhesion studies.

Pluronic polyols or polyoxamers are block copolymers of PEO and poly(propylene oxide) and are usually synthesized by anionic polymerization in the form of an ABA triblock using a difunctional initiator. Pluronics F 127, which contains 70% ethylene oxide and 30% propylene oxide by weight with an average molecular weight of 11,500, is the most commonly used gel-forming polymer matrix to deliver proteins.

This polymer exhibits a reversible thermal gelation in aqueous solutions at a concentration of 20% or more. Thus, the polymer solution is a liquid at room temperature but gels rapidly in the body. Although the polymer is not degraded by the body, the gels dissolve slowly and the polymer is eventually cleared. This polymer has been utilized in protein delivery and skin burn treatments.

Although PGA is not water soluble, bioerodible hydrogels based on photopolymerized PGA-PEO copolymers have been synthesized and their biological activities investigated. Macromonomers having a poly(ethylene glycol) central block, extended with oligomers of .alpha.-hydroxy acids (e.g., oligo(dl-lactic acid) or oligo(glycolic acid)) and terminated with acrylate groups were synthesized. These hydrogels were designed to form direct contacts with tissues or proteins following photopolymerization, and act as a barrier.

These gels degrade upon hydrolysis of the oligo(α-hydroxy acid) regions into poly(ethylene glycol), the .alpha.-hydroxy acid, and oligo(acrylic acid). The degradation rate of these gels could be tailored from less than 1 day to 4 months by appropriate choice of the oligo(.alpha.-hydroxy acid). The macromonomer could be polymerized using non-toxic photoinitiators with visible light without excess heating or local toxicity. The hydrogels polymerized in contact with tissue adhere tightly to the underlying tissue. In contrast, the gels were nonadhesive if they were polymerized prior to contact with tissue. These hydrogels have been utilized in animal models to prevent post-surgical adhesion and thrombosis of blood vessels and intimal thickening following balloon catheterization.

It can thus be seen that there are a large number of synthetic biodegradable polymers that may be used in the spinal tissue engineering invention described herein. Established polymer chemistries enable one to tailor properties of the synthetic polymers by using different i) functional groups (either on the backbone or side chain), ii) polymer architectures (linear, branched, comb or star), and iii) combinations of polymer species physically mixed (polymer blends or interpenetrating networks) or chemically bonded (copolymers). The current preference for PGA and related polyesters is partially due to their established safety in human applications, and the projected approval of the Food and Drug Administration. PLGA can also be used with specific peptide sequences incorporated into the polymer. Polymers constituted of building blocks similar to components of ECM, e.g., carbohydrates and peptides, may also be used.

Other hydrogels that can be used in the methods of the invention are solidified by either visible or ultraviolet light. These hydrogels are made of macromers including a water soluble region, a biodegradable region, and at least two polymerizable regions as described in U.S. Pat. No. 5,410,016, the entire teachings of which are incorporated herein by reference. For example, the hydrogel can begin with a biodegradable, polymerizable macromer including a core, an extension on each end of the core, and an end cap on each extension. The core is a hydrophilic polymer, the extensions are biodegradable polymers, and the end caps are oligomers capable of cross-linking the macromers upon exposure to visible or ultraviolet light, e.g., long wavelength ultraviolet light.

Examples of such light solidified hydrogels include polyethylene oxide block copolymers, polyethylene glycol polylactic acid copolymers with acrylate end groups, and 10 K polyethylene glycol-glycolide copolymer capped by an acrylate at both ends. As with the PLURONIC™ hydrogels, the copolymers comprising these hydrogels can be manipulated by standard techniques to modify their physical properties such as rate of degradation, differences in crystallinity, and degree of rigidity.

It is known that stem cells are fairly sensitive to temperatures greatly in excess of body temperature. Therefore, in some embodiments of the present invention, the osteobiologic composition is delivered into the disc space at a temperature of between about 37° C. and about 60° C., preferably between about 40° C. and about 50° C., more preferably between about 40° C. and about 45° C.

In some embodiments, a semipermeable membrane is formed around the hydrogel to protect the cells inside. In these instances, the techniques disclosed in U.S. Pat. No. 4,352,883 by Lin, the entire teachings of which are incorporated herein by reference (hereinafter "Lin"), are used.

In one aspect, the instant invention provides a method of encapsulating bone growth cells or growth factors in a semipermeable membrane. The basic approach involves suspending the bone growth cells or growth factors to be encapsulated in a physiologically compatible medium containing a water-soluble substance that can be made insoluble in water, that is, gelled, to provide a temporary protective environment for the tissue. The medium is next formed into droplets containing the bone growth cells or growth factors and gelled, for example, by changing conditions of temperature, pH, or ionic environment. The "temporary capsules" thereby produced are then subjected to a treatment, which can be a known treatment, that results in the production of membranes of a controlled permeability (including impermeability) about the shape-retaining temporary capsules.

The temporary capsules can be fabricated from any non-toxic, water soluble substance that can be gelled to form a shape retaining mass by a change of conditions in the medium in which it is placed, and also may comprise plural groups that are readily ionized to form anionic or cationic groups. The presence of such groups in the polymer enables surface layers of the capsule to be cross-linked to produce a "permanent" membrane when exposed to polymers containing multiple functionalities of the opposite charge.

The presently preferred material for forming the temporary capsules is polysaccharide gums, either natural or synthetic, of the type which can be (a) gelled to form a shape retaining mass by being exposed to a change in conditions such as a pH change or by being exposed to multivalent cations such as $Ca^{++}$; and (b) permanently "crosslinked" or hardened by polymers containing reactive groups such as amine or imine groups which can react with acidic polysaccharide constituents. The presently preferred gum is alkali metal alginate. Other water soluble gums which may be used include guar gum, gum arabic, carrageenan, pectin, tragacanth gum, xanthan gum or acidic fractions thereof. When encapsulating thermally refractory materials, gelatin or agar may be used in place of the gums.

The preferred method of formation of the droplets is to force the gum-nutrient-tissue suspension through a vibrating capillary tube placed within the center of the vortex created by rapidly stirring a solution of a multivalent cation. Droplets ejected from the tip of the capillary immediately contact the solution and gel as spheroidal shaped bodies.

The preferred method of forming a permanent semipermeable membrane about the temporary capsules is to "cross-link" surface layers of a gelled gum of the type having free acid groups with polymers containing acid reactive groups such as amine or imine groups. This is typically done in a dilute solution of the selected polymer. Generally, the lower the molecular weight of the polymer, the greater the penetration into the surface of the temporary capsule, and the greater the penetration, the less permeable the resulting membrane. Permanent crosslinks are produced as a consequence of salt formation between the acid reactive groups of the crosslinking polymer and the acid groups of the polysaccharide gum. Within limits, semipermeability can be controlled by setting the molecular weight of the crosslinking polymer, its concentration, and the duration of reaction. Crosslinking polymers which have been used with success include polyethylenimine and polylysine. Molecular weight can vary, depending on the degree of permeability required, between about 3,000 and about 100,000 or more. Good results have been obtained using polymers having an average molecular weight on the order of about 35,000.

The capsules can be engineered to have a selected in vivo useful life by astute selection of the cross-linking polymer. Proteins or polypeptide crosslinkers, e.g., polylysine, are readily attached in vivo resulting in relatively rapid destruction of the membrane. Cross-linkers not readily degradable in mammalian bodies, e.g., polyethyleneimine, result in longer lasting membranes. By selecting the crosslinking polymer or by cross-linking simultaneously or sequentially with two or more such materials, it is possible to preselect the length of time the implanted tissue remains protected.

Optionally, with certain materials used to form the temporary capsules, it is possible to improve mass transfer within the capsule after formation of the permanent membrane by re-establishing the conditions under which the material is liquid, e.g., removing the multivalent cation. This can be done by ion exchange, e.g., immersion in phosphate buffered saline or citrate buffer. In some situations, such as where it is desired to preserve the encapsulated tissue, or where the temporary gelled capsule is permeable, it may be preferable to leave the encapsulated gum in the crosslinked, gelled state.

An alternative method of membrane formation involves an interfacial polycondensation of polyaddition. This approach involves preparing a suspension of temporary capsules in an aqueous solution of the water soluble reactant of a pair of complementary monomers which can form a polymer. Thereafter, the aqueous phase is suspended in a hydrophobic liquid in which the complementary reactant is soluble. When the second reactant is added to the two-phase system, polymerization takes place at the interface. Permeability can be controlled by controlling the makeup of the hydrophobic solvent and the concentration of the reactants. Still another way to form a semipermeable membrane is to include a quantity of protein in the temporary capsule which can thereafter be crosslinked in surface layers by exposure to a solution of a crosslinking agent such as gluteraldehyde.

The foregoing process has been used to encapsulate viable mesenchymal stems cells which, in a medium containing the nutrients and other materials necessary to maintain viability and support in vitro metabolism of the tissue, provide bone growth.

In another aspect, the instant invention provides a tissue implantation method which does not require surgery and which overcomes many of the problems of immune rejection. In accordance with the invention, the capsules are injected into a suitable site in a mammalian body, and function normally until the tissue expires, or until natural body processes succeed in isolating the capsules so that substances required for viability of the tissue are no longer available. At this point, because surgery is not required for the implant, fresh tissue may be readily provided by another injection. The mammalian body may accordingly be provided with the specialized function of the tissue as long as desired.

In a preferred embodiment of the invention, mammalian mesenchymal stems cells are encapsulated in polylysine and polyethyleneimine cross-linked alginate membranes. These may be injected into the polymer matrix of the osteobiologic component.

Accordingly, it is a primary object of the invention to provide a method of encapsulating living a osteogenic component or growth factors within a membrane permeable to the nutrients and other substances needed for maintenance and metabolism and to metabolic products, but impermeable to the polymer matrix material having a molecular weight above a selected level.

Other objects of the invention are to provide a method of implanting living tissue in mammalian bodies and to provide a non-surgical tissue implantation technique. Still another object is to provide a method of encapsulating living tissue which allows the production of capsules having a high surface area to volume ratio and membranes with a preselected in vivo residence time.

Each of IPNs and S-IPNs are extremely desirable because cells can be suspended in the polymer solutions which can be cross-linked by a non-toxic active species, such as by photoinitiation. In some embodiments, both the active species, and the initiator are present in an amount that is non-toxic to cells. In other embodiments, the active species is present in an amount that is non-toxic to cells and the initiation occurs via photoinitiation.

Cells can be obtained directed from a donor, from cell culture of cells from a donor, or from established cell culture lines. In the preferred embodiments, cells are obtained directly from a donor, washed and implanted directly in combination with the polymeric material. The cells are cultured using techniques known to those skilled in the art of tissue culture.

Cell attachment and viability can be assessed using scanning electron microscopy, histology, and quantitative assessment with radioisotopes. The function of the implanted cells can be determined using a combination of the above-techniques and functional assays. For example, in the case of hepatocytes, in vivo liver function studies can be performed by placing a cannula into the recipient's common bile duct. Bile can then be collected in increments. Bile pigments can be analyzed by high pressure liquid chromatography looking for underivatized tetrapyrroles or by thin layer chromatography after being converted to azodipyrroles by reaction with diazotized azodipyrroles ethylanthranilate either with or without treatment with P-glucuronidase. Diconjugated and monoconjugated bilirubin can also be determined by thin layer chromatography after alkalinemethanolysis of conjugated bile pigments. In general, as the number of functioning transplanted hepatocytes increases, the levels of conjugated bilirubin will increase. Simple liver function tests can also be done on blood samples, such as albumin production. Analogous organ function studies can be conducted using techniques known to those skilled in the art, as required to determine the extent of cell function after implantation. For example, islet cells of the pancreas may be delivered in a similar fashion to that specifically used to implant hepatocytes, to achieve glucose regulation by appropriate secretion of insulin to cure diabetes. Other endocrine tissues can also be implanted. Studies using labeled glucose as well as studies using protein assays can be performed to quantitate cell mass on the polymer scaffolds. These studies of cell mass can then be correlated with cell functional studies to determine what the appropriate cell mass is. In the case of chondrocytes, function is defined as providing appropriate structural support for the surrounding attached tissues.

This technique can be used to provide multiple cell types, including genetically altered cells, within a three-dimensional scaffolding for the efficient transfer of large number of cells and the promotion of transplant engraftment for the purpose of creating a new tissue or tissue equivalent. It can also be used for immunoprotection of cell transplants while a new tissue or tissue equivalent is growing by excluding the host immune system.

Examples of cells which can be implanted as described herein include chondrocytes and other cells that form cartilage, osteoblasts and other cells that form bone, muscle cells, fibroblasts, and organ cells. As used herein, "organ cells" includes hepatocytes, islet cells, cells of intestinal origin, cells derived from the kidney, and other cells acting primarily to synthesize and secret, or to metabolize materials.

In some embodiments, the osteobiologic component comprises an osteoconductive phase. In some embodiments, the osteoconductive phase comprises a particulate phase comprising a hard tissue, osteoconductive or osteoinductive calcium containing, non-fibrous, powdered compound, wherein the calcium containing compound comprises a material having the formula:

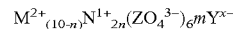

where n=1-10, and m=2 when x=1, and/or m=1 when x=2 where M and N are alkali or alkaline earth metals, preferably calcium, magnesium, sodium, zinc and potassium. $ZO_4$ is an acid radical, where Z is preferably phosphorus, arsenic, vanadium, sulfur or silicon, or is substituted in whole or part with carbonate ($CO_3^{2-}$. Y is an anion, preferably halide, hydroxide, or carbonate.

Most preferably, the calcium containing compound comprises mono-, di-, octa-, .alpha.-tri-, .beta.-tri-, or tetra-calcium phosphate, hydroxyapatite, fluorapatite, calcium sulfate, calcium fluoride and mixtures thereof.

The calcium containing bone regenerating compound can also contain a bioactive glass comprising metal oxides such as calcium oxide, silicon dioxide, sodium oxide, phosphorus pentoxide, and mixtures thereof, and the like.

Preferably, the calcium containing compound used in the composites of the present invention will have a particle size of about 10 microns to about 1000 microns, and most preferably about 100 microns to about 500 microns. The particles are prepared by conventional processes such as pulverizing, milling, and the like.

In some embodiments, hydroxyapatite particles are preferably the type of dry free-flowing hydroxyapatite particles supplied for use in forming wetted, loose-mass implants, and can be obtained commercially from Orthomatrix Corporation (Dublin, Calif.) or Calcitek (San Diego, Calif.). Particle sizes of between about 250 and 2000 microns are preferred, smaller particles showing increased difficulty in allowing tissue ingrowth and larger particles requiring increased quantities of binder for ease of application.

In some embodiments, the material comprising the osteobiologic component of the present invention has at least one of the following intrinsic properties:

| Intrinsic Property | Preferred Value | More Preferred Value |
| --- | --- | --- |
| Compression Strength | >1 MPa | >10 MPa |
| Fracture Strength | >1 MPa | >10 MPa |
| Compression Modulus | 0.1-2 GPa | 0.2-0.7 GPa |

In some embodiments, the osteobiologic component of the present invention has the following mechanical performance characteristics:

| Mechanical Property | Preferred Value | More Preferred Value |
| --- | --- | --- |
| Static Compressive Load | >2 kN | >4 kN |

One example of such an osteobiologic composition comprises an in situ formed, porous, polyoxaester scaffold that occupies the space created by the strut described in FIGS. 2 (*f*) and 2 (*g*).

In some embodiments, the polymer has a Tm of no more than about 80° C. This allows the use of water or steam as the heating fluid. In some embodiments, the polymer has a Tm of less than 100° C., and so is less likely to damage surrounding tissue.

In particular, preferred embodiments, in the solidifed form, exhibit mechanical properties approximating those of the cancellous bone. For instance, preferred embodiments of the osetobiologic composition exhibit a load bearing strength of between about 50 and about 200 psi (pounds per square inch), and preferably between about 100 and about 150 psi. Such composites also exhibit a shear stress of between about 10 and 100 psi, and preferably between about 30 and 50 psi, as such units are typically determined in the evaluation of natural tissue and joints.

As used herein, the term "growth factors" encompasses any cellular product that modulates the growth or differentiation of other cells, particularly connective tissue progenitor cells. The growth factors that may be used in accordance with the present invention include, but are not limited to, FGF-1, FGF-2, FGF-4, PDGFs, EGFs, IGFs, PDGF-bb, bone morphogenetic protein-1, bone morphogenetic protein-2, OP-1, transforming growth factor-β, osteoid-inducing factor (OIF), angiogenin(s), endothelins, hepatocyte growth factor and keratinocyte growth factor, osteogenin (bone morphogenetic protein-3); bone morphogenetic protein-2; OP-1; bone morphogenetic protein-2A, -2B, and -7; transforming growth factor-β, HBGF-1 and -2; isoforms of platelet-derived growth factors (PDGF), fibroblast growth factors, epithelial growth factors, isoforms of transforming growth factor-β, insulin-like growth factors, and bone morphogenic proteins, and FGF-1 and 4.

Growth factors which can be used with a matrix of the present invention include, but are not limited to, members of the transforming growth factor-β superfamily, including transforming growth factor-β1,2 and 3, the bone morphogenetic proteins (BMP's), the growth differentiation factors (GDF's), and ADMP-1; members of the fibroblast growth factor family, including acidic and basic fibroblast growth factor (FGF-1 and -2); members of the hedgehog family of proteins, including indian, sonic and desert hedgehog; members of the insulin-like growth factor (IGF) family, including IGF-I and -II; members of the platelet-derived growth factor (PDGF) family, including PDGF-AB, PDGF-BB and PDGF-AA; members of the interleukin (IL) family, including IL-1 thru-6; and members of the colony-stimulating factor (CSF) family, including CSF-1, G-CSF, and GM-CSF.

As noted above, there is a concern that including osteogenic components and osteoinductive components in a heated polymer matrix may render nonviable or denature these components. However, there are some growth factors known to those skilled in the art that are more heat resistant than the majority of growth factors. It is believed that these high temperature growth factors in osteobiologic compositions may be included in osteobiologic compositions that are to be flowed into the disc space at temperatures between body temperature and about 45° C.

Accordingly, in one embodiment, the present invention is a pharmaceutical composition comprising a pharmaceutically acceptable carrier or diluent and (a) at least one polymer flowable between 38° C. and 45° C. selected from the group consisting of homopolymers of poly(ε-caprolactone), poly(p-dioxanone), or poly(trimethylene carbonate) or copolymers or mixtures thereof, or copolyesters of p-dioxanone or trimethylene carbonate and glycolide or lactide or mixtures thereof, and in particular, copolymers of p-dioxanone/glycolide, p-dioxanone/lactide, trimethylene carbonate/glycolide and trimethylene carbonate/lactide, or copolyesters of .epsilon.-caprolactone and glycolide or mixtures thereof, or mixtures of homopolymers of ε-caprolactone and lactide, and (b) at least one growth factor resistant to denaturing at at least about 45° C. selected from the group consisting of bone morphogenetic proteins.

As used herein, a "pharmaceutical composition" is a formulation comprising the disclosed compounds and a pharmaceutically acceptable diluent or carrier, in a form suitable for administration to a subject. The quantity of active ingredient (e.g. a growth factor) in a unit dose of composition is an effective amount and may be varied according to the particular treatment involved. As used herein, an "effective amount" of a compound is the quantity which, when administered to a subject in need of treatment, improves the prognosis of the subject, e.g. reduces the severity of one or more of the subject's symptoms associated with a spinal injury. It may be appreciated that it may be necessary to make routine variations to the dosage depending on the age and condition of the patient. The amount of the active ingredient to be administered to a subject will depend on the type of injury and the characteristics of the subject, such as general health, other diseases, age, sex, genotype, body weight and tolerance to drugs. The skilled artisan will be able to determine appropriate dosages depending on these and other factors.

The compounds described herein can be used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein. Techniques for formulation and administration of the compounds of the instant invention can be found in Remington: the Science and Practice of Pharmacy, 19$^{th}$ edition, Mack Publishing Co., Easton, Pa. (1995).

Preferably, the matrix material becomes flowable in the temperature range of at least 40° C. and 55° C., more preferably in the temperature range of at least 45° C. and 50° C.

Preferably, the growth factor is resistant to denaturing at a temperature of at least 40° C. In some embodiments, the growth factor is a dimer. In some embodiments, the growth factor is a bone morphogenetic protein dimer.

If desired, substances such as antibiotics, antibacterial agents, and antifungal agents may also be admixed with the polymer. Examples of antimicrobial agents which may be employed include tetracycline, oxytetracycline, chlorotetracycline, neomycin, erythromycin, and its derivative, bacitracin, streptomycin, rifampicin and its derivatives such as N-dimethylrifampicin, kanamycin and chloromycetin. Useful antifungal agents include griseofulvin, mycostatin, miconazole and its derivatives as described in U.S. Pat. No. 3,717,655, the entire teachings of which are incorporated herein by reference; bisdiguanides such as chlorhexidine; and more particularly quaternary ammonium compounds such as domiphen bromide, domiphen chloride, domiphen fluoride, benzalkonium chloride, cetyl pyridinium chloride, dequalinium chloride, the cis isomer of 1-(3-chlorallyl)-3, 5,7-triaza-1-azoniaadamantane chloride (available commercially from the Dow Chemical Company under the trademark Dowicil 200) and its analogues as described in U.S. Pat. No. 3,228,828, the entire teachings of which are incorporated herein by reference, cetyl trimethyl ammonium bromide as well as benzethonium chloride and methylbenzethonium chloride such as described in U.S. Pat. Nos. 2,170,111, 2,115,250 and 2,229,024, the entire teachings of which are incorporated herein by reference; the carbanilides and salicylanilides such 3,4,4'-trichlorocarbanilide, and 3,4'5-tribromosalicylanilide; the hydroxydiphenyls such as dichlorophene, tetrachlorophene, hexachlorophene, and 2,4, 4'-trichloro-2'-hydroxydiphenylether; and organometallic and halogen antiseptics such as sinc pyrithione, silver sulfadiazone, silver uracil, iodine, and the iodophores derived from non-ionic surface active agents such as are described in U.S. Pat. Nos. 2,710,277 and 2,977,315, the entire teachings of which are incorporated herein by reference, and from polyvinylpyrrolidone such as described in U.S. Pat. Nos. 2,706,701, 2,826,532 and 2,900,305, the entire teachings of which are incorporated herein by reference.

Optionally, the matrix has antibodies that have affinity for connective tissue progenitor stem cells bound to the surface thereof. Suitable antibodies, include by way of example, STRO-1, SH-2, SH-3, SH-4, SB-10, SB-20, and antibodies to alkaline phosphatase. Such antibodies are described in Haynesworth et al., *Bone* (1992), 13:69-80; Bruder, S. et al., *Trans Ortho Res Soc* (1996), 21:574; Haynesworth, S. E., et al., *Bone* (1992), 13:69-80; Stewart, K., et al, *J Bone Miner Res* (1996), 11(Suppl.):S142; Flemming J E, et al., in "Embryonic Human Skin. Developmental Dynamics," 212: 119-132, (1998); and Bruder S P, et al., *Bone* (1997), 21(3): 225-235, the entire teachings of which are incorporated herein by reference.

In U.S. Pat. No. 6,197,325, the entire teachings of which are incorporated herein by reference, Mac Phee discloses that drugs, polyclonal and monoclonal antibodies and other compounds, including, but not limited to, DBM and bone morphogenetic proteins may be added to the matrix, such as a matrix of the present invention. They accelerate wound healing, combat infection, neoplasia, and/or other disease processes, mediate or enhance the activity of the growth factor in the matrix, and/or interfere with matrix components which inhibit the activities of the growth factor in the matrix. These drugs may include, but are not limited to: antibiotics, such as tetracycline and ciprofloxacin; antiproliferative/cytotoxic drugs, such as 5-fluorouracil (5-FU), taxol and/or taxotere; antivirals, such as gangcyclovir, zidovudine, amantidine, vidarabine, ribaravin, trifluridine, acyclovir, dideoxyuridine and antibodies to viral components or gene products; cytokines, such as $\alpha$- or $\beta$- or $\gamma$-Interferon, $\alpha$- or $\beta$-tumor necrosis factor, and interleukins; colony stimulating factors; erythropoietin; antifungals, such as diflucan, ketaconizole and nystatin; antiparasitic agents, such as pentamidine; anti-inflammatory agents, such as $\alpha$-1-anti-trypsin and $\alpha$-1-antichymotrypsin; steroids; anesthetics; analgesics; and hormones. Other compounds which may be added to the matrix include, but are not limited to: vitamins and other nutritional supplements; hormones; glycoproteins; fibronectin; peptides and proteins; carbohydrates (both simple and/or complex); proteoglycans; antiangiogenins; antigens; oligonucleotides (sense and/or antisense DNA and/or RNA); bone morphogenetic proteins; DBM; antibodies (for example, to infectious agents, tumors, drugs or hormones); and gene therapy reagents. Genetically altered cells and/or other cells may also be included in the matrix of this invention.

If desired, substances such as pain killers and narcotics may also be admixed with the polymer for delivery and release to the disc space.

In some embodiments of the resent invention, the additive is embedded within the matrix material of the scaffold. In other embodiments, the additive resides on the inner surface of the open porosity created by the leaching of the leachate. In other embodiments, the additive resides within the hydrogel phase.

When the osteobiologic composition comprises one or more bone morphogenetic proteins, they are preferably located on the inner surface of the open porosity in the case where the scaffold is formed prior to being populated with cells, and are preferably located within the hydrogel phase in the case where a hydrogel is used to deliver cells at the same time the scaffold is delivered. This is done so that the cells will contact the bone morphogenetic proteins as soon as possible following implantation in order to initiate the bone forming process. Furthermore, since the bone morphogenetic proteins have a limited time in which they are active in inducing cells to form bone, it is important to expose the cells to the bone morphogenetic proteins as soon as possible to take maximum advantage of their potency.

When osteoprogenitor cells are seeded onto the scaffold following in situ formation of the scaffold, they preferably adhere to the surface of the inner porosity of the scaffold. This is important because osteoprogenitor cells must attach to a substrate in order to begin forming bone. Likewise when osteoprogenitor cells are delivered to the fusion site while encapsulated in a hydrogel, they preferably attach to the inner porosity of the hydrogel.

In some embodiments, bone morphogenetic protein is present in the scaffold in a concentration of at least 2 times the atologus concentration. More preferably, the bone morphogenetic protein is present in the scaffold in a concentration of at least 100 times the autologous concentration.

In some embodiments, mesenchymnal stem cells are present in the scaffold in a concentration of at least 2 times the autologous concentration. More preferably the mesenchymnal stem cells are present in the scaffolding in a concentration of 10 times the autologous concentration, and most preferably they are present in a concentration of 100 times the autologous concentration.

In some embodiments, the osteobiologic composition has a sufficiently high osteobiologic nature and a matrix that is sufficiently resistant to degradation that the bone growth essentially fills the entire porosity of the scaffold of the osteobiologic composition before there is any significant degradation of the matrix. In such a case, the new bone can begin to significantly share the compressive load experienced by the device before the device undergoes a significant loss in strength.

In preferred embodiments, bony ingrowth penetrates at least 50% of the distance to the center of the implant before the matrix loses 50% of its weight. In more preferred embodiments, bony ingrowth penetrates at least 75% of the distance to the center of the implant before the matrix loses 25% of its weight. In more preferred embodiments, bony ingrowth penetrates at least 90% of the distance to the center of the implant before the matrix loses 10% of its weight.

In preferred embodiments, bony ingrowth penetrates at least 50% of the distance to the center of the implant before the matrix loses 50% of its compressive strength. In more preferred embodiments, bony ingrowth penetrates at least 75% of the distance to the center of the implant before the matrix loses 25% of its compressive strength. In more preferred embodiments, bony ingrowth penetrates at least 90% of the distance to the center of the implant before the matrix loses 10% of its compressive strength.

In accord with the present invention, the injectable implants of the invention can be used to fuse facets and to fuse the interspinous region. In some embodiments, the implants of the present invention use an elastomer to tension the interspinous region to correct lordotic angle.

It is further believed that the above noted osteobiologic compositions can be advantageously used in vertebroplasty procedures, particularly when delivered into the porosity of a skeleton created in the vertebral body, as disclosed in U.S. patent application by Martin Reynolds entitled "Method of Performing Embolism Free Vertebroplasty and Devise Therefore," which was filed on Nov. 21, 2002, the entire teachings of which are incorporated herein by reference.

Additional Embodiments

In one embodiment, the present invention is an intervertebral fusion device for providing bony fusion across a disc space. The device comprises a strut. The strut includes an upper surface for bearing against the upper endplate, a lower surface for bearing against the lower endplate, and an in-situ formed load bearing composition disposed between the upper and lower surfaces.

In another embodiment, the present invention is an intervertebral fusion device comprising a strut, having a shape memory, and an in-situ formed osteobiologic component. The strut further includes (i) an upper surface for bearing against the upper endplate and (ii) a lower surface for bearing against the lower endplate.

In another embodiment, the present invention is an intervertebral fusion device comprising a strut and an in-situ formed osteobiologic component. The strut includes an upper surface for bearing against the upper endplate, and a lower surface for bearing against the lower endplate. The in-situ formed osteobiologic component includes a matrix component having an internal surface defining a scaffold having open porosity suitable for bone growth therethrough, and an osteogenic component located within the open porosity.

In another embodiment, the present invention is an intervertebral fusion device comprising a strut and an in-situ formed osteobiologic component. The strut includes an upper surface for bearing against the upper endplate, and a lower surface for bearing against the lower endplate. The in-situ formed osteobiologic component includes an injectable matrix component, and an osteoinductive component embedded within the matrix.

In another embodiment, the present invention is an intervertebral fusion device comprising a strut and an in-situ formed osteobiologic component. The strut includes an upper surface for bearing against the upper endplate, and a lower surface for bearing against the lower endplate. The in-situ formed osteobiologic component includes an injectable matrix component, and a porogen embedded within the matrix.

In another embodiment, the present invention is an intervertebral fusion device comprising a strut and an in-situ formed osteobiologic component. The strut includes an upper surface for bearing against the upper endplate, and a lower surface for bearing against the lower endplate. The in-situ formed osteobiologic component includes an expandable device defining a cavity, and an injectable osteobiologic composition located within the cavity.

In another embodiment, the present invention is an intervertebral fusion device comprising a strut that includes an expandable device having a cavity, an upper surface for bearing against the upper endplate, a lower surface for bearing against the lower endplate, and an inner wall defining a through hole. The strut further includes an injectable load bearing composition located within the cavity. The fusion device further includes an osteobiologic component located in the throughhole.

In another embodiment, the present invention is an intervertebral fusion device comprising a strut and an in-situ formed osteobiologic component. The strut includes an upper surface for bearing against the upper endplate a lower surface for bearing against the lower endplate. Preferably, the in-situ formed osteobiologic component includes an injectable, matrix component essentially free of monomer.

In another embodiment, the present invention is an intervertebral fusion device for providing bony fusion across a disc space, comprising a strut. The strut includes an upper surface for bearing against the upper endplate, a lower surface for bearing against the lower endplate, and an in-situ formed load bearing composition disposed between the upper and lower surfaces and made of a material comprising a cross-linked resorbable polymer.

The Preferred Embodiments

As used herein, the term "toroid" refers to a surface obtained by at least partially rotating a closed curve, which lies in a plane, about an axis parallel to the plane and which does not intersect the curve. An example of an "open cavity defined by an outer surface of a toroid" is a hole.

In one preferred embodiment, the present invention is an intervertebral spinal fusion device comprising at least one arcuate inflatable balloon that upon expansion between two adjacent vertebrae at least partially restores natural a natural angle between two adjacent vertebrae, said device having a footprint that substantially corresponds to a perimeter of a vertebral endplate.

Preferably, the intervertebral spinal fusion device has an upper area, a lower area, an anterior area and a posterior area. Upon inflation, said device can have a footprint that substantially corresponds to a rim of a vertebral endplate and said anterior area height being greater than said posterior area height. More preferably, upon expansion, at least a portion of the device has a generally toroidal shape thereby defining an open cavity having an axial dimension and a radial dimension. In one embodiment, the device comprises at least one expandable balloon that contains a plurality of lumena.

In a particularly preferred embodiment, the device comprises at least one said balloon including a resorbable, semi-permeable material selected from the group consisting of polyolefin copolymers, polyethylene, polycarbonate, polyethylene terephthalate, ether-ketone polymers, woven fibers, nonwoven fibers, fabrics and metal mesh.

In a preferred embodiment, the balloon defines at least one opening.

In another embodiment, the upper and lower areas of the device have a plurality of outward projections. The outward projections preferably include polyetherether ketone (PEEK).

The upper area of the device can include at least one material selected from the group consisting of polyether block copolymer (PEBAX), ABS (acrylonitrile butadiene styrene), ANS (acrylonitrile styrene), delrin acetal; PVC (polyvinyl chloride), PEN (polyethylene napthalate), PBT (polybutylene terephthalate), polycarbonate, PEI (polyetherimide), PES (polyether sulfone), PET (polyethylene terephthalate), PETG (polyethylene terephthalate glycol), polyamide, aromatic polyamide, polyether, polyester, polymethylmethacrylate, polyurethane copolymer, ethylene vinyl acetate (EVA), ethylene vinyl alcohol, polyethylene, latex rubber, FEP (fluorinated ethylene polymer), PTFE (polytetrafluoroethylene), PFA (perfluoro-alkoxyalkane), polypropylene, polyolefin, polysiloxane, liquid crystal polymer, ionomer, poly(ethylene-co-methacrylic) acid, silicone rubber, SAN (styrene acrylonitrile), nylon, polyether block amide and thermoplastic elastomer.

In one preferred embodiment, the device of the present invention has at least one balloon that contains at least one member of the group consisting of a load-bearing component and an osteobiologic component. The load-bearing and the osteobiologic components can be used alone or in combination. Combination is preferred. In a particularly preferred embodiment, the load-bearing and the osteobiological components are resorbable.

The load-bearing component can comprise at least one compound selected from the group consisting of poly(lactic acid), poly(glycolic acid), p-dioxanone fibers, polyarylethyl, polymethylmethacrylate, polyurethane, amino-acid-derived polycarbonate, polycaprolactone, aliphatic polyesters, calcium phosphate, unsaturated linear polyesters, vinyl pyrrolidone and polypropylene fumarate diacrylate, or mixtures thereof.

The osteobiologic component can include at least one element selected from the group consisting of mesenchymal stem cells, growth factors, cancellous bone chips, hydroxyapatite, tri-calcium phosphate, polylactic acid, polyglycolic acid, polygalactic acid, polycaprolactone, polyethylene oxide, polypropylene oxide, polysulfone, polyethylene, polypropylene, hyaluronic acid, bioglass, gelatin, collagen and chopped polymeric fibers or mixtures thereof.

As used herein, the term "cancellous" refers to a bone having a porous structure. The normal type of adult mammalian bone, whether cancellous or compact, is composed of parallel lamellae in the former and concentric lamellae in the latter; lamellar organization reflects a repeating pattern of collagen fibroarchitecture. Adult bone consisting of mineralised regularly ordered parallel collagen fibres more loosely organised than the lamellar bone of the shaft of adult long bones, such as bone found in the end of long bones, is known as "cancellous bone".

In another preferred embodiment, the device can further comprise an osteoinductive component and an osteoconductive component.

The osteoinductive component can include at least one compound selected from the group consisting of fibroblast growth factors, such as (FGFs) FGF-1, FGF-2 and FGF-4; platelet-derived growth factors (PDGFs), such as PDGF-AB, PDGF-BB, PDGF-AA; epithelial growth factors EGFs; insulin-like growth factors (IGF), such as IGF-I, IGF-II; osteogenic protein-1 (OP-1); transforming growth factors (TGFs), such as transforming growth factor-β, transforming growth factor-β1, transforming growth factor-β2, transforming growth factor-β3; osteoid-inducing factor (OIF); angiogenin(s); endothelins; hepatocyte growth factor and keratinocyte growth factor; bone morphogenetic proteins (BMPs), such as osteogenin (bone morphogenetic protein-3), bone morphogenetic protein-2; bone morphogenetic protein-2A, bone morphogenetic protein-2B, bone morphogenetic protein-7; heparin-binding growth factors (HBGFs), such as HBGF-1, HBGF-2; isoforms of platelet-derived growth factors, fibroblast growth factors, epithelial growth factors transforming growth factor-β, insulin-like growth factors, bone morphogenic proteins, the bone morphogenetic proteins and the growth differentiation factors (GDF's); Indian hedgehog, sonic hedgehog, desert hedgehog; cytokines, such as IL-1, IL-2, IL-3, IL-4, IL-5, IL-6; colony-stimulating factors (CSFs), such as CSF-1, G-CSF and GM-CSF or mixtures thereof.

The osteoconductive component can include at least one compound selected from the group consisting of a material having the formula:

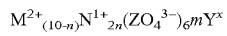

$M^{2+}_{(10-n)}N^{1+}_{2n}(ZO_4^{3-})_6 mY^x$ where
n=1-10, and m=2 when x=1, and/or m=1 when x=2;
M and N are alkali or alkaline earth metals;
$ZO_4$ is an acid radical, where Z is phosphorus, arsenic, vanadium, sulfur or silicon; and
Y is an anion, preferably halide, hydroxide, or carbonate.

The osteoconductive component can further include at least one of material selected from the group consisting of mono-calcium phosphate, di-calcium phosphate, octa-calcium phosphate, alpha-tri-calcium phosphate, beta-tri-calcium phosphate, or tetra-calcium phosphate, hydroxyapatite, fluorapatite, calcium sulfate, calcium fluoride, calcium oxide, silicon dioxide, sodium oxide, and phosphorus pentoxide or mixtures thereof.

In another preferred embodiment, the osteobiologic component can further include at least one water-soluble materials selected from the group consisting of gelatin, salts, polysaccharides and proteins.

Figure 17B:
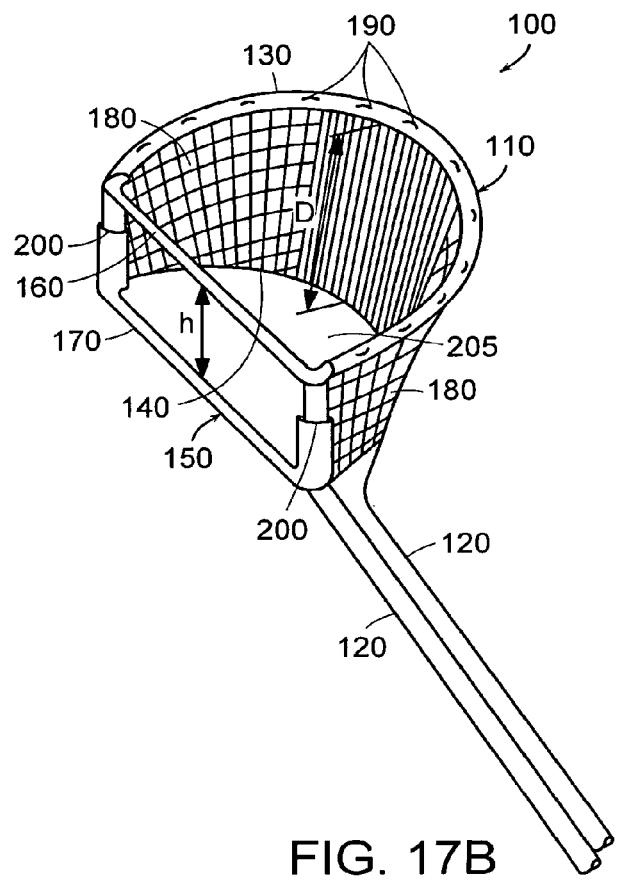
FIGS. 17 (a) and (b) show a particularly preferred embodiment of the device of the present invention in collapsed and expanded configuration, respectively.
Figure 17A:
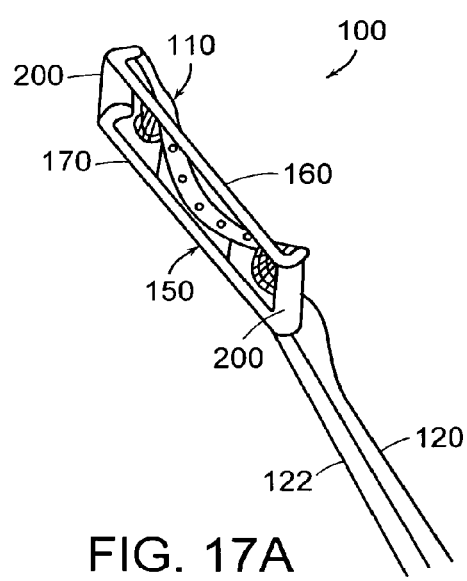

A particularly preferred embodiment of the present invention is an intervertebral spinal fusion device shown in FIGS. 17 (a) (collapsed) and (b) (expanded). The device 100 comprises (a) a partially rigid anterior frame 110 detachably connected to a first fluid communication means 120, said frame having an upper inflatable rim 130 and a lower inflatable rim 140; and (b) a rigid posterior expandable frame 150, detachably connected to a second fluid communication means 122, said frame having a rigid upper rim 160 and a rigid lower rim 170, connected respectively to the upper inflatable rim 130 and lower inflatable rim 140 of the anterior frame 110.

Preferably, the device further comprises at least one mesh element 180 connected to the upper and the lower inflatable rims 130 and 140 of the anterior frame 110. At least one of the upper and the lower inflatable rims 130 and 140 of the anterior frame 110 of the device 100 can have a plurality of outward projections 190.

Most preferably, the posterior frame 150 of the device further includes at least one telescopically expandable supporting element 200, each said supporting element being connected to the upper and the lower rigid rims 160 and 170 of the posterior frame 150.

Device 100 can be inserted into an intervertebral space in a collapsed state 210. Device 100 can next be oriented so that the anterior frame 110 of the device is oriented to face an anterior aspect of a vertebra, the posterior frame 150 of the device is oriented to face a posterior aspect of the vertebra and the upper and lower rims 130, 140, 160 and 170 of each frame face upper and lower vertebral endplates endplates, respectively.

In a preferred embodiment, at least one of the load-bearing component and the osteobiologic component is directed into the device by directing at least one component under pressure through at least one of the first and the second fluid communication means 120 and 122, thereby causing the device to expand and directing the upper inflatable rim 130 and the lower inflatable rim 140 of the anterior frame and a posterior frame 150 of the device against the respective vertebral endplates, thereby at least partially restoring a natural angle between two adjacent vertebrae.

In a particularly preferred embodiment, upon at least partially filling the upper and lower inflatable rims 130 and 140 and the posterior frame 150 between two adjacent vertebrae (not shown), natural angle between said two vertebrae is at least partially restored. Preferably, upon filling the upper and the lower inflatable rims 130 and 140 and the posterior frame 150, the distance D between the upper and the lower inflatable rims is different from the height h of the posterior frame. In one embodiment, upon at least partially filling the upper and the lower inflatable rims 130 and 140, said rims each have a footprint substantially corresponding to a rim of a vertebral endplate. Preferably, upon at least partially filling the upper and the lower inflatable rims 130 and 140 and the posterior frame 150, the device defines an open cavity 205 having an axial and a radial dimensions.

In another preferred embodiment, the present invention is a method of making an intervertebral spinal fusion device comprising (a) inserting an inflatable device through a cannula into an intervertebral space; (b) orienting said inflatable device so that upon expansion a natural angle between two adjacent vertebrae will be at least partially restored; and (c) directing at least one member of the group consisting of a load-bearing component and an osteobiologic component into the inflatable device through the fluid communication means. Most preferably the method of the present invention further includes the step of hardening the load-bearing component. In one embodiment, said inflatable device includes an arcuate balloon connected to at least one fluid communication means, wherein said inflatable device upon expansion between two adjacent vertebrae has a footprint that substantially corresponds to a perimeter of a vertebral endplate and at least partially restores a natural angle between two adjacent vertebrae. In another embodiment, said inflatable device includes at least one inflatable balloon, said device having an upper area, a lower area, an anterior area and a posterior area, and where upon expansion of the upper and the lower areas against the respective vertebral endplates, said anterior area is unequal to than said posterior area height, and a footprint of the device substantially corresponds to a rim of a vertebral endplate. The at least one balloon can contain a plurality of lumena.

Preferably, the anterior area of the inflatable device is oriented to face an anterior aspect of a vertebra and the posterior area of the device is oriented to face a posterior aspect of the vertebra.

Most preferably, at least one of the load-bearing component and the osteobiologic component is directed into the balloon by directing at least one component under pressure through the fluid communication means, thereby causing the balloon to expand and directing the upper area and the lower area of the device against the respective vertebral endplates, thereby at least partially restoring a natural angle between two adjacent vertebrae.

In another preferred embodiment, at least a portion of the device used to practice the method of the present invention, upon expansion, has a generally toroidal shape thereby forming an open cavity defined by an outer surface of the toroidal shape having an axial dimension and a radial dimension. Preferably, the at least a portion of the device is oriented so that the axial dimension of the open cavity is substantially parallel to a major axis of a spinal column of a patient in which the device has been implanted.

In one embodiment, at least one of a load-bearing component and an osteobiologic component can be directed into the open cavity defined by the expanded device.

The method of the present invention can further include the step of dissolving at least one water-soluble material, thereby forming a porous matrix.

Preferably, the method of the present invention further includes the step of directing into the inflatable device osteoinductive and/or osteoconductive components.

In one preferred embodiment, the present invention is a method of at least partially restoring a natural angle between two adjacent vertebrae comprising: (a) inserting an inflatable device through a cannula into an intervertebral space; (b) orienting said inflatable device so that upon expansion a natural angle between two adjacent vertebrae will be at least partially restored; and (c) expanding said inflatable device by directing at least one of a load-bearing component and an osteobiologic component, into said inflatable device. The inflatable devices suitable for practicing the method of the present invention are described above.

Preferably, the method of the present invention includes the step of inflating said inflatable device. Inflating includes introducing at least one of a load-bearing component and an osteobiologic component into said device by directing at least one component through the fluid communication means, thereby allowing the lower area and the upper area to engage the respective endplates and the anterior area height of said inflatable device to be greater than the posterior area height, thereby at least partially restoring or creating a natural angle between two adjacent vertebrae. Most preferably, the method further includes the step of hardening at least one of the load-bearing component and an osteobiologic component.

In a preferred embodiment, the device upon expansion has a generally toroidal shape thereby forming an open cavity defined by an outer surface of the toroidal shape and having an axial dimension and a radial dimension and the step of orienting said inflatable device includes orienting at least a portion of the device so that so that the axial dimension of the open cavity is substantially parallel to a major axis of a spinal column of a patient in which the device has been implanted. In one embodiment, the method further includes the step of introducing at least one of the load-bearing component and the osteobiologic component into the cavity and the step of hardening at least one of the load-bearing component and an osteobiologic component. The method can further includes the step of dissolving at least one water-soluble material, thereby forming a porous matrix.

The invention will now be further and specifically described by the following examples that are not intended to be limiting in any way.

EXEMPLIFICATION

Example 1

Employing a Method of the Present Invention

In performing a preferred method of the present invention, the patient is brought to the pre-surgical area and prepped. Anesthesia is then induced and the area of the spine is further prepped. A small incision through the muscles is opened under dissecting microscopic visualization. The incision is made as small as possible and is longitudinal in the plane of the spine. The paravertebral muscles are separated by blunt dissection and held apart with forceps and dividers. The intervertebral disc area is visualized, with initial exposure down to the lamina. The area below the lamina, at the point of the intervertebral foramina, can also be exposed.

The disc is examined for extruded material and any extruded material is removed. Magnetic resonance imaging ("MRI") data can be used to determine the integrity of the annulus fibrosis at this point. An arthroscope is inserted into the disc and used to examine the inside of the annulus. Optionally, an intraoperative discogram can be performed, in which a dye material is inserted and visualized in order to substantiate the integrity of the annulus fibrosis. Points of weakness, or rents, in the annulus fibrosis are identified and located and suitable means, e.g., a bioabsorbable glue is employed to block these rents. If balloons are used to deliver all of the flowable materials used in the present invention, then the rents need not be patched.

Distraction of the intervertebral disc space can then be accomplished, as described above, by inserting a deflated balloon into the disc space and delivering a fluid (preferably, the flowable load bearing component of the present invention) into the balloon cavity.

Next, the endplates of the opposing vertebral body are partially decorticated, typically through the use of a curette, in order to allow blood flow into the disc space.

After endplate decortication, the application cannula is inserted into the joint or disc space and under visualization from the fiberoptic scope the biomaterial is delivered. The flow of the biomaterial is controlled by the operator via a foot pedal connected to the pumping mechanism on the polymer canister. The biomaterial flows from the tip of the application catheter to fill the space provided.

If the load bearing component has a flowable component, the flowable component is preferably solidified within 3 to 5 minutes, and preferably within 1 to 2 minutes. Once the disc space is suitably distracted, the osteobiologic component of the present invention is introduced to the distracted space, thereby filling the remainder of the disc space. The arthroscopic cannula and the application cannula are removed. The flowable materials are further allowed to harden over 15 to 20 minutes.

The delivered biomaterial is allowed to cure, or cured by minimally invasive means and in such a manner that the cured biomaterial is retained in apposition to the prepared site. As described herein, the biomaterial can be cured by any suitable means, either in a single step or in stages as it is delivered. Once cured, the biomaterial surface can be contoured as needed by other suitable, e.g., endoscopic or arthroscopic, instruments. The joint is irrigated and the instruments removed from the portals.

At that point, interoperative x-rays are obtained to substantiate the preservation of the intervertebral disc space. Direct observation of the intervertebral foramina for free cursing of the nerve rootlet is substantiated by visualization. The retracted muscles are replaced and the local fascia is closed with interrupted absorbable suture. The subcutaneous fascia and skin are then closed in the usual fashion. The wound is then dressed.

Example 2

A Surgical Procedure That Employs Methods and Devices of the Present Invention

A surgical procedure to fuse the vertebrae using methods and devices of the present invention can comprise the following steps:
 i. Puncture or cut a flap in the annulus fibrosus and insert a small diameter tube into the slit,
 ii. Perform a conventional discectomy to remove the nucleus pulposus,
 iii. Insert a small diameter tube, e.g. a cannula, into the disc space through the slit,
 iv. Insert a strut, e.g. a balloon or a ramp having a partially annular shape, into the disc space through the tube,
 v. Flow glucose-containing polycaprolactone into the disc space including the volume defined by the outer surface of the partially annular balloon or a ramp, through the tube at about 70° C. Upon cooling to 37° C., the polycaprolactone should become solid, thereby supplementing the mechanical attributes of the strut,
 vi. Leach out the glucose, thereby forming a porous matrix.
 vii. Flow solutions laden with osteobiologic materials through the porous matrix, so that the osteobiologic materials collect in the pores. The tube can also have a vacuum port to collect the eluted solution.
 viii. remove the tube(s), seal the flap, and wait a month for bone growth.

The result of this procedure is a formation of a fusion cage. This procedure has numerous advantages. First, the resulting cage fills and supports the entire disc space, and so it is stable and is not prone to subsidence. Second, the minimally invasive treatment of the annulus fiborsus allows the resulting cage to be held in place by the retained annulus fibrosus. Third, the in situ formation of a scaffold eliminates the need in high impaction forces. Four, by the very nature of an inflatable device, it is adjusted to fit the desired disc height.

Example 3

Harvesting Progenitor Cells for Use in Osteobiologic Material

Prior to performing spinal surgery, approximately 5 cc of bone marrow is aspirated from the iliac crest of the patient into a heparinized syringe tube. The heparinized marrow is then passed through a selective cell attachment filter. The filter is designed for selective attachment of osteoprogenitor cells such as mesenchymal stem cells and osteoblasts. Following selective cell attachment, the cells are tripsinized off of the filter and collected in a flask. The flask is then centrifuged to precipitate a cell pellet on the bottom of the flask and the supernatant is poured off. The cells are then mixed with the injectable precursor form of the hydrogel. The precursor hydrogel is then poured into molds that are between 50-250 um in any dimension. The precursor hydrogel is then cured, for example with a photoinitiator, to yield cell loaded hydrogel particles. These cell-hydrogel particles are then mixed with the viscous form of the hardenable material and injected as the osteobiologic composition.

Example 4

Desirable Specifications for Lumbar Fusion Device

Specifications for lumbar interbody fusion devices are often formulated assuming the following characteristics:
 a) each vertebral endplate of a patient has a 1500 mm$^2$ cross-sectional area,
 b) the maximum in vivo load experienced by a patient is 3.4 kN;
 c) the ultimate strength of a vertebral body is about 8.2 kN;
 d) the device should initially be able resist the maximum in vivo load;
 e) after one year, the device should be able to resist half the maximum in vivo load,
 f) the strut portion of the device will have a footprint of 20 areal % of the disc space.

Accordingly, the following criteria for the device can be obtained:

Strength of a Load-Bearing Component $$\text{Ultimate Strength} = \frac{8.2 \text{ kN}}{300 \text{ mm}^2} = 27 \text{ MPa} \tag{1}$$

$$\text{Max in Vivo Load} = \frac{3.4 \text{ kN}}{300 \text{ mm}^2} = 11.3 \text{ MPa} \quad (2)$$

Because both the strut and osteobiologic components will initially share the axial compressive load of the spine, the initial minimum strength required by the device may be decreased. If the OB composition is chosen to provide a 5 MPa strength and a 0.05 GPa modulus for at least 6-12 weeks in order to mimic cancellous bone, then the OB composition may share about 10% of the applied compressive load when the modulus of the strut is 2 GPa (assuming no annulus fibrosis). Therefore, the strength of the strut may be about 10% lower.

Modulus of a Load-Bearing Component

It is preferred that the devices of the present invention have a stiffness of at least 0.5 kN/mm. This lower preferred limit corresponds to the stiffness of conventional allograft cages. However, it is believed by some that the low stiffness of the allograft cages may sometime cause too much microfracture in the remodeling process. Therefore, in some embodiments, the stiffness of the devices of the present invention is preferably at least 5 kN/mm. Because it is believed that excessive device stiffness may undesirably cause stress shielding of the osteobiologic composition (and bone resorption), the stiffness of the device of the present invention is desirably no more than 50 kN/mm.

In many embodiments of the present invention, the stiffness of the device of the present invention is between 10 and 20 kN/mm. This range of values is comfortably between the range of stiffnesses found in conventional allograft cages (0.6-2.6 kN/mm) and CFRP cages (20-30 kN/mm). Accordingly, it is believed that the devices of the present invention will have stiffness appropriate for the support of bony fusion through the disc space.

By way of non-limiting explanation, the stiffness of a component can be calculated as follows:

Comp. Modulus(GPa)×Area(mm²)/Disc Space Depth (mm)=Stiffness(kN/mm)  (7).

Assuming a disc space depth of 10 mm and area of 300 mm², the following table can be constructed:

TABLE I

| Intrinsic Material Compressive Modulus (GPa) | Device Stiffness (kN/mm) |
|---|---|
| 0.1 | 3 |
| 0.5 | 15 |
| 1.0 | 30 |
| 1.5 | 45 |

Because both the strut and osteobiologic components will initially share the axial compressive load of the spine, the initial minimum modulus required by the device may be decreased. If the OB composition is chosen to provide a 5 MPa strength and a 0.05 GPa modulus for at least 6-12 weeks in order to mimic cancellous bone, then the OB composition may share about 10% of the applied compressive load when the modulus of the strut is 2 GPa (assuming no annulus fibrosis). Therefore, the modulus of the strut may be about 10% lower.

Similarly, if an initial device stiffness of 15 kN/mm is desired, then the strut stiffness should be about 1 GPa. As noted above, the material reported by Timmer meets this requirement.

Example 5

Combinations of Materials and Devices

By way of introduction, the compositions and materials suitable for use in the present invention will be described below.

Exemplary compositions suitable for use as load-bearing component of the present invention that include a fumarate-based polymer (such as polypropylene fumarate) cross-linked with a cross-linking agent containing a polypropylene fumarate-unit, such as polypropylene fumarate-diacrylate are disclosed in Timmer, *Biomaterials* (2003) 24:571-577 (hereinafter, "Timmer"), the entire teachings of which are incorporated herein by reference. These compositions are characterized by a high initial compressive strength (about 10-30 MPa) that typically increases over the first 12 weeks, high resistance to hydrolytic degradation (about 20-50 at 52 weeks), and an acceptable modulus for use as a strut (0.5-1.2 GPa).

Exemplary compositions suitable for use as resorbable cross-linkable component comprises those cross-linkable components disclosed by Wise in U.S. Pat. No. 6,071,982 (hereinafter, "Wise"), the entire teaching of which are herein incorporated by reference.

Exemplary absorbable elastomeric materials that allows resorbale devices to be delivered through the cannula are disclosed in U.S. Pat. No. 6,113,624 by Bezwada (hereinafter, "Bezwada"), the entire teachings of which are incorporated herein by reference.

Exemplary injectable osteobiologic polymer-based compositions suitable for use in the present invention are described in the U.S. Pat. No. 5,679,723 by Cooper (hereinafter, "Cooper"), the entire teachings of which are incorporated herein by reference.

Exemplary osteobiologic compositions in which porosity is produced in situ, are described in the U.S. Pat. No. 5,522,895 by Mikos (hereinafter, "Mikos"), the entire teachings of which are incorporated herein by reference.

As used herein, "PCL" is polycaprolactone, "PLA" is poly(lactic acid), "PPF" is polypropylene fumarate and "PMMA" is polymethylmethacrylate.

As used herein, "IPN" or "interpenetrating networks" is a composition comprising two cross-linkable polymers, wherein two cross-linkable polymers, upon exposure to appropriate cross-linking agents, cross-links with itself, but not with the other cross-linked polymer. "S-IPN" or "Semi-interpenetrating networks" is a composition comprising a first cross-linkable polymer and a second non-cross-linkable polymer wherein, upon exposure to an appropriate cross-linking agent, the first cross-linkable polymer cross-links with itself, while the second polymer remains unaffected.

According to Hao, *Biomaterials* (2003), 24:1531-39, (hereinafter, "Hao") the entire teachings of which are incorporated herein by reference, certain mechanical properties of polycaprolactone increased by about 3 fold when it was formed as a S-IPN. When at least 15 wt % HAP was added, the tensile modulus increased to 6 fold over conventional polycaprolactone.

Using the assumptions and criteria presented in Example 4, the combinations of materials and devices of the present invention, provided below in Table II, were selected:

TABLE II

| Combination | LOAD-BEARING Component | | OSTEOBIOLOGIC Component | |
|---|---|---|---|---|
| | Composition | Balloon | Composition | Balloon |
| 1. | Timmer PPF | Short lived | Wise-foam lock | Bezwada |
| 2. | PCL | Short lived | Cooper | None |
| 3. | PCL S-IPN | Short lived | Wise | Bezwada |
| 4. | $CaPO_4$ | Long lived | $CaPO_4$ | None |
| 5. | Wise PPF | Long lived | Mikos porogen | None |
| 6. | PMMA-PCL | Permanent | TBD | TBD |
| 7. | none | none | PLA beads | Non-compliant |
| 8. | none | none | Timmer w/ porogen | Reinforced stiff sidewalls |

Combination 1

In this example, the Timmer IPN composition is chosen as the load bearing composition in the strut because it has sufficient initial and long term strength, acceptable modulus, and is resorbable.

Since the Timmer composition contains monomers, it is desirable to contain the composition in an inflatable device during curing. Since the Timmer composition is relatively resistant to degradation, the inflatable device can be made of a resorbable material having a short half life. Since the strut should also act as the distracter, the balloon should be non-compliant.

The Wise composition is chosen as the osteobiologic composition because is forms a scaffold having a strength and modulus essentially similar to that of cancellous bone. It can be infiltrated in-situ with a hydrogel containing osteogenic cells and osteoinductive growth factors.

Since the Wise composition contains monomers, it is desirable to contain the composition in an inflatable device during curing. Since bone in-growth is desirable through the region occupied by the balloon, the inflatable device should be made of a resorbable material having a very short half life (such as one day). Since the Wise composition a 25% expansion during pore formation, it would be desirable for the balloon to be compliant to allow the Wise composition conform to the disc space contour.

Combination 2

In this example, solid neat polycaprolactone is chosen as the load bearing composition in the strut because it has sufficient initial strength (15 MPa), is very resistant to degradation, has an acceptable modulus (0.5 GPa), and is resorbable.

Since solid polycaprolactone is relatively resistant to regradation, the inflatable device need not be relatively resistant to degradation, and so can be made of a resorbable material having a short half life. Since the strut should also act as the distracter, the balloon should be non-compliant.

The Cooper composition is chosen as the osteobiologic composition because it is flowable at 40° C., and degrades sufficiently within a few months to form an hydroxyapatite based-scaffold. Because of its low delivery temperature, certain dimer bone morphogenetic proteins can also be delivered during the injection of this composition.

Since the Cooper composition is fully biodegradable, there is no real need to contain the composition in an inflatable device.

However, if it would be desirable to inject enough of the Cooper composition to conform it to the disc space contour, then it may be desirable to contain it in an inflatable device. Since bone in-growth is desirable through the osteobiologic composition, the inflatable device should be made of a resorbable material having a very short half-life (such as one day).

Combination 3

In this example, the polycaprolactone S-IPN composition (as reported in Hao) is chosen as the load bearing composition in the strut because it may have mechanical properties about 3-6 fold greater than neat polycaprolactone, and is resorbable.

Since the polycaprolactone-polycaprolactone composition contains monomers, it is desirable to contain the composition in an inflatable device during curing. Since the polycaprolactone composition is relatively resistant to degradation, the inflatable device can be made of a resorbable material having a short half life. Since the strut should also act as the distracter, the balloon should be non-compliant.

Combination 4

In this example, $CaPO_4$ is chosen as the load bearing composition in the strut because it has sufficient initial and long term strength, acceptable modulus, and is resorbable.

Since $CaPO_4$ is very susceptible to degradation, the inflatable device need be relatively resistant to degradation, and so should be made of a resistant material that can contain the $CaPO_4$ for at least one year. Since the strut should also act as the distracter, the balloon should be non-compliant. One material that is resistant and non-compliant is polyetherether ketone.

The $CaPO_4$ composition is chosen as the osteobiologic composition because it is flowable at body temperature, and degrades sufficiently within a few months to form an hydroxyapatite based-scaffold. Because of its delivery at body temperature, hydrogels containing temperature sensitive additives, such as osteogenic cells and osteoinductive components (such as bone morphogenetic proteins), can also be delivered during the injection of this composition.

Since the $CaPO_4$ composition is fully biodegradable, there is no real need to contain the composition in an inflatable device.

Combination 5

In this example, the Wise composition is chosen as the load bearing composition in the strut because it has sufficient initial strength, acceptable modulus, and is resorbable.

Since the Wise composition is very susceptible to degradation, the inflatable device need be relatively resistant to degradation, and so should be made of a resistant material that can contain the Wise Composition for at least one year. Since the strut should also act as the distracter, the balloon should be non-compliant. One material that is resistant and non-compliant is polyetherether ketone.

The Mikos composition is chosen as the osteobiologic composition because it is injectable at body temperature, forms an in-situ scaffold in which hydrogels containing temperature sensitive additives, such as osteogenic cells and osteoinductive components (such as bone morphogenetic proteins), can be delivered.

Since a hydrogel should be injected into the Mikos composition during surgery, it is desirable to inject the Mikos composition without the aid of a balloon.

Combination 6

In this example, which is disclosed in Mendez, *JBMR* (2002), 61:66-74, the entire teachings of which are incorporated herein by reference, $CaPO_4$ is chosen as the load bearing composition in the strut because it has sufficient initial and long term strength, acceptable modulus, and is resorbable.

Since $CaPO_4$ is very susceptible to degradation, the inflatable device need be relatively resistant to degradation, and so should be made of a resistant material that can contain the $CaPO_4$ for at least one year. Since the strut should also act as the distracter, the balloon should be non-compliant. One material that is resistant and non-compliant is polyetherether ketone.

Combination 7

The polylactic acid beads are chosen as the matrix of the osteobiologic composition because they can be packed into the disc space at body temperature and heat bonded with hot water to form an in-situ formed scaffold. If the beads are selected to have a 2 mm diameter, the porosity of the resulting scaffold will be about 40 vol % with a pore size of about 500 urn. Hydrogels containing temperature sensitive additives, such as osteogenic cells and osteoinductive components (such as bone morphogenetic proteins), can then be delivered the in-situ scaffold.

Since the packed beads must be packed into the disc space and then heat bonded with a high temperature fluid, it may be desirable to contain both the beads and the hot fluid in a balloon.

The Nitonol reinforced balloon is desirable because the reinforcements can help the balloon withstand the high pressures needed during packing.

Since the polylactic acid beads have sufficient initial and long term strength, acceptable modulus, there is no need for a strut.

Combination 8

Timmer polypropylene fumarate-polypropylene fumarate-diacrylate with tricalcium phosphate (Embodiment B) with 50 vol % porosity (or seeded hydrogel phase) will still have a 25 MPa compressive strength after one year. If it takes the whole disc space, only 11.3 MPa is required. 2× safety factor.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. An intervertebral fusion device for insertion between upper and lower vertebral endplates, the device comprising:
   a) upper and lower plates, each plate having an outer bearing surface for bearing against a respective vertebral endplate, an inner surface, and a longitudinal length; and
   b) a core disposed between the outer bearing surfaces of the plates and running longitudinally along the length of the plates;
   wherein the device has an unexpanded configuration in which the outer bearing surfaces are relatively close and an expanded configuration in which the outer bearing surfaces are relatively distant;
   wherein the outer bearing surfaces are substantially parallel to one another in each of the unexpanded and expanded configurations;
   wherein at least a portion of each inner surface extends at an oblique angle from its respective outer bearing surface in a longitudinal direction;
   wherein the core does not contact either inner surface when the device is in each of the unexpanded configuration and the expanded configuration;
   wherein at least a portion of the inner surfaces are parallel to each other; and
   wherein the inner surfaces nest with each other in the unexpanded configuration.

2. The device of claim 1, wherein each plate has an opening in its outer bearing surface sized to permit bony fusion therethrough from the upper vertebral endplate to the lower vertebral endplate.

3. The device of claim 1, wherein a proximal portion of each inner surface extends at an angle from its respective outer bearing surface.

4. The device of claim 3, wherein a distal portion of each inner surface extends at an angle from its respective outer bearing surface.

5. The device of claim 1, wherein the core is metallic.

6. The device of claim 1, wherein a maximum height of the upper plate is equal to a maximum height of the device when the device is in the unexpanded configuration.

7. The device of claim 6, wherein a maximum height of the lower plate is equal to a maximum height of the device when the device is in the unexpanded configuration.

8. The device of claim 1, wherein the inner surfaces engage one another when the device is in the unexpanded configuration.

9. The device of claim 1, wherein at least a portion of each inner surface extends at an acute angle from its respective outer bearing surface.

10. An intervertebral implant for insertion between upper and lower vertebrae, the implant comprising:
    an upper plate having an outer bearing surface for bearing against an upper vertebra and an inner surface opposite the outer bearing surface;
    a lower plate having an outer bearing surface for bearing against a lower vertebra and an inner surface opposite the outer bearing surface; and
    a core disposed between the outer bearing surfaces of the plates;
    wherein the implant has a first configuration in which the outer bearing surfaces of the upper and lower plates are spaced apart by a first distance and a second configuration in which the outer bearing surfaces of the upper and lower plates are spaced apart by a second distance that is greater than the first distance;
    wherein at least a portion of each inner surface extends at an angle from its respective outer bearing surface and wherein said angled portions of each inner surface contact each other when the implant is in the first configuration;
    wherein the inner surfaces are parallel to each other; and
    wherein at least a portion of the core is disposed between the outer bearing surfaces of the plates when the implant is in the first configuration.

11. The implant of claim 10, wherein the core does not contact either inner surface when the implant is in each of the first configuration and the second configuration.

12. The implant of claim 10, wherein each plate has an opening in its outer bearing surface sized to permit bony fusion therethrough from the upper vertebra to the lower vertebra.

13. The implant of claim 10, wherein a proximal portion of each inner surface extends at an angle from its respective outer bearing surface.

14. The implant of claim 13, wherein a distal portion of each inner surface extends at an angle from its respective outer bearing surface.

15. The implant of claim 10, wherein the core is metallic.

16. The implant of claim 10, wherein a maximum height of the upper plate is equal to a maximum height of the implant when the implant is in the first configuration.

17. The implant of claim 16, wherein a maximum height of the lower plate is equal to a maximum height of the implant when the implant is in the first configuration.

18. The implant of claim 10, wherein at least a portion of each inner surface extends at an acute angle from its respective outer bearing surface.

* * * * *